United States Patent
Bonneau et al.

(10) Patent No.: US 7,300,948 B2
(45) Date of Patent: Nov. 27, 2007

(54) ALKYNYL COMPOUNDS AS NON NUCLEOSIDE REVERSE TRANSCRIPTASE INHIBITORS

(75) Inventors: Pierre Bonneau, Laval (CA); Patrick Deroy, Laval (CA); Alexandre Gagnon, Laval (CA); Jeffrey O'Meara, Boisbriand (CA); Bruno Simoneau, Laval (CA); Christiane Yoakim, Laval (CA)

(73) Assignee: Boehringer Ingelheim International GmbH, Ingelheim (DE)

( * ) Notice: Subject to any disclaimer, the term of this patent is extended or adjusted under 35 U.S.C. 154(b) by 163 days.

(21) Appl. No.: 11/238,732

(22) Filed: Sep. 29, 2005

(65) Prior Publication Data

US 2006/0069261 A1 Mar. 30, 2006

Related U.S. Application Data

(60) Provisional application No. 60/614,576, filed on Sep. 30, 2004.

(51) Int. Cl.
*C07D 401/02* (2006.01)
*C07D 213/02* (2006.01)
*A61K 31/44* (2006.01)

(52) U.S. Cl. ............ 514/357; 514/358; 514/473; 514/563; 514/621; 546/309; 546/337; 549/475; 558/411; 562/433; 564/169

(58) Field of Classification Search ........... 514/357, 514/358; 546/309, 337; 549/475; 558/411; 562/433; 564/169
See application file for complete search history.

(56) References Cited

FOREIGN PATENT DOCUMENTS

| CA | 2439820 A1 | 9/2002 |
| WO | WO 01/17982 A1 * | 3/2001 |
| WO | 02070470 A2 | 9/2002 |
| WO | 2004050643 A2 | 6/2004 |

OTHER PUBLICATIONS

Wyatt et al, Journal of Medicinal Chemistry, vol. 38, pp. 1657-1665, 1995.*
Chan, et al; Novel Benzophenones as Non-nucleoside Reverse Transcriptase Inhibitors of HIV-1; Journal of Medicinal Chemistry; 2004; vol. 47; pp. 1175-1182.
International Preliminary Report on Patentability for PCT/CA2005/001480.

* cited by examiner

*Primary Examiner*—Zinna N. Davis
(74) *Attorney, Agent, or Firm*—Michael P. Morris; Mary-Ellen M. Devlin; Alan R. Stempel

(57) ABSTRACT

Inhibitors of HIV reverse transcriptase which are useful for the treatment of HIV infection. Exemplars of the invention are compounds of the formula

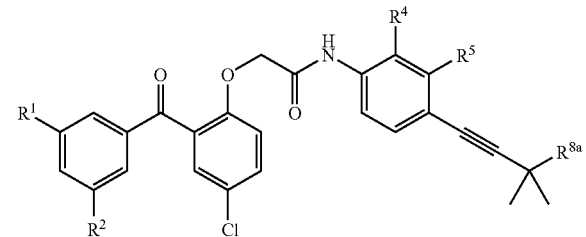

wherein the substituents are as defined in the following table

| $R^1$ | $R^2$ | $R^4$ | $R^5$ | $R^{8a}$ |
|---|---|---|---|---|
| F | $CF_3$ | Me | H | —OH |
| F | $CF_3$ | Cl | H | —OH |
| F | $CF_3$ | Me | H | —O—$CH_2CO_2H$ |
| Cl | CN | Cl | H | —OH. |

15 Claims, No Drawings

ALKYNYL COMPOUNDS AS NON NUCLEOSIDE REVERSE TRANSCRIPTASE INHIBITORS

RELATED APPLICATIONS

This application claims benefit of U.S. Ser. No. 60/614,576, filed Sep. 30, 2004.

TECHNICAL FIELD OF THE INVENTION

The invention relates to compounds and pharmaceutically acceptable salts or esters thereof, their use, either alone or in combination with other therapeutic agents, in the treatment or prophylaxis of HIV infection, and to pharmaceutical compositions comprising the compounds that are active against HIV.

BACKGROUND OF THE INVENTION

The disease known as acquired immune deficiency syndrome (AIDS) is caused by the human immunodeficiency virus (HIV), particularly the strain known as HIV-1. In order for HIV to be replicated by a host cell, the information of the viral genome must be integrated into the host cell's DNA. However, HIV is a retrovirus, meaning that its genetic information is in the form of RNA. The HIV replication cycle therefore requires a step of transcription of the viral genome (RNA) into DNA, which is the reverse of the normal chain of events. An enzyme that has been aptly dubbed reverse transcriptase (RT) accomplishes the transcription of the viral RNA into DNA. The HIV virion includes copies of RT along with the viral RNA.

Reverse transcriptase has three known enzymatic functions; it acts as an RNA-dependent DNA polymerase, as a ribonuclease, and as a DNA-dependent DNA polymerase. Acting as an RNA-dependent DNA polymerase, RT transcribes a single-stranded DNA copy of the viral RNA. Acting as a ribonuclease, RT destroys the original viral RNA, and frees the DNA just produced from the original RNA. Finally, acting as a DNA-dependent DNA polymerase, RT makes a second, complementary DNA strand, using the first DNA strand as a template. The two strands form double-stranded DNA, which is integrated into the host cell's genome by another enzyme called integrase.

Compounds that inhibit the enzymatic functions of HIV-1 reverse transcriptase will inhibit replication of HIV-1 in infected cells. Such compounds are useful in the prevention or treatment of HIV-1 infection in human subjects, as demonstrated by known RT inhibitors such as zidovudine, didanosine, zalcitabine, stavudine, lamivudine, emtricitabine, abacavir, tenofovir, nevirapine, delavirdine and efavirenz, the main drugs thus far approved for use in the treatment of AIDS.

As with any antiviral therapy, use of RT inhibitors in the treatment of AIDS eventually leads to a virus that is less sensitive to the given drug. Resistance (reduced sensitivity) to these drugs is the result of mutations that occur in the reverse transcriptase segment of the pol gene. Several mutant strains of HIV have been characterized, and resistance to known therapeutic agents is believed to be due to mutations in the RT gene. One of the more commonly observed mutants clinically for the non-nucleoside reverse transcriptase inhibitors is the K103N mutant, in which a lysine (K), at codon 103, has been mutated to a asparagine (N) residue. Other mutants, which emerge with varying frequency during treatment using known antivirals, include single mutants Y181C, G190A, Y188C, and P236L, and double mutants K103N/Y181C, K103N/P225H, K103N/V108I and K103N/L100I.

As antiviral use in therapy and prevention of HIV infection continues, the emergence of new resistant strains is expected to increase. There is therefore an ongoing need for new inhibitors of RT, which have different patterns of effectiveness against the various resistant mutants.

Non-nucleoside inhibitors of HIV reverse transcriptase containing a benzophenone moiety have been described in Wyatt et al, *Journal of Medicinal Chemistry* (1995) 38: 1657-1665 and in International patent applications WO 01/17982 (Glaxo) and WO 02/070470 (SmithKline Beecham). As well, non-nucleoside inhibitors of HIV reverse transcriptase have been described in WO 2004/050643 (Boehringer Ingelheim).

SUMMARY OF THE INVENTION

The present invention provides novel compounds which show potent activity against wild type HIV reverse transcriptase as well as against single mutant and double mutant strains.

The invention provides compounds of formula (I) which are useful for the manufacture of a medicament for treating HIV infection in a human infected by HIV. The compounds are potent inhibitors of wild-type (WT) and double mutant strains of HIV-1 RT, particularly the double mutant K103N/Y181C.

In a first aspect the invention provides a compound of formula (I):

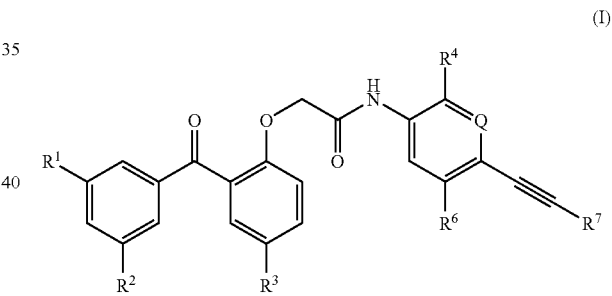

(I)

wherein
$R^1$ and $R^2$ are each independently selected from H, halo, cyano, $(C_{1-4})$alkyl, $(C_{2-4})$alkenyl, $(C_{2-4})$alkynyl, $(C_{3-6})$cycloalkyl, —O—$(C_{1-4})$alkyl, —COO$(C_{1-4})$alkyl, —CONH$_2$, —CONH$(C_{1-4})$alkyl and —CON$((C_{1-4})$alkyl$)_2$; wherein said $(C_{1-4})$alkyl is optionally substituted with one, two or three halo substituents; and wherein said —O—$(C_{1-4})$alkyl is optionally substituted with —COO$(C_{1-4})$alkyl or one, two or three halo substituents;
with the proviso that when $R^1$ is H, $R^2$ cannot be H;
$R^3$ is selected from H and halo;
$R^4$ is selected from $(C_{1-4})$alkyl, halo and nitro;
Q is selected from N and $CR^5$; wherein $R^5$ is selected from H and halo;
$R^6$ is selected from H and halo;
$R^7$ is selected from —$(C_{1-6})$alkyl-$R^8$ and a 5-membered saturated heterocycle containing one heteroatom selected from N, O and S;
  wherein said heterocycle is optionally substituted with one, two or three substituents each independently selected from $(C_{1-6})$alkyl and oxo; and wherein the $(C_{1-6})$alkyl portion of said —$(C_{1-6})$alkyl-$R^8$ is optionally monosubstituted with —OH and optionally substituted with from one to six halo substituents; and wherein $R^8$ is selected from:
a) —OH, —COOH, —CONHSO$_2$R$^9$, —C(=O)NHOH, —OC(=O)NH$_2$ or —NH$_2$, wherein $R^9$ is $(C_{1-6})$alkyl or $(C_{3-7})$cycloalkyl;
b) —O—$(C_{2-6})$alkyl-OH, —NH—$(C_{2-6})$alkyl-OH, —O—$(C^{1-6})$alkyl-$R^{81}$ or —NH—$(C_{1-6})$alkyl-$R^{81}$, wherein $R^{81}$ is selected from Het, —CONHSO$_2$R$^9$, and —COOH; wherein $R^9$ is as defined above;
c) —NHC(=O)—$R^{82}$, wherein $R^{82}$ is selected from $(C_{1-6})$alkyl, $(C_{2-6})$alkenyl, $(C_{3-7})$cycloalkyl, phenyl, —NH$_2$, —NH$(C_{1-6})$alkyl, —N$((C_{1-6})$alkyl$)_2$ and Het; each of said $(C_{1-6})$alkyl, $(C_{2-6})$alkenyl, $(C_{3-7})$cycloalkyl, phenyl and Het being optionally substituted with one or more substituents each independently selected from —OH, —COOH, —CONHSO$_2$R$^9$, —SO$_2$NH$_2$, —NH$_2$, —NH$(C_{1-6})$alkyl, —N$((C_{1-6})$alkyl$)_2$, Het and —NH-Het; wherein $R^9$ is as defined above;
wherein the $(C_{1-6})$alkyl portions of said —NH$(C_{1-6})$alkyl and —N$((C_{1-6})$alkyl$)_2$ are each independently optionally substituted with —O$(C_{1-6})$alkyl, —CONHSO$_2$R$^9$, or —COOH; wherein $R^9$ is as defined above; and wherein said Het and the Het portion of said —NH—Het are each optionally substituted with —COOH or —CONHSO$_2$R$^9$;
wherein $R^9$ is as defined above; and
d) —C(=O)N($R^{83}$)$R^{84}$, wherein $R^{83}$ is selected from H and $(C_{1-6})$alkyl; and $R^{84}$ is selected from $(C_{1-6})$alkyl and Het, each of said $(C_{1-6})$alkyl and Het being optionally substituted with one or more substituents each independently selected from —OH, —COOH, —CONHSO$_2$R$^9$ and —SO$_3$H; wherein $R^9$ is as defined above;
or $R^{83}$ and $R^{84}$ are linked, together with the nitrogen atom to which they are bonded, to form a 5- or 6-membered monocyclic heterocycle which may be saturated, unsaturated or aromatic and which may optionally contain from one to three additional heteroatoms each independently selected from N, O and S; said heterocycle being optionally substituted with —COOH or —CONHSO$_2$R$^9$; wherein $R^9$ is as defined above;

wherein Het is a 4-, 5- or 6-membered heterocycle or a 9- or 10-membered heterobicycle, each of which may be saturated, unsaturated or aromatic and of which may optionally contain from one to four heteroatoms each independently selected from N, O and S, wherein each said N heteroatom may, independently and where possible, exist in an oxidized state such that it is further bonded to an oxygen atom to form an N-oxide group and wherein each said S heteroatom may, independently and where possible, exist in an oxidized state such that it is further bonded to one or two oxygen atoms to form the groups SO or SO$_2$;

or a salt or ester thereof.

According to a further aspect of the invention, there is provided a pharmaceutical composition, comprising a compound of formula (I) as defined hereinbefore and hereinafter, or a pharmaceutically acceptable salt or ester thereof, and optionally one or more pharmaceutically acceptable carriers.

According to yet another aspect of the invention, there is provided a pharmaceutical composition, comprising a compound of formula (I) as defined hereinbefore and hereinafter, or a pharmaceutically acceptable salt or ester thereof, in combination with one or more other antiretroviral agents.

The invention also provides the use of a pharmaceutical composition comprising a compound of formula (I) as defined hereinbefore and hereinafter, or a pharmaceutically acceptable salt or ester thereof, for the treatment of HIV infection in a mammal.

Also provided is the use of a pharmaceutical composition comprising a combination of compound of formula (I) as defined hereinbefore and hereinafter, or a pharmaceutically acceptable salt or ester thereof, and one or more other antiretroviral agents, for the treatment of HIV infection in a mammal.

Another important aspect of the invention involves a method of treating HIV infection in a mammal comprising administering to the mammal an anti-HIV effective amount of a compound of formula (I) as defined hereinbefore and hereinafter, or a pharmaceutically acceptable salt or ester thereof.

In one embodiment of this aspect of the invention, the method of treating HIV infection in a mammal comprises administering to the mammal an anti-HIV effective amount of a combination of a compound of formula (I) as defined hereinbefore and hereinafter, or a pharmaceutically acceptable salt or ester thereof, and at least one other antiretroviral agent.

Yet another aspect of the invention provides the use of a compound of formula (I) as defined hereinbefore and hereinafter, or a pharmaceutically acceptable salt or ester thereof, for the treatment of HIV infection in a mammal.

Still another important aspect of the invention involves a method of treating HIV infection in a mammal comprising administering to the mammal an anti-HIV effective amount of a pharmaceutical composition comprising a compound of formula (I) as defined hereinbefore and hereinafter, or a pharmaceutically acceptable salt or ester thereof.

In one embodiment of this aspect of the invention, the method of treating HIV infection in a mammal comprises administering to the mammal an anti-HIV effective amount of a pharmaceutical composition comprising a combination of a compound of formula (I) as defined hereinbefore and hereinafter, or a pharmaceutically acceptable salt or ester thereof, and at least one other antiretroviral agent.

According to another aspect of the invention, there is provided a method of inhibiting HIV-1 replication by exposing the virus to an inhibitory amount of a compound of formula (I) as defined herein or of a pharmaceutically acceptable salt or ester thereof.

Yet another aspect of the invention provides the use of a compound of formula (I), or of a pharmaceutically acceptable salt or ester thereof, to inhibit HIV-1 replication.

According to another aspect of the invention, there is provided the use of a compound of formula (I) as defined hereinbefore and hereinafter, or a pharmaceutically acceptable salt or ester thereof, for the manufacture of a medicament for the treatment of HIV infection.

According to yet another aspect of the invention, there is provided the use of a compound of formula (I) as defined hereinbefore and hereinafter, or a pharmaceutically acceptable salt or ester thereof, in combination with one or more other antiretroviral agents, for the manufacture of a medicament for the treatment of HIV infection.

Another aspect of the invention provides an article of manufacture comprising a composition effective to treat HIV infection; and packaging material comprising a label which indicates that the composition can be used to treat HIV infection; wherein the composition comprises a compound of formula (I) as defined hereinbefore and hereinafter, or a pharmaceutically acceptable salt thereof.

DETAILED DESCRIPTION OF THE INVENTION

Definitions

The following definitions apply unless otherwise noted:

As used herein, the term "$(C_{1-n})$alkyl", wherein n is an integer, either alone or in combination with another radical, is intended to mean acyclic straight or branched chain alkyl radicals containing from one to n carbon atoms. Examples of such radicals include, but are not limited to, methyl (Me), ethyl (Et), propyl (Pr), 1-methylethyl (iPr), butyl (Bu), 1-methylpropyl, 2-methylpropyl (iBu), and 1,1-dimethylethyl (tBu), wherein the abbreviations commonly used herein are given in brackets.

As used interchangeably herein, the term "—O—$(C_{1-n})$alkyl" or "$(C_{1-n})$alkoxy", wherein n is an integer, either alone or in combination with another radical, refers to alkoxy radicals containing one to n carbon atoms and includes, but is not limited to, methoxy (—OMe), ethoxy (—OEt), propoxy (—OPr), 1-methylethoxy (—OiPr), butoxy (—OBu) and 1,1-dimethylethoxy (—OtBu), wherein the abbreviations commonly used herein are given in brackets. When an —O—$(C_{1-n})$alkyl group is substituted, it is understood to be substituted on the $(C_{1-n})$alkyl portion thereof.

As used interchangeably herein, the term "—S—$(C_{1-n})$alkyl" or "$(C_{1-n})$alkylthio", wherein n is an integer, either alone or in combination with another radical, refers to alkylthio radicals containing one to n carbon atoms and includes methylthio (—SMe), ethylthio (—SEt), propylthio (—SPr), (1-methylethyl)thio (—SiPr), butylthio (—SBu) and (1,1-dimethylethyl)thio (—StBu), wherein the abbreviations commonly used herein are given in brackets. When an —S—$(C_{1-n})$alkyl group is substituted, it is understood to be substituted on the $(C_{1-n})$alkyl portion thereof.

The term "oxo" as used herein means an oxygen atom attached to a carbon atom as a substituent by a double bond (=O).

The term "thioxo" as used herein means an sulfur atom attached to a carbon atom as a substituent by a double bond (=S).

As used herein, the term "halo" means a halogen radical selected from bromo, chloro, fluoro or iodo.

As used herein, the term "COOH" refers to a carboxylic acid group. It is well known to one skilled in the art that carboxylic acid groups may be substituted by functional group equivalents. Examples of such functional group equivalents that are contemplated by this invention include, but are not limited to, esters, amides, imides, boronic acids, tetrazoles, triazoles, N-acylsulfamides ($RCONHSO_2NR_2$), and N-acylsulfonamides ($RCONHSO_2R$).

As used herein, the term "functional group equivalent" is intended to mean an atom or group that is replaceable by another atom or group that has similar electronic, hybridization or bonding properties.

As used herein, the term "$(C_{2-n})$alkenyl", wherein n is an integer, either alone or used with another radical, means an unsaturated, acyclic, straight or branched chain radical containing two to n carbon atoms, at least two of which are bonded to each other by a double bond and includes, but is not limited to, —CH=$CH_2$, —$CH_2$CH=$CH_2$, —$CH_2$CH=$CHCH_3$ and —CH(Me)CH=$CH_2$. Unless specified otherwise, the term "$(C_{2-n})$alkenyl" is understood to encompass individual stereoisomers where possible, including but not limited to (E) and (Z) isomers, and mixtures thereof. A $(C_{2-n})$alkenyl radical may be substituted on any of the carbon atoms thereof which would otherwise bear a hydrogen atom.

The term "$(C_{2-n})$alkynyl", as used herein, wherein n is an integer, either alone or in combination with another radical, is intended to mean an unsaturated, acyclic straight or branched chain radical containing two to n carbon atoms, at least two of which are bonded to each other by a triple bond. Examples of such radicals include, but are not limited to, ethynyl, 1-propynyl, 2-propynyl, and 1-butynyl. A $(C_{2-n})$alkynyl radical may be substituted on any of the carbon atoms thereof which would otherwise bear a hydrogen atom.

The term "$(C_{3-m})$cycloalkyl" as used herein, wherein m is an integer, either alone or in combination with another substituent, means a cycloalkyl substituent containing from 3 to m carbon atoms and includes, but is not limited to, cyclopropyl (cPr), cyclobutyl (cBu), cyclopentyl, cyclohexyl and cycloheptyl, wherein the abbreviations commonly used herein are given in brackets.

The term "$(C_{3-m})$cycloalkyl-$(C_{1-n})$alkyl-" as used herein, wherein n and m are both integers, means an alkyl radical containing from 1 to n carbon atoms to which a cycloalkyl radical containing from 3 to m carbon atoms is directly linked; including, but not limited to, cyclopropylmethyl, cyclobutylmethyl, cyclopentylmethyl, 1-cyclopentylethyl, 2-cyclopentylethyl, cyclohexylmethyl, 1-cyclohexylethyl and 2-cyclohexylethyl. When a $(C_{3-m})$cycloalkyl-$(C_{1-n})$alkyl-group is substituted, it is understood, unless otherwise specified, that the substituent may be attached to either the cycloalkyl or the alkyl portion thereof.

The term "phenyl-$(C_{1-n})$alkyl-" as used herein, wherein n is an integer, means an alkyl radical containing from 1 to n carbon atoms to which a phenyl radical is directly linked; including, but not limited to, phenylmethyl (also known as benzyl), 1-phenylethyl, 2-phenylethyl, 2-phenyl-1-methylethyl, 1-phenyl-1-methylethyl, 1-phenylpropyl, 2-phenylpropyl, and 3-phenylpropyl. When a phenyl-$(C_{1-n})$alkyl-group is substituted, it is understood, unless otherwise specified, that the substituent may be attached to either the phenyl or the alkyl portion thereof.

As used herein, the term "Het" is defined as 4-, 5- or 6-membered heterocycle or a 9- or 10-membered heterobicycle, each of which may be saturated, unsaturated or aromatic and each of which may optionally contain from one to four heteroatoms each independently selected from N, O and S, wherein each said N heteroatom may, independently and where possible, exist in an oxidized state such that it is further bonded to an oxygen atom to form an N-oxide group and wherein each said S heteroatom may, independently and where possible, exist in an oxidized state such that it is further bonded to one or two oxygen atoms to form the groups SO or $SO_2$, unless otherwise specified. When a Het group is substituted, it may be substituted on any carbon atom or heteroatom thereof which would otherwise bear a hydrogen atom, unless specified otherwise. Substituents which may be bonded to carbon atoms or to heteroatoms are those which give rise to chemically stable compounds, such as are recognized by those skilled in the art.

As used herein, the term "heterocycle", either alone or in combination with another radical, is intended to mean a monovalent radical derived by removal of a hydrogen from a 4-, 5- or 6-membered saturated or unsaturated (including aromatic) heterocycle containing 1 to 4 heteroatoms each independently selected from N, O and S. Examples of such heterocycles include, but are not limited to, pyrrolidine, tetrahydrofuran, thiazolidine, pyrrole, furan, thiophene, 1H-imidazole, isoxazole, thiazole, tetrazole, piperidine, piperazine, 1,4-dioxane, 4-morpholine, 4-thiomorpholine, pyridine, pyridine-N-oxide or pyrimidine, or the following heterocycles:

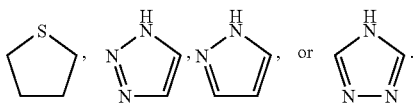

As used herein, the term "heterobicycle" either alone or in combination with another radical, means a heterocycle as defined above fused to another cycle, be it a heterocycle, a phenyl or any other cycle. Examples of such heterobicycles include, but are not limited to, indole, benzimidazole, thiazolo[4,5-b]-pyridine, quinoline, isoquinoline, or coumarin, or the following:

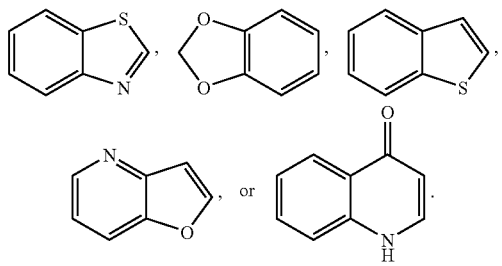

As used herein, the term "inhibitor of HIV replication" refers to an agent capable of reducing or eliminating the ability of HIV-1 reverse transcriptase to replicate a DNA copy from an RNA template.

As used herein, the term "single or double mutant strains" means that either one or two amino acid residues that are present in WT HIV-1 strain have been replaced by residues not found in the WT strain. For example, for the single mutant Y181C, the tyrosine at residue 181 of the wild type HIV reverse transcriptase enzyme has been replaced by a cysteine residue. Similarly, for the double mutant K103N/Y181C, an asparagine residue has replaced the lysine at residue 103 of the wild type HIV reverse transcriptase enzyme and a cysteine residue has replaced the tyrosine at residue 181.

The term "ester thereof" means any ester of a compound in which any of the —COOH functions of the molecule is replaced by a —COOR function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof. The term "ester thereof" includes but is not limited to pharmaceutically acceptable esters thereof.

The term "pharmaceutically acceptable ester" as used herein, either alone or in combination with another substituent, means esters of the compound of formula I in which any of the COOH functions of the molecule are replaced by a —COOR function, in which the R moiety of the ester is selected from alkyl (including, but not limited to, methyl, ethyl, propyl, 1-methylethyl, 1,1-dimethylethyl, butyl); alkoxyalkyl (including, but not limited to methoxymethyl); acyloxyalkyl (including, but not limited to acetoxymethyl); aryl-alkyl-(including, but not limited to, benzyl); aryloxyalkyl (including, but not limited to, phenoxymethyl); aryl (including, but not limited to phenyl), optionally substituted with halogen, $(C_{1-4})$alkyl or $(C_{1-4})$alkoxy. Other suitable esters can be found in Design of Prodrugs, Bundgaard, H. Ed. Elsevier (1985). Such pharmaceutically acceptable esters are usually hydrolyzed in vivo when injected in a mammal and transformed into the acid form of the compound of formula I. With regard to the esters described above, unless otherwise specified, any alkyl moiety present advantageously contains 1 to 16 carbon atoms, particularly 1 to 6 carbon atoms. Any aryl moiety present in such esters advantageously comprises a phenyl group. In particular the esters may be a $(C_{1-16})$alkyl ester, an unsubstituted benzyl ester or a benzyl ester substituted with at least one halogen, $(C_{1-6})$alkyl, $(C_{1-6})$alkoxy, nitro or trifluoromethyl.

The term "salt thereof" means any acid and/or base addition salt of a compound according to the invention; preferably a pharmaceutically acceptable salt thereof.

As used herein, the term "pharmaceutically acceptable salt" means a salt of a compound which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. Where applicable and compatible with the chemical properties of the compound of formula (I), the term includes pharmaceutically-acceptable acid addition salts and pharmaceutically-acceptable base addition salts. Lists of suitable salts are found in, e.g., S. M. Birge et al., J. Pharm. Sci., 1977, 66, pp. 1-19.

The term "pharmaceutically-acceptable acid addition salt" means those salts which retain the biological effectiveness and properties of the free bases and which are not biologically or otherwise undesirable, formed with inorganic acids such as hydrochloric acid, hydrobromic acid, hydroiodic acid, sulfuric acid, sulfamic acid, nitric acid, phosphoric acid, and the like, and organic acids such as acetic acid, trichloroacetic acid, trifluoroacetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, heptanoic acid, hexanoic acid, formic acid, fumaric acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, salicylic acid, stearic acid, succinic acid, sulfanilic acid, tartaric acid, p-toluenesulfonic acid, undecanoic acid, and the like.

The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

As used herein, the term "treatment" means the administration of a compound or composition according to the present invention to alleviate or eliminate symptoms of the HIV disease and/or to reduce viral load in a patient. The term "treatment" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectible levels in the blood, and the administration of a compound or composition according to the present invention to prevent perinatal transmission of HIV-1 from mother to baby, by administration to the mother before giving birth and to the child within the first days of life.

The following sign 

is used in sub-formulas to indicate the bond which is connected to the rest of the molecule as defined.

DETAILED DESCRIPTION OF PREFERRED EMBODIMENTS

In the following preferred embodiments, groups and substituents of the compounds of formula (I) according to this invention are described in detail.

$R^1$ and $R^2$:

Preferably, $R^1$ and $R^2$ are each independently selected from H, halo, cyano, $(C_{1-4})$alkyl, $(C_{3-6})$cycloalkyl, —O—$(C_{1-4})$alkyl, —COO$(C_{1-4})$alkyl and —CONH$_2$; wherein said $(C_{1-4})$alkyl is optionally substituted with one, two or three halo substituents; and wherein said —O—$(C_{1-4})$alkyl is optionally substituted with —COO$(C_{1-4})$alkyl or one, two or three halo substituents;

with the proviso that when $R^1$ is H, $R^2$ cannot be H.

More preferably, $R^1$ and $R^2$ are each independently selected from H, fluoro, chloro, bromo, iodo, cyano, methyl, ethyl, propyl, 1-methylethyl, —CF$_3$, —OCH$_3$, —OCF$_3$, cyclopropyl, cyclobutyl, —CONH$_2$, —COOCH$_3$, —COOCH$_2$CH$_3$, —O—CH$_2$COOCH$_3$ and —O—CH$_2$COOCH$_2$CH$_3$;

with the proviso that when $R^1$ is H, $R^2$ cannot be H.

Even more preferably, $R^1$ and $R^2$ are each independently selected from H, fluoro, chloro, bromo, iodo, cyano, CF$_3$, —OCH$_3$, —OCF$_3$, —CONH$_2$, —O—CH$_2$COOCH$_3$ and cyclopropyl;

with the proviso that when $R^1$ is H, $R^2$ cannot be H.

Most preferably, $R^1$ and $R^2$ are each independently selected from H, fluoro, chloro, bromo, iodo, cyano, CF$_3$, and cyclopropyl;

with the proviso that when $R^1$ is H, $R^2$ cannot be H.

Any and each individual definition of $R^1$ and $R^2$ as set out herein may be combined with any and each individual definition of $R^3$, $R^4$, Q, $R^6$ and $R^7$ as set out herein.

$R^3$:

Preferably, $R^3$ is chloro or fluoro.

More preferably, $R^3$ is chloro.

Any and each individual definition of $R^3$ as set out herein may be combined with any and each individual definition of $R^1$, $R^2$, $R^4$, Q, $R^6$ and $R^7$ as set out herein.

$R^4$:

Preferably, $R^4$ is selected from chloro, nitro and methyl.

More preferably, $R^4$ is chloro or methyl.

Any and each individual definition of $R^4$ as set out herein may be combined with any and each individual definition of $R^1$, $R^2$, $R^3$, Q, $R^6$ and $R^7$ as set out herein.

Q:

In one embodiment, Q is N.

In an alternative embodiment, Q is $CR^5$, wherein $R^5$ is H or halo.

Preferably when Q is $CR^5$, $R^5$ is H or fluoro.

Any and each individual definition of Q as set out herein may be combined with any and each individual definition of $R^1$, $R^2$, $R^3$, $R^4$, $R^6$ and $R^7$ as set out herein.

$R^6$:

Preferably, $R^6$ is H or fluoro. Most preferably, $R^6$ is H.

Any and each individual definition of $R^6$ as set out herein may be combined with any and each individual definition of $R^1$, $R^2$, $R^3$, $R^4$, Q and $R^7$ as set out herein.

$R^7$:

In one embodiment, $R^7$ is a group of the formula

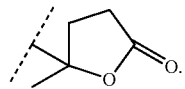

In an alternative embodiment, $R^7$ is —$(C_{1-6})$alkyl-$R^8$;
wherein the $(C_{1-6})$alkyl portion of said —$(C_{1-6})$alkyl-$R^8$ is optionally monosubstituted with —OH and optionally substituted with from one to six halo substituents; and wherein $R^8$ is as defined herein.

More preferably, $R^7$ is selected from —C(CH$_3$)$_2$—$R^8$, —C(CH$_3$)$_2$CH$_2$—$R^8$, —CH$_2$CH$_2$—$R^8$, —C(CH$_3$)(OH)—COOH and —C(CF$_3$)$_2$—OH, wherein $R^8$ is as defined herein.

Most preferably, $R^7$ is —C(CH$_3$)$_2$—$R^8$, wherein $R^8$ is as defined herein.

Preferably, $R^8$ is selected from a) —OH, —COOH, —C(═O)NHOH, —OC(═O)NH$_2$ or —NH$_2$;

b) —O—$(C_{2-3})$alkyl-OH, —NH—$(C_{2-3})$alkyl —OH, —O—$(C^{1-3})$alkyl-$R^{81}$ or —NH—$(C_{1-3})$alkyl -$R^{81}$, wherein $R^{81}$ is —COOH or a 6-membered saturated heterocycle containing one N heteroatom and optionally one additional heteroatom selected from N, O and S;

c) —NHC(═O)—$R^{82}$, wherein $R^{82}$ is selected from $(C_{1-4})$alkyl, $(C_{2-4})$alkenyl, $(C_{3-6})$cycloalkyl, phenyl and a 4-, 5- or 6-membered heterocycle which is saturated, unsaturated or aromatic and which contains one N heteroatom and optionally one additional heteroatom selected from N, O and S, wherein each said N heteroatom may, independently and where possible, exist in an oxidized state such that it is further bonded to an oxygen atom to form an N-oxide group;

each of said $(C_{1-4})$alkyl, $(C_{2-4})$alkenyl, $(C_{3-6})$cycloalkyl, phenyl and 4-, 5- or 6-membered heterocycle being optionally substituted with one or more substituents each independently selected from —OH, —COOH, —SO$_2$NH$_2$, —NH$_2$, —NH(C$_{1-3}$)alkyl, —N((C$_{1-3}$)alkyl)$_2$, —NH(C$_{1-3}$)alkyl-O(C$_{1-3}$)alkyl, —NH—(C$_{1-3}$)alkyl-COOH, —NHHet and Het;

wherein said Het is a 6-membered saturated heterocycle containing one N heteroatom and optionally one additional heteroatom selected from N, O and S, which is optionally substituted with —COOH; and wherein the Het portion of said —NHHet is a 6-membered aromatic heterocycle containing one N heteroatom wherein said N heteroatom optionally exists in an oxidized state such that it is further bonded to an oxygen atom to form an N-oxide group; and d) —C(=O)N(R$^{83}$)R$^{84}$, wherein R$^{83}$ is selected from H and CH$_3$; and R$^{84}$ is selected from $(C_{1-4})$alkyl and a 6-membered saturated heterocycle containing one N heteroatom and optionally one additional heteroatom selected from N, O and S;

wherein said $(C_{1-4})$alkyl is optionally substituted with one or more substituents each independently selected from —OH, —COOH and —SO$_3$H;

or R$^{83}$ and R$^{84}$ are linked, together with the nitrogen atom to which they are bonded, to form a 6-membered monocyclic saturated heterocycle which optionally contains one or two additional heteroatoms each independently selected from N, O and S; said heterocycle being optionally substituted with —COOH.

More preferably, R$^8$ is selected from a) —OH, —COOH, —C(=O)NHOH, —OC(=O)NH$_2$ or —NH$_2$;

b) —O—CH$_2$—R$^{81}$, —O—CH$_2$CH$_2$—OH, —O—CH$_2$CH$_2$—R$^{81}$ or —NH—CH$_2$—R$^{81}$, wherein R$^{81}$ is —COOH or

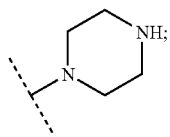

c) —NHC(=O)—R$^{82}$, wherein R$^{82}$ is selected from methyl, ethyl, propyl, 1-methylethyl, butyl, 1-methylpropyl, 2-methylpropyl, 1,1-dimethylethyl, ethenyl, cyclopropyl, cyclobutyl, phenyl,

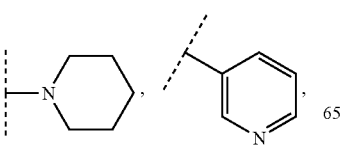

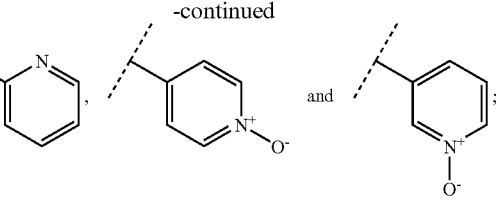

each of said groups being optionally substituted with one or two substituents each independently selected from —OH, —COOH, —SO$_2$NH$_2$, —NH$_2$, —NHCH$_3$, —N(CH$_3$)$_2$, —NH(CH$_2$)$_2$OMe, —NHCH$_2$COOH,

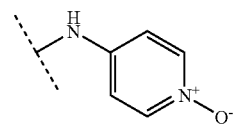

and Het;

wherein said Het is selected from

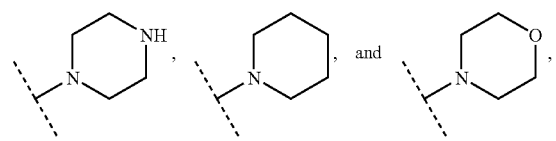

each of which being optionally substituted with —COOH; and d) —C(=O)N(R$^{83}$)R$^{84}$, wherein R$^{83}$ is selected from H and CH$_3$; and R$^{84}$ is selected from methyl, ethyl, propyl, 1-methylethyl and

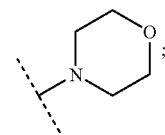

each of said methyl, ethyl, propyl and 1-methylethyl being optionally substituted with one or two substituents each independently selected from —OH, —COOH and —SO$_3$H;

or R$^{83}$ and R$^{84}$ are linked, together with the nitrogen atom to which they are bonded, to form a 6-membered monocyclic saturated heterocycle; said heterocycle being optionally substituted with —COOH.

Even more preferably, R$^8$ is selected from —OH, —COOH, —CO—NHOH, —OC(=O)NH$_2$, —NH$_2$, —O—CH$_2$CH$_2$OH,

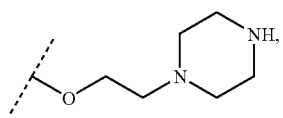

—OCH₂—COOH, —NHCH₂—COOH, —NH—CO-Me, —NH—CO—CH₂OH, —NH—CO—CH₂NH₂, —NH—CO—CH₂—NHMe, —NH—CO—CH₂—N(Me)₂, —NHCOCH₂NH(CH₂)₂OMe, —NHCOCH₂NHCH₂COOH, —NH—COCH(Me)-NH₂, —NH—COC(Me)₂—NH₂, —NH—CO—CH₂CO₂H, —NH—CO—CHMeCO₂H, —NH—COCH(Et)CO₂H, —NH—CO—C(Me)₂CO₂H, —NH—CO—(CH₂)₂CO₂H, —NH—CO—CH(Me)CH₂CO₂H, —NH—CO—CH₂CH(Me)CO₂H, —NH—CO—C(Me)₂CH₂CO₂H, —NH—CO—CH₂C(Me)₂CO₂H,

—NH—CO—(CH₂)₃—SO₂NH₂,

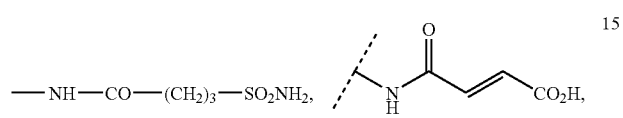

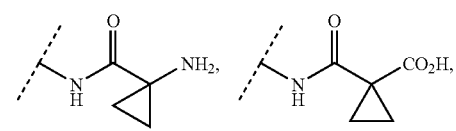

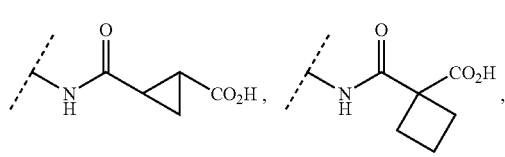

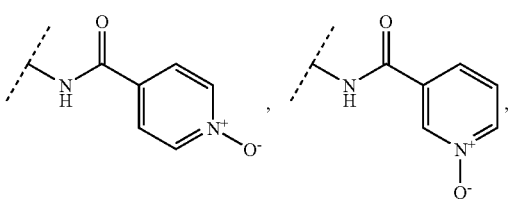

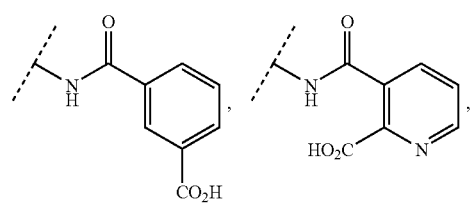

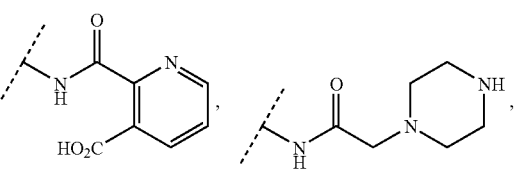

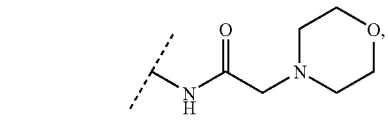

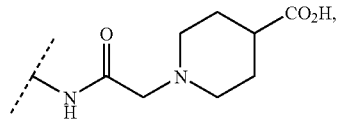

-continued

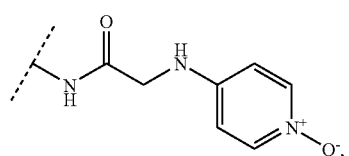

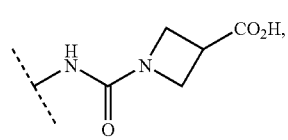

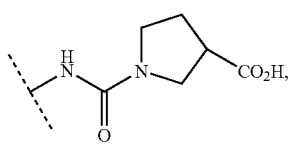

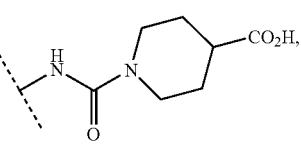

—CO—N(Me)—CH₂CO₂H, —CONHCH₂CO₂H,

—CONHCH(Me)CO₂H, —CONHC(Me)₂CO₂H,

—CONH(CH₂)₂SO₃H,

and

Still more preferably, R⁸ is selected from —OH, —COOH, —NH₂, —OCH₂—COOH, —NHCH₂—COOH, —NH—CO-Me, —NH—CO—CH₂OH, —NH—CO—CH₂NH₂, —NH—CO—CH₂—NHMe, —NH—CO—CH₂—N(Me)₂, —NH—COCH₂NH(CH₂)₂OMe, —NH—COC(Me)₂—NH₂, —NH—CO—(CH₂)₂CO₂H, —NH—CO—CH(Me)CH₂CO₂H, —NH—CO—CH₂CH(Me)CO₂H, —NH—CO—

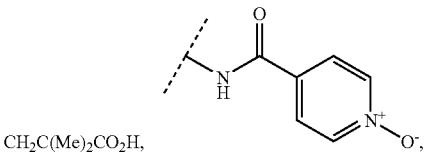

CH₂C(Me)₂CO₂H,

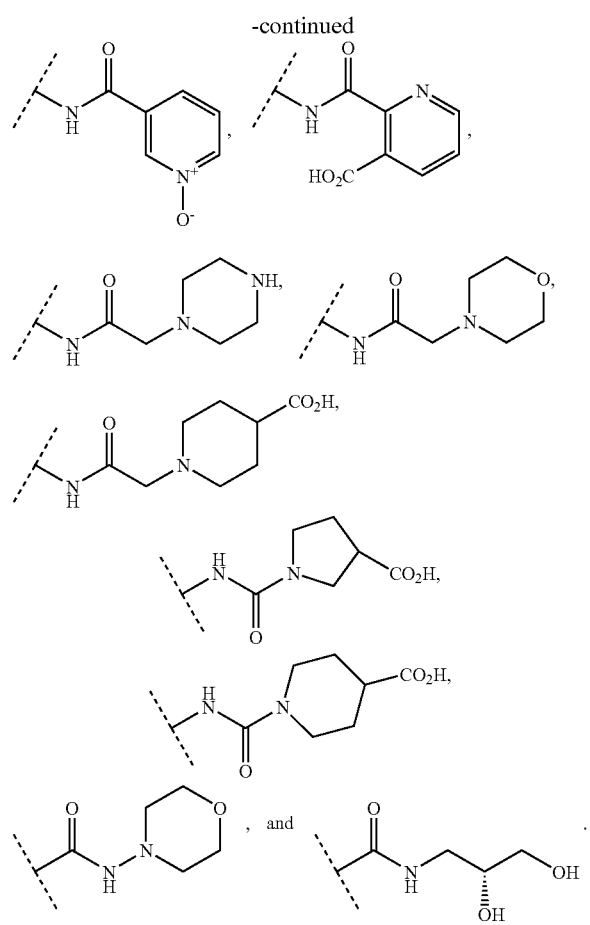

Any and each individual definition of $R^7$ as set out herein may be combined with any and each individual definition of $R^1$, $R^2$, $R^3$, $R^4$, Q and $R^6$ as set out herein.

Therefore, a preferred embodiment of a first aspect of the invention provides a compound of formula (I) wherein $R^1$ and $R^2$ are each independently selected from H, fluoro, chloro, bromo, iodo, cyano, methyl, ethyl, propyl, 1-methylethyl, —$CF_3$, —$OCH_3$, —$OCF_3$, cyclopropyl, cyclobutyl, —$CONH_2$, —$COOCH_3$, —$COOCH_2CH_3$, —O—$CH_2COOCH_3$ and —O—$CH_2COOCH_2CH_3$;

with the proviso that when $R^1$ is H, $R^2$ cannot be H;

$R^3$ is chloro or fluoro;

$R^4$ is selected from chloro, nitro and methyl;

Q is N or $CR^5$, wherein $R^5$ is H or halo;

$R^6$ is H or fluoro; and $R^7$ is a group of the formula

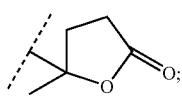

or $R^7$ is —$(C_{1-6})$alkyl-$R^8$;

wherein the $(C_{1-6})$alkyl portion of said —$(C_{1-6})$alkyl-$R^8$ is optionally monosubstituted with —OH and optionally substituted with from one to six halo substituents; and wherein $R^8$ is selected from:

a) —OH, —COOH, —C(=O)NHOH, —OC(=O)$NH_2$ or —$NH_2$;

b) —O—$(C_{2-3})$alkyl-OH, —NH—$(C_{2-3})$alkyl —OH, —O—$(C^{1-3})$alkyl-$R^{81}$ or —NH—$(C_{1-3})$alkyl-$R^{81}$, wherein $R^{81}$ is —COOH or a 6-membered saturated heterocycle containing one N heteroatom and optionally one additional heteroatom selected from N, O and S;

c) —NHC(=O)—$R^{82}$, wherein $R^{82}$ is selected from $(C_{1-4})$alkyl, $(C_{2-4})$alkenyl, (Cm)cycloalkyl, phenyl and a 4-, 5- or 6-membered heterocycle which is saturated, unsaturated or aromatic and which contains one N heteroatom and optionally one additional heteroatom selected from N, O and S, wherein each said N heteroatom may, independently and where possible, exist in an oxidized state such that it is further bonded to an oxygen atom to form an N-oxide group;

each of said $(C_{1-4})$alkyl, $(C_{2-4})$alkenyl, $(C_{3-6})$cycloalkyl, phenyl and 4-, 5- or 6-membered heterocycle being optionally substituted with one or more substituents each independently selected from —OH, —COOH, —$SO_2NH_2$, —$NH_2$, —NH$(C_{1-3})$alkyl, —N($(C_{1-3})$alkyl)$_2$, —NH—$(C_{1-3})$alkyl-O$(C_{1-3})$alkyl, —NH—$(C_{1-3})$alkyl-COOH, —NHHet and Het;

wherein said Het is a 6-membered saturated heterocycle containing one N heteroatom and optionally one additional heteroatom selected from N, O and S, which is optionally substituted with —COOH; and wherein the Het portion of said —NHHet is a 6-membered aromatic heterocycle containing one N heteroatom wherein said N heteroatom optionally exists in an oxidized state such that it is further bonded to an oxygen atom to form an N-oxide group; and d) —C(=O)N($R^{83}$)$R^{84}$, wherein $R^{83}$ is selected from H and $CH_3$; and $R^{84}$ is selected from $(C_{1-4})$alkyl and a 6-membered saturated heterocycle containing one N heteroatom and optionally one additional heteroatom selected from N, O and S;

wherein said $(C_{1-4})$alkyl is optionally substituted with one or more substituents each independently selected from —OH, —COOH and —$SO_3H$;

or $R^{83}$ and $R^{84}$ are linked, together with the nitrogen atom to which they are bonded, to form a 6-membered monocyclic saturated heterocycle which optionally contains one or two additional heteroatoms each independently selected from N, O and S; said heterocycle being optionally substituted with —COOH.

More preferably, a compound of formula (I) is provided wherein $R^1$ and $R^2$ are each independently selected from H, fluoro, chloro, bromo, iodo, cyano, $CF_3$, —$OCH_3$, —$OCF_3$, —$CONH_2$, —O—$CH_2COOCH_3$ and cyclopropyl;

with the proviso that when $R^1$ is H, $R^2$ cannot be H;

$R^3$ is chloro;

$R^4$ is chloro or methyl;

Q is $CR^5$, wherein $R^5$ is H or halo;

$R^6$ is H; and $R^7$ is a group of the formula

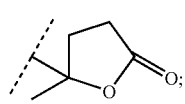

or $R^7$ is selected from —C(CH$_3$)$_2$—R$^8$, —C(CH$_3$)$_2$CH$_2$—R$^8$, —CH$_2$CH$_2$—R$^8$, —C(CH$_3$)(OH)—COOH and —C(CF$_3$)$_2$—OH, wherein $R^8$ is selected from a) —OH, —COOH, —C(=O)NHOH, —OC(=O)NH$_2$ or —NH$_2$;

b) —O—CH$_2$—R$^{81}$, —O—CH$_2$CH$_2$—OH, —O—CH$_2$CH$_2$—R$^{81}$ or —NH—CH$_2$—R$^{81}$, wherein $R^{81}$ is —COOH or

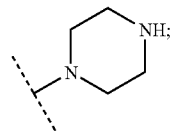

c) —NHC(=O)—R$^{82}$, wherein $R^{82}$ is selected from methyl, ethyl, propyl, 1-methylethyl, butyl, 1-methylpropyl, 2-methylpropyl, 1,1-dimethylethyl, ethenyl, cyclopropyl, cyclobutyl, phenyl,

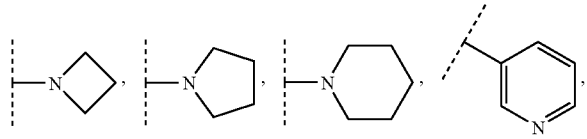

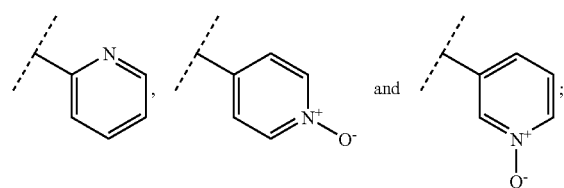

each of said groups being optionally substituted with one or two substituents each independently selected from —OH, —COOH, —SO$_2$NH$_2$, —NH$_2$, —NHCH$_3$, —N(CH$_3$)$_2$, —NH(CH$_2$)$_2$OMe, —NHCH$_2$COOH,

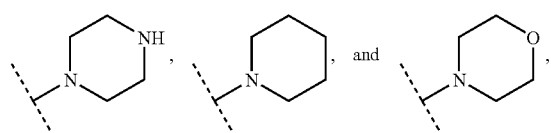

and Het;
wherein said Het is selected from

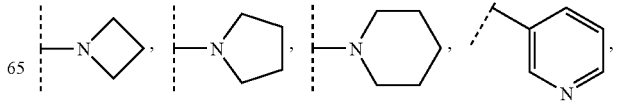

each of which being optionally substituted with —COOH; and d) —C(=O)N(R$^{83}$)R$^{84}$, wherein $R^{83}$ is selected from H and CH$_3$; and $R^{84}$ is selected from methyl, ethyl, propyl, 1-methylethyl and

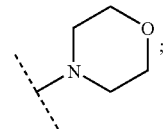

each of said methyl, ethyl, propyl and 1-methylethyl being optionally substituted with one or two substituents each independently selected from —OH, —COOH and —SO$_3$H;

or $R^{83}$ and $R^{84}$ are linked, together with the nitrogen atom to which they are bonded, to form a 6-membered monocyclic saturated heterocycle; said heterocycle being optionally substituted with —COOH.

Most preferably, a compound of formula (I) is provided wherein $R^1$ and $R^2$ are each independently selected from H, fluoro, chloro, bromo, iodo, cyano, CF$_3$, and cyclopropyl; with the proviso that when $R^1$ is H, $R^2$ cannot be H;

$R^3$ is chloro;

$R^4$ is chloro or methyl;

Q is CR$^5$ wherein $R^5$ is H or fluoro;

$R^6$ is H; and $R^7$ is a group of the formula

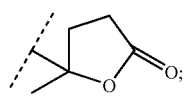

or $R^7$ is —C(CH$_3$)$_2$—R$^8$ wherein $R^8$ is selected from a) —OH, —COOH, —C(=O)NHOH, —OC(=O)NH$_2$ or —NH$_2$;

b) —O—CH$_2$—R$^{81}$, —O—CH$_2$CH$_2$—OH, —O—CH$_2$CH$_2$—R$^{81}$ or —NH—CH$_2$—R$^{81}$, $R^{81}$ is —COOH or

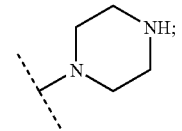

c) —NHC(=O)—R$^{82}$, wherein $R^{82}$ is selected from methyl, ethyl, propyl, 1-methylethyl, butyl, 1-methylpropyl, 2-methylpropyl, 1,1-dimethylethyl, ethenyl, cyclopropyl, cyclobutyl, phenyl, -continued

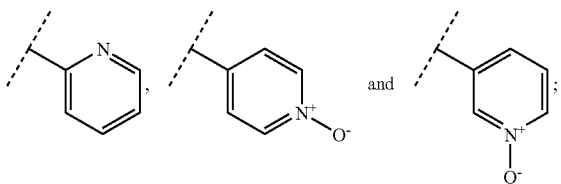

each of said groups being optionally substituted with one or two substituents each independently selected from —OH, —COOH, —SO₂NH₂, —NH₂, —NHCH₃, —N(CH₃)₂, —NH(CH₂)₂OMe, —NHCH₂COOH,

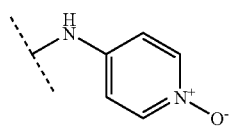

and Het;
wherein said Het is selected from

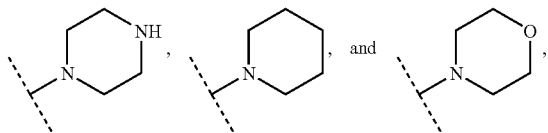

each of which being optionally substituted with —COOH; and d) —C(=O)N(R⁸³)R⁸⁴, wherein R⁸³ is selected from H and CH₃; and R⁸⁴ is selected from methyl, ethyl, propyl, 1-methylethyl and

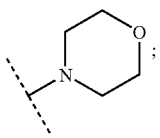

each of said methyl, ethyl, propyl and 1-methylethyl being optionally substituted with one or two substituents each independently selected from —OH, —COOH and —SO₃H;

or R⁸³ and R⁸⁴ are linked, together with the nitrogen atom to which they are bonded, to form a 6-membered monocyclic saturated heterocycle; said heterocycle being optionally substituted with —COOH.

SPECIFIC EMBODIMENTS

Included within the scope of this invention are all compounds of formula (I) as presented in Tables 1 and 2.

In general, all tautomeric and isomeric forms and mixtures thereof, for example, individual geometric isomers, stereoisomers, enantiomers, diastereomers, racemates, racemic or non-racemic mixtures of stereoisomers, mixtures of diastereomers, or mixtures of any of the foregoing forms of a chemical structure or compound is intended, unless the specific stereochemistry or isomeric form is specifically indicated in the compound name or structure.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the present invention from this disclosure and the knowledge in the art.

Preparation of pure stereoisomers, e.g. enantiomers and diastereomers, or mixtures of desired enantiomeric excess (ee) or enantiomeric purity, are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, for example, GC, HPLC, CE, or NMR, and assignment of absolute configuration and conformation, for example, CD ORD, X-ray crystallography, or NMR.

The compounds of formula (I) are effective inhibitors of wild type HIV as well as of the double mutant enzyme K103N/Y181C. The compounds of the invention may also inhibit the single mutant enzymes V106A, Y188L, K103N, Y181C, P236L and G190A (among others). The compounds may also inhibit other double mutant enzymes including K103N/P225H, K103N/V108I and K103N/L100I.

The compounds of formula (I) possess inhibitory activity against HIV-1 replication. When administered in suitable dosage forms, they are useful in the treatment of AIDS, ARC and related disorders associated with HIV-1 infection. Another aspect of the invention, therefore, is a method for treating HIV-1 infection which comprises administering, to a human infected by HIV-1, a therapeutically effective amount of a compound of formula (I), as described above. The compounds may also be administered, as a treatment or prophylactic measure, after an individual has been exposed to HIV-1 but before the appearance of symptoms of the disease, and/or prior to the detection of the virus in the blood, to prevent the appearance of symptoms of the disease and/or to prevent the virus from reaching detectible levels in the blood. Whether it is termed treatment or prophylaxis, the compounds may also be used to prevent perinatal transmission of HIV-1 from mother to baby, by administration to the mother before giving birth and to the child within the first days of life.

The compounds of formula (I) may be administered in single or divided doses by the oral, parenteral or topical routes. A suitable oral dosage for a compound of formula (I) would be in the range of about 0.5 mg to 3 g per day. A preferred oral dosage for a compound of formula (I) would be in the range of about 100 mg to 800 mg per day for a patient weighing 70 kg. In parenteral formulations, a suitable dosage unit may contain from 0.1 to 250 mg of said compounds, preferably 1 mg to 200 mg, whereas for topical administration, formulations containing 0.01 to 1% active ingredient are preferred. It should be understood, however, that the dosage administration from patient to patient would vary. The dosage for any particular patient will depend upon the clinician's judgment, who will use as criteria for fixing a proper dosage the size and condition of the patient as well as the patient's response to the drug.

When the compounds of the present invention are to be administered by the oral route, they may be administered as medicaments in the form of pharmaceutical preparations that contain them in association with a compatible pharmaceutical carrier material. Such carrier material can be an inert organic or inorganic carrier material suitable for oral administration. Examples of such carrier materials include but are not limited to water, gelatin, talc, starch, magnesium stearate, gum arabic, vegetable oils, polyalkylene-glycols, petroleum jelly and the like.

The compounds of formula (I) can be used in combination with one or more other antiretroviral agent known to one skilled in the art, as a combined preparation useful for simultaneous, separate or sequential administration for treating or preventing HIV infection in an individual. Examples of antiretroviral agents, including approved and investigational drugs, that may be used in combination therapy with compounds of formula (I) include but are not limited to:

NRTIs (nucleoside or nucleotide reverse transcriptase inhibitors; including but not limited to zidovudine, didanosine, zalcitabine, stavudine, lamivudine, emtricitabine, abacavir, and tenofovir);

NNRTIs (non-nucleoside reverse transcriptase inhibitors; including but not limited to nevirapine, delavirdine, efavirenz, capravirine, etravirine, rilpivirine, GW695634 and BILR 355);

protease inhibitors (including but not limited to ritonavir, tipranavir, saquinavir, nelfinavir, indinavir, amprenavir, fosamprenavir, atazanavir, lopinavir, VX-385 and TMC-114);

entry inhibitors including but not limited to CCR5 antagonists (including but not limited to maraviroc (UK-427, 857), SCH-417690, GW873140 and TAK-652), CXCR4 antagonists (including but not limited to AMD-11070), fusion inhibitors (including but not limited to enfuvirtide (T-20)) and others (including but not limited to PRO-542 and BMS-488043);

integrase inhibitors (including but not limited to c-1605, BMS-538158 and JTK-303);

TAT inhibitors;

maturation inhibitors (including but not limited to PA-457);

immunomodulating agents (including but not limited to levamisole); and antifungal or antibacterial agents (including but not limited to fluconazole).

Moreover, a compound of formula (I) can be used with at least one other compound of formula (I).

The pharmaceutical preparations can be prepared in a conventional manner and finished dosage forms can be solid dosage forms including but not limited to tablets, dragees, capsules, and the like, or liquid dosage forms including but not limited to solutions, suspensions, emulsions and the like. The pharmaceutical preparations may be subjected to conventional pharmaceutical operations including but not limited to sterilization. Further, the pharmaceutical preparations may contain conventional adjuvants including but not limited to preservatives, stabilizers, emulsifiers, flavor-improvers, wetting agents, buffers, salts for varying the osmotic pressure and the like. Solid carrier material which can be used include but is not limited to starch, lactose, mannitol, methyl cellulose, microcrystalline cellulose, talc, silica, dibasic calcium phosphate, and high molecular weight polymers (such as polyethylene glycol).

For parenteral use, a compound of formula (I) can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include but are not limited to, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as a solution for nasal application and may contain in addition to the compounds of this invention suitable buffers, tonicity adjusters, microbial preservatives, antioxidants and viscosity-increasing agents in an aqueous vehicle. Examples of agents used to increase viscosity include but are not limited to polyvinyl alcohol, cellulose derivatives, polyvinylpyrrolidone, polysorbates or glycerin. Microbial preservatives added may include but are not limited to benzalkonium chloride, thimerosal, chloro-butanol or phenylethyl alcohol.

Additionally, the compounds provided by the invention may be administerable by suppository.

Methodology and Synthesis

In general, the compounds of formula (I) are prepared by known methods from readily available starting materials, using reaction conditions known to be suitable for the reactants. Schemes 1 to 4 illustrate the general methods used to prepare the compounds of formula (I), wherein $X^1$ is bromo or iodo, $X^2$ is chloro or bromo, P is a protecting group, $R^1$, $R^2$, $R^3$, $R^4$, Q, $R^6$ and $R^7$ are as defined herein and $R^{7a}$ is a protected form of $R^7$.

Scheme 1: General method for the synthesis of benzophenone intermediates

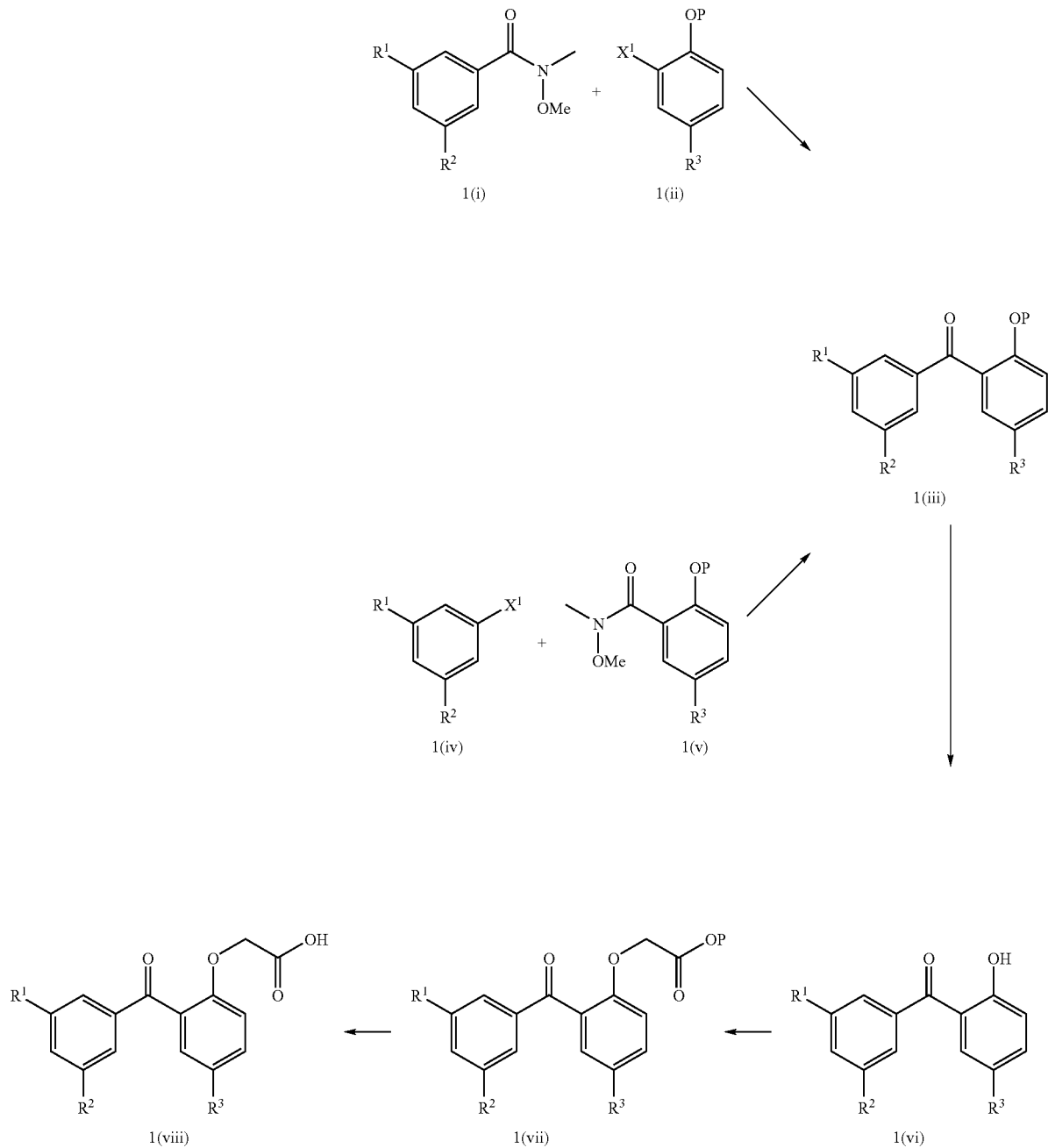

In general, the benzophenone intermediates 1(viii) were prepared by the method of J. H. Chan et al. (J. Med. Chem. 2004, 47, 1175-1182) or modifications thereof. Briefly, the aryllithium obtained by halogen-lithium exchange from 1(ii) can be acylated with amide 1(i) to give benzophenone 1(iii). Other organometallic derivatives can also be used to acylate amide 1(i). Alternatively, benzophenone 1(iii) can also be obtained upon acylation of the aryllithium or other organometallic derivative derived from 1(iv) with amide 1(v). Cleavage of the protecting group of benzophenone 1(iii) gives the hydroxybenzophenone 1(vi) that can be O-alkylated with α-haloacetic acid ester in the presence of base to yield the corresponding ether 1(vii). $R^1$ and $R^2$ substituents (e.g. Br) of intermediate 1(iii) or 1(vii) can also be converted to other $R^1$ and $R^2$ substituents (e.g. CN, cPr for 1(iii); OMe for 1(vii)) using methods known to one skilled in the art. Cleavage of the ester protecting group of 1(vii) gives acid 1(viii). Alternatively, hydroxybenzophenone 1(vi) may be transformed directly into acid 1(viii) by alkylation with an α-haloacetic acid.

Scheme 2: Synthesis of substituted anilines

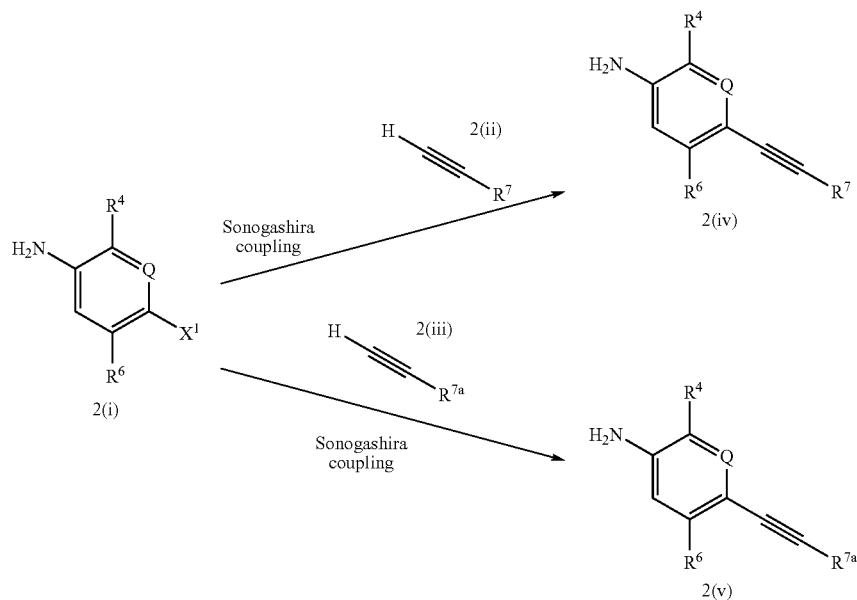

Briefly, the coupling of 4-bromo- or 4-iodoaniline 2(i) with alkynes 2(ii) and 2(iii) under basic conditions in the presence of a palladium catalyst and a copper(I) salt, using the typical conditions of the Sonogashira reaction, well known to one skilled in the art, gives anilines 2(iv) and 2(v), in which the $R^7$ group may be free or in a protected form ($R^{7a}$), respectively.

Scheme 3: General methods for the synthesis of compounds of formula (I)

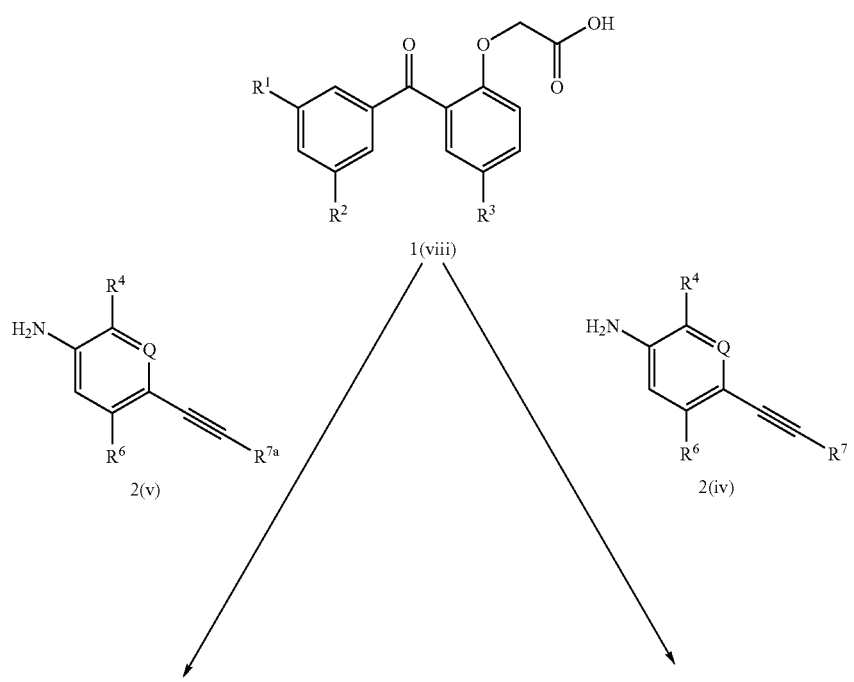

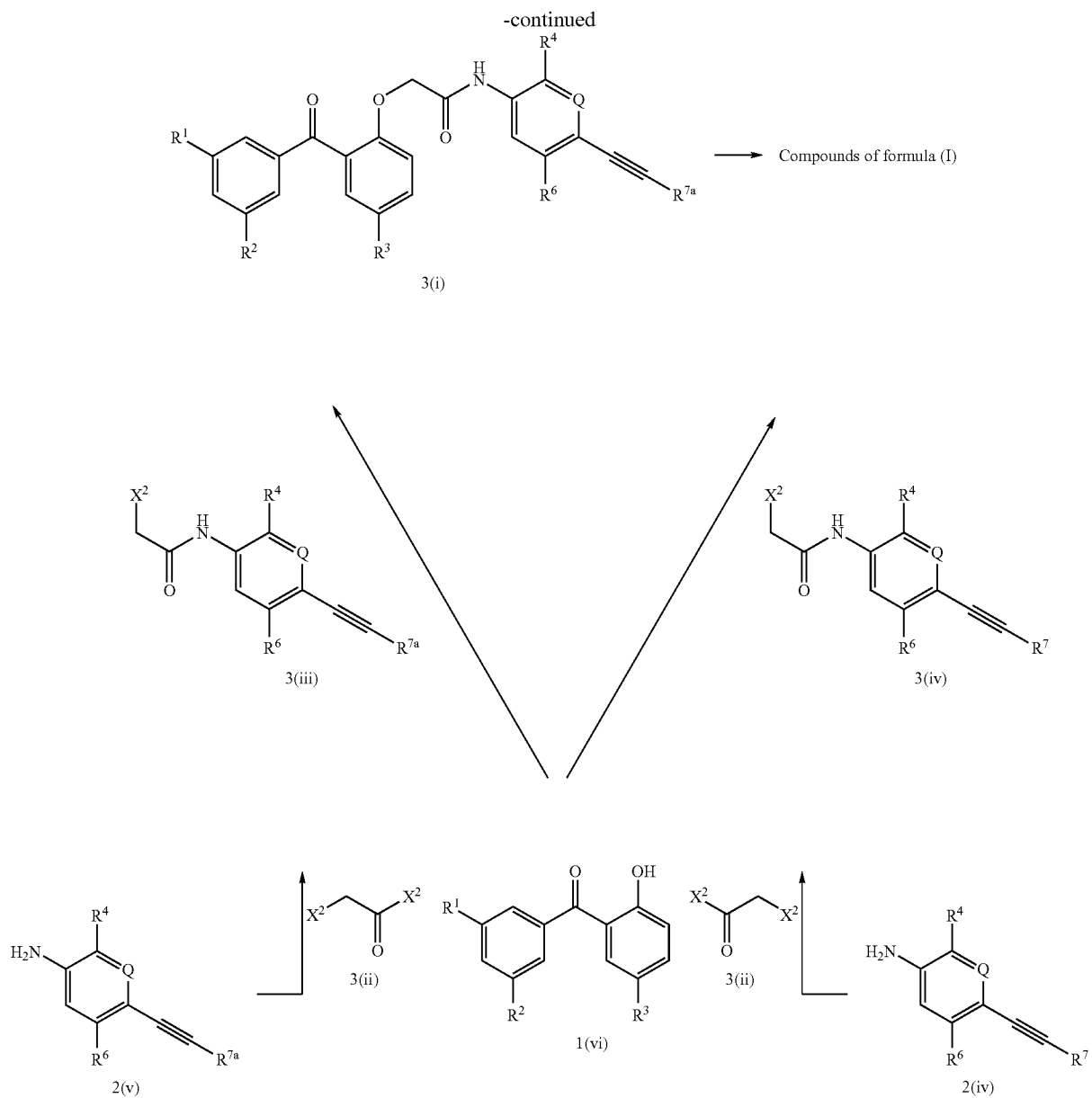

Briefly, the coupling of acid 1(viii) with aniline 2(v) using proper activation of the acid (e.g. acyl chloride) gives amide 3(i), which can be easily converted to compounds of formula (I) by deprotection of $R^{7a}$ to give $R^7$. The coupling of acid 1(viii) with aniline 2(iv) gives directly the compounds of formula (I). Alternatively, the O-alkylation of phenol 1(vi) with α-haloacetamide 3(iii), readily available from the coupling of aniline 2(v) and α-haloacetyl halide 3(ii) in the presence of a base, can also produce amide 3(i). Similarly, the O-alkylation of phenol 1(vi) with α-haloacetamide 3(iv), prepared from 2(iv) and 3(ii), gives directly the compounds of formula (I).

The $R^7$ substituents of compounds of formula (I) can also be transformed to provide compounds of formula (I) bearing other $R^7$ substituents using methods known to one skilled in the art (e.g. alkylation, acylation, substitution, oxidation and other functional group modifications). For example, compounds of formula (I) wherein $R^7$ is —$(C_{1-6})$alkyl-$R^8$, and $R^8$ is —$NH_2$ may be transformed into compounds of formula (I) wherein $R^7$ is —$(C_{1-6})$alkyl-$R^8$, and $R^8$ is —NHC(=O)—$R^{82}$ through well known coupling reactions with appropriate acylating reagents capable of transferring the —C(=O)—$R^{82}$ group. As another example, compounds of formula (I) wherein $R^7$ is —$(C_{1-6})$alkyl-$R^8$, and $R^8$ is —COOH may be transformed into compounds of formula (I) wherein $R^7$ is —$(C_{1-6})$alkyl-$R^8$, and $R^8$ is —C(=O)N($R^{83}$)$R^{84}$, through well-known coupling reactions between the $R^8$ carboxyl group and an amine of the formula HN($R^{83}$)$R^{84}$. As well, compounds of formula (I) wherein $R^7$ is —$(C_{1-6})$alkyl-$R^8$, and $R^8$ is —$NH_2$ or —OH may be transformed into compounds of formula (I) wherein $R^7$ is —$(C_{1-6})$alkyl-$R^8$, and $R^8$ is —NH—$(C_{1-6})$alkyl-$R^{81}$ or —O—$(C^{1-6})$alkyl-$R^{81}$ through the use of well known reactions.

Scheme 4: Alternative method for the synthesis of compounds of formula (I)

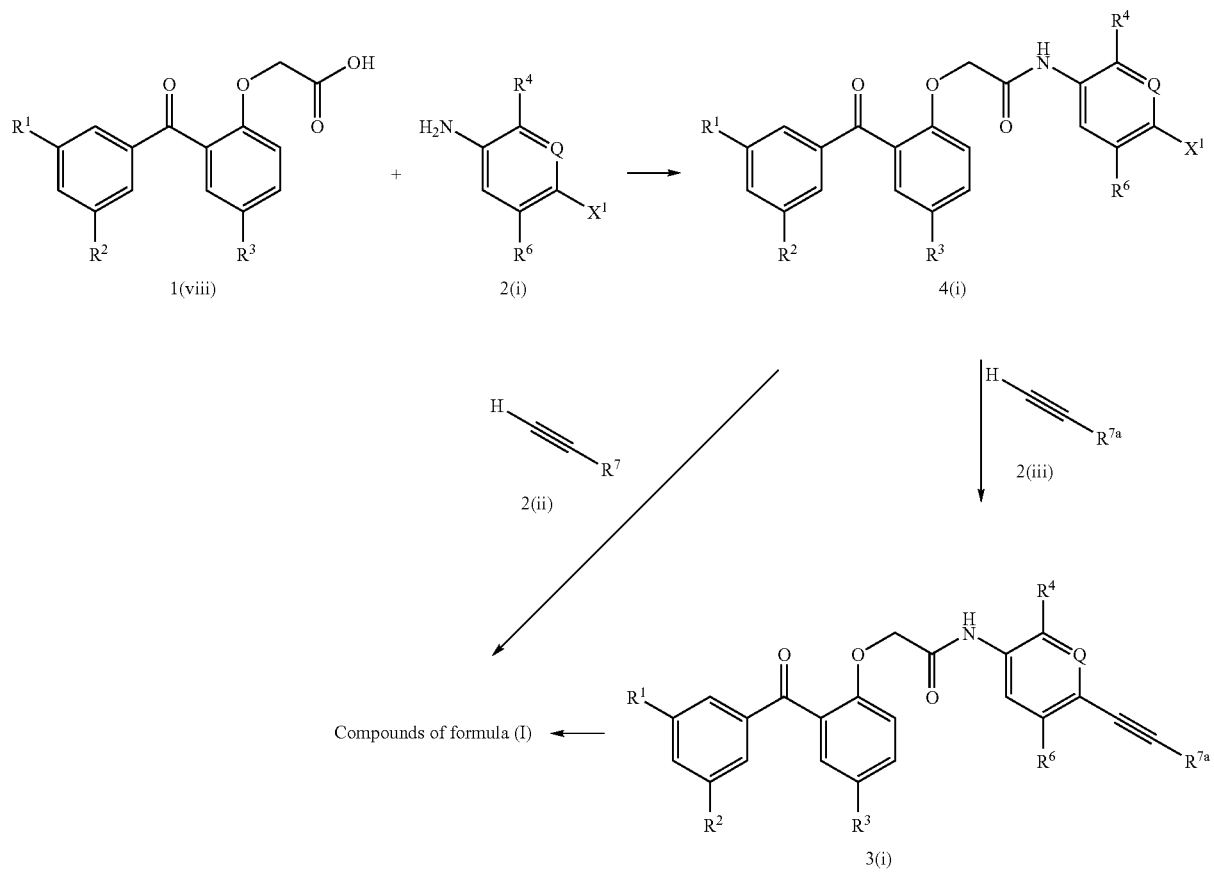

The modification of the sequence of reactions described in Schemes 2 and 3 as shown in Scheme 4 above illustrates an alternative method for the synthesis of the compounds of formula (I). Briefly, the coupling of acid 1(viii) with 4-bromo- or 4-iodoaniline 2(i) gives amide 4(i). The coupling of 4(i) with alkynes 2(iii) using the conditions of the Sonogashira reaction affords 3(i), which can be easily transformed to the compounds of formula (I) by removal of the protecting group present in substituent $R^{7a}$. The coupling of 4(i) with alkynes 2(ii) gives directly the compounds of formula (I).

EXAMPLES

The present invention is illustrated in further detail by the following non-limiting examples. All reactions were performed in a nitrogen or argon atmosphere unless otherwise stated. Room temperature is 18° to 22° C. (degrees Celsius). Solution percentages or ratios express a volume to volume relationship, unless stated otherwise. Purification by reverse phase HPLC (RP-HPLC) was performed using a gradient of MeCN/H$_2$O containing TFA (0.06%) (CombiPrep ODS-AQ 50×20 mm, 5μ, 120 Å). Analytical HPLC was carried out under standard conditions using a Combiscreen ODS-AQ C18 reverse phase column, YMC, 50×4.6 mm i.d., 5 μM, 120 Å at 220 nM, elution with a linear gradient as described in the following table (Solvent A is 0.06% TFA in H$_2$O; solvent B is 0.06% TFA in CH$_3$CN):

| Time (min) | Flow (mL/min) | Solvent A (%) | Solvent B (%) |
|---|---|---|---|
| 0 | 3.0 | 95 | 5 |
| 0.5 | 3.0 | 95 | 5 |
| 6.0 | 3.0 | 50 | 50 |
| 10.5 | 3.5 | 0 | 100 |

Abbreviations or symbols used herein include:
Ac: acetyl;
Boc: tert-butoxycarbonyl;
Bu: butyl;
tBu: 1,1-dimethylethyl (tert-butyl);
tBuOH: tert-butanol;
cPr: cyclopropyl;
CHAPS: 3-{(3-cholamidopropyl)dimethylammonio}-1-propanesulfonate;
DCC: 1,3-dicyclohexylcarbodiimide;
DEAD: diethyl azodicarboxylate;
DMF: N,N-dimethylformamide;
DMAP: 4-dimethylaminopyridine;
DMSO: dimethylsulfoxide;
dppf: 1,1'-bis(diphenylphosphino)ferrocene;
DTT: DL-dithiothreitol;
Et: ethyl;
Et$_2$O: diethyl ether;
EtOH: ethanol;

EtOAc: ethyl acetate;
GSH: glutathione;
HPLC: high performance liquid chromatography;
iPr: 1-methylethyl (isopropyl);
LiHMDS: lithium hexamethyldisilazide;
Me: methyl;
MeOH: methanol;
MeCN: acetonitrile;
NaHMDS: sodium hexamethyldisilazide;
NBS: n-bromosuccinimide;
n-BuLi: n-butyllithium;
NMR: nuclear magnetic resonance;
Ph: phenyl;
Pr: propyl;
RP-HPLC: reverse phase high performance liquid chromatography;
TBAF: tetrabutylammonium fluoride;
TBTU: O-benzotriazol-1-yl-N,N,N',N'-tetramethyluronium tetrafluoroborate;
TFA: trifluoroacetic acid;
THF: tetrahydrofuran;
TLC: thin layer chromatography.

Syntheses

The following examples illustrate methods for preparing compounds of the invention.

Example 1

Benzophenone Intermediate 1.7 a) Compound 1.2

36 N $H_2SO_4$ (1.5 mL) and NBS (2.75 g, 15.0 mmol) were added to a solution of acid 1.1 (1.90 g, 10.0 mmol) in TFA (5 mL) at room temperature. After stirring for 30 min the reaction mixture was poured into water (200 mL) with vigorous stirring. The suspension was filtered and the resulting solid was rinsed with water and dried to give compound 1.2 (2.45 g, 90% yield).

b) Compound 1.3

To a solution of the acid 1.2 (2.45 g, 9.11 mmol) in $CH_2Cl_2$ (35 mL) were added $(COCl)_2$ (0.87 mL, 10.0 mmol) and DMF (2 drops). After 2 h the reaction mixture was concentrated under reduced pressure. Pyridine (1.78 mL, 22.0 mmol) and MeNH(OMe).HCl (1.02 g, 10.5 mmol) were added to a solution of the acyl chloride in THF (20 mL) and the resulting solution was stirred at room temperature for 16 h. The reaction mixture was diluted with EtOAc and successively washed with aqueous 1 N HCl solution, aqueous saturated $NaHCO_3$ solution and brine, dried ($MgSO_4$), filtered and concentrated under reduced pressure to give compound 1.3 (2.23 g, 78% yield) as a colorless gum.

c) Compound 1.5

A solution of 2.5 M n-BuLi in hexane (3.36 mL, 8.40 mmol) was added over 15 min to a solution of compound 1.4 (1.90 g, 8.50 mmol) in $Et_2O$ (25 mL) at −78° C. The reaction mixture was stirred at −78° C. for an additional 30 min, then a solution of compound 1.3 (2.50 g, 8.01 mmol) in $Et_2O$ (10 mL) was added over 20 min. The resulting mixture was

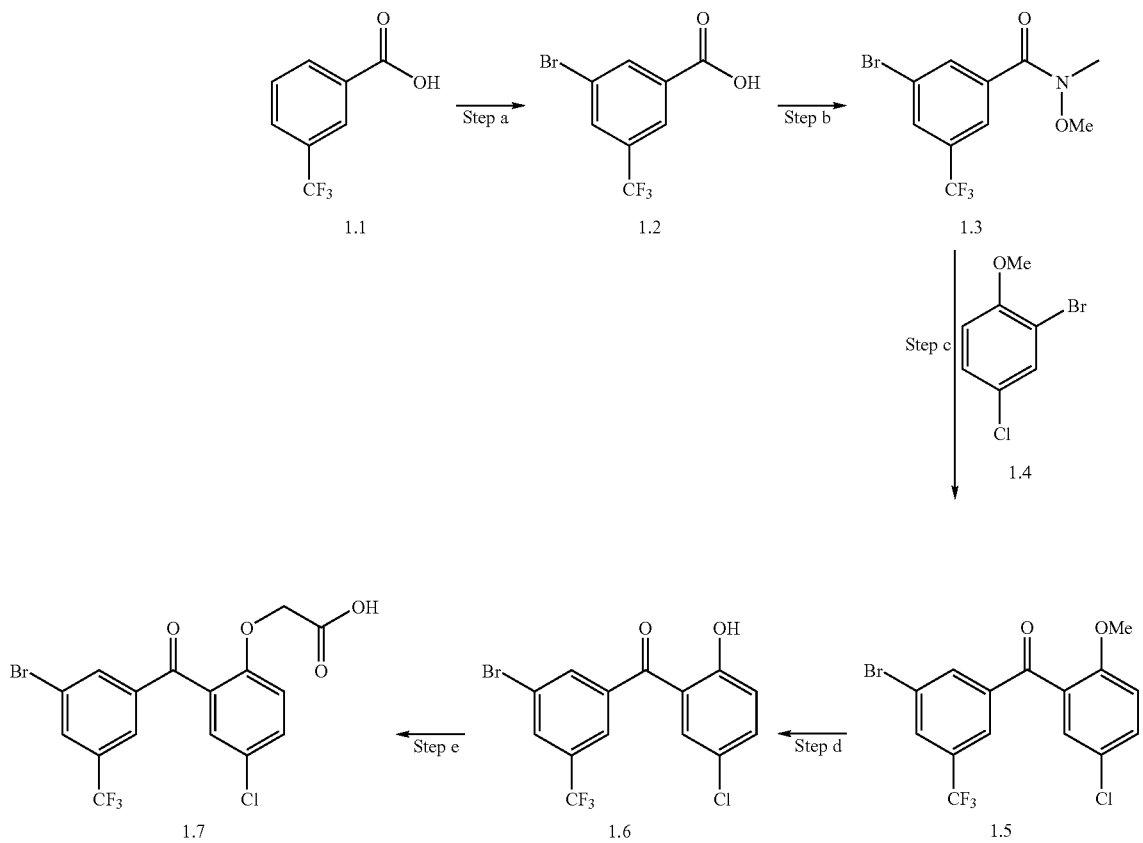

allowed to warm to room temperature and stirring was continued for 1 h. Water was slowly added and the reaction mixture was partitioned between water and Et$_2$O. The organic layer was dried (MgSO$_4$), filtered and concentrated under reduced pressure. The resulting gum was purified by flash chromatography (hexane/EtOAc, 95/5) to give compound 1.5 (2.45 g, 73% yield) as a white solid.

tered and concentrated under reduced pressure to give compound 1.7 (421 mg, 97% yield) as a off-white solid.

Example 2

Benzophenone Intermediate 2.5

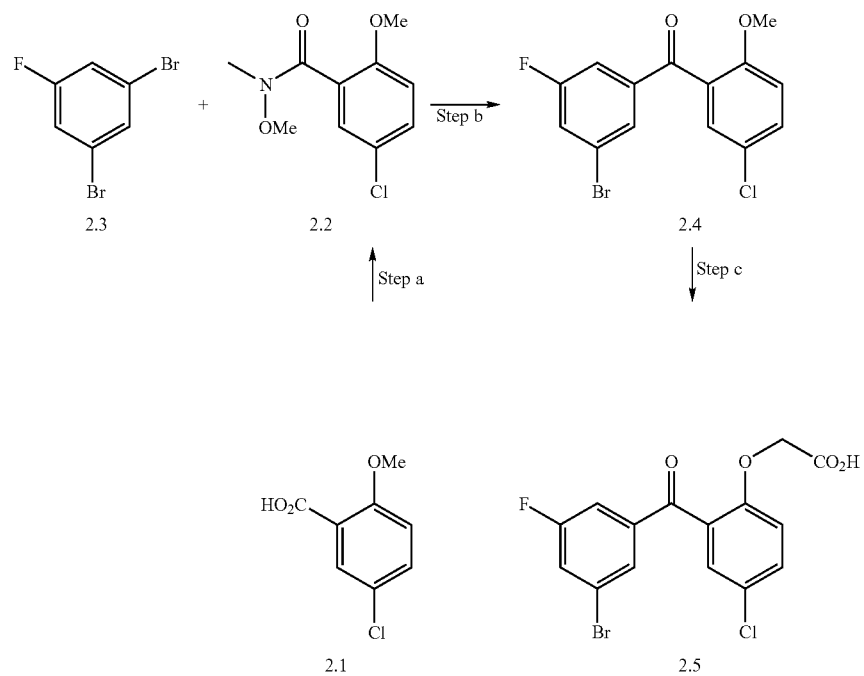

d) Compound 1.6

To a solution of compound 1.5 (442 mg, 1.12 mmol) in CH$_2$Cl$_2$ (6 mL) cooled at 0° C. was added a solution of 1.0 M BBr$_3$ in CH$_2$Cl$_2$ (6.0 mL, 6.0 mmol). After 1 h ice was added and the resulting mixture partitioned between water and EtOAc. The organic layer was washed with water and brine, dried (MgSO$_4$), filtered, and concentrated under reduced pressure to give compound 1.6 (430 mg, 100% yield) as a gum.

e) Compound 1.7

To a solution of phenol 1.6 (425 mg, 1.12 mmol) in acetone (10 mL) was added K$_2$CO$_3$ (500 mg, 3.62 mmol) and methyl bromoacetate (200 μL, 2.11 mmol), and the mixture was heated at 50° C. for 2 h. Upon cooling the reaction mixture was concentrated and diluted with EtOAc, and the resulting solution was successively washed with water and brine, dried (MgSO$_4$), filtered and concentrated under reduced pressure. The crude ester was purified by flash chromatography (hexane/EtOAc, 90/10) to give the pure ester (447 mg, 88% yield). The ester was dissolved in THF (2 mL) and MeOH (2 mL) and aqueous 1 N NaOH solution (2.0 mL, 2.0 mmol) was added. The solution was stirred for 30 min then was slowly acidified with aqueous 1 N HCl solution (3 mL). The mixture was extracted with EtOAc, washed with water and brine, dried (MgSO$_4$), fila) Compound 2.2

To a solution of acid 2.1 (20.3 g, 109 mmol) in CH$_2$Cl$_2$ (500 mL) were added (COCl)$_2$ (14.0 mL, 157 mmol) and DMF (0.2 mL). After 2 h the reaction mixture was concentrated under reduced pressure. A solution of the resulting acyl chloride (22.3 g, 109 mmol) in CH$_2$Cl$_2$ (80 mL) was added dropwise to a solution of Et$_3$N (45.0 mL, 323 mmol) and MeNH(OMe).HCl (13.9 g, 142 mmol) in CH$_2$Cl$_2$ (300 mL). The resulting solution was stirred at room temperature for 2 h. The reaction mixture diluted with EtOAc was successively washed with aqueous 1 N HCl solution, aqueous saturated NaHCO$_3$ solution and brine, dried (MgSO$_4$), filtered and concentrated under reduced pressure to give compound 2.2 (24.3 g, 97% yield) as a white solid.

b) Compound 2.4

Using a method similar to the one described in Example 1, Step c, but starting with compound 2.3 (4.40 g, 17.3 mmol) and compound 2.2 (3.98 g, 17.3 mmol), compound 2.4 (3.60 g, 60% yield) was obtained as a yellow solid.

c) Compound 2.5

Using a method similar to the one described in Example 1, Steps d and e, but starting with compound 2.4 (2.00 g, 5.82 mmol), compound 2.5 (1.16 g, 51% yield) was obtained as a beige solid.

Example 3

Benzophenone Intermediate 3.2

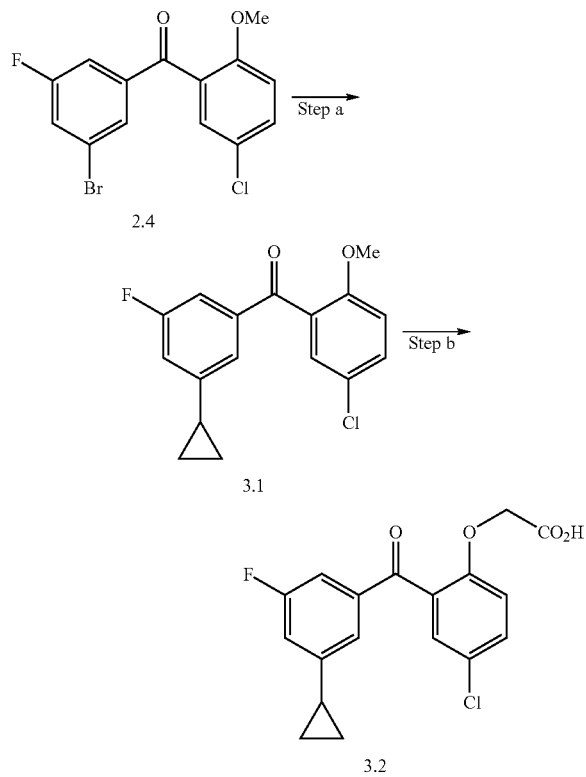

a) Compound 3.1

A solution of 1.6 M n-BuLi in hexane (7.28 mL, 11.5 mmol) was added over 45 min to a cold (−78° C.) solution of cyclopropylbromide (1.17 mL, 14.5 mmol) in THF (40 mL). After 1 h, a solution of ZnBr$_2$ (flame dried under high vacuum, 2.88 g, 12.8 mmol) in THF (10 mL) was added by cannula and the mixture was allowed to warm to room temperature. After 1 h a solution of compound 2.4 (from Example 2) (2.00 g, 5.82 mmol) in THF (30 mL) and Pd(PPh$_3$)$_4$ (672 mg, 0.58 mmol, under stream of nitrogen) were added. The reaction mixture was heated at reflux for 16 h, then cooled in an ice bath and quenched with saturated aqueous NaHCO$_3$ solution. The resulting mixture was extracted with EtOAc several times and the combined organic layers were successively washed with water and brine, dried (MgSO$_4$), filtered and concentrated under reduced pressure. The crude product was purified by flash chromatography (hexane/EtOAc 90/10) to give compound 3.2 (1.25 g, 70% yield) as a pale yellow solid.

b) Compound 3.2

Using a method similar to the one described in Example 1, Steps d and e, but starting with compound 3.1 (1.20 g, 3.94 mmol), acid 3.2 (1.30 g, 95% yield) was obtained as a white solid.

Example 4

Benzophenone Intermediate 4.3

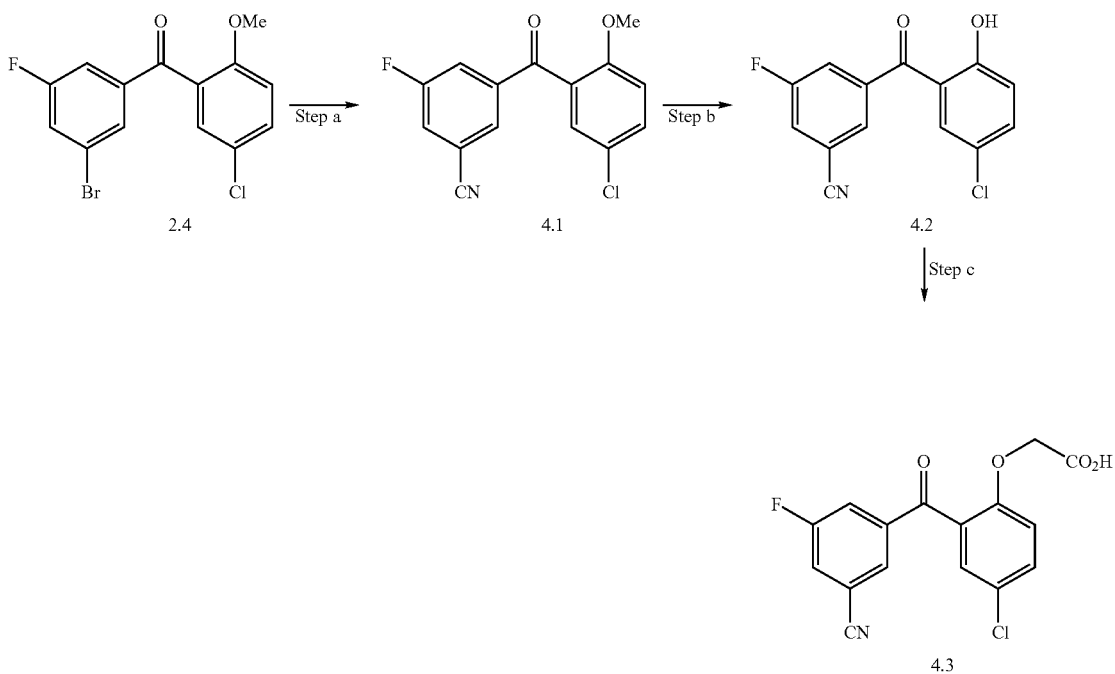

a) Compound 4.1

A mixture of compound 2.4 (8.63 g, 25.1 mmol) and CuCN (6.75 g, 75.4 mmol, dried at 100° C. under reduced pressure for 18 h) in DMF (50 mL) was heated at 185° C. for 3.5 h. The cooled reaction mixture was diluted with EtOAc and the resulting solution was washed with concentrated NH$_4$OH solution, water and brine, dried (MgSO$_4$), filtered and concentrated to a volume of about 50 mL. Hexane (150 mL) was then added and the resulting precipitate was recovered by filtration and dried to give compound 4.1 (5.70 g, 78% yield) as a off-white solid.

Compound 4.1 (R$^2$=CN) can be transformed to the corresponding intermediate wherein R$^2$ is C(=O)NH$_2$ using hydration reaction conditions well known to one skilled in the art. Such an intermediate may be subsequently transformed to compounds of formula (I) wherein R$^2$ is C(=O)NH$_2$ using the methodology described herein.

b) Compound 4.2

A solution of 1.0 M BBr$_3$ in CH$_2$Cl$_2$ (50.0 mL, 50.0 mmol) was added over 15 min to a cold (−78° C.) solution of compound 4.1 (5.70 g, 19.7 mmol) in CH$_2$Cl$_2$ (120 mL). The reaction mixture was stirred at −78° C. for 1 h then was allowed to warm to room temperature (30 min). The mixture was poured into ice-water and the phases were separated. The aqueous layer was extracted with CH$_2$Cl$_2$ (3×). The combined organic layers were washed with water, dried (MgSO$_4$), filtered and concentrated under reduced pressure. The residue was dissolved in EtOAc (30 mL) and hexane (100 mL) was added. The resulting green solid obtained by filtration was washed with hexane (10 mL), dried under reduced pressure to give compound 4.2 (4.72 g, 87% yield).

c) Compound 4.3

A solution of phenol 4.2 (4.72 g, 17.1 mmol), K$_2$CO$_3$ (7.09 g, 51.4 mmol) and t-butyl bromoacetate (2.82 mL, 17.5 mmol) in acetone (75 mL) was heated at 50° C. for 1.5 h. The cooled reaction mixture diluted with EtOAc was washed with water (2×) and brine, dried (MgSO$_4$), filtered and concentrated under reduced pressure. A solution of the residue in TFA (25 mL) and CH$_2$Cl$_2$ (50 mL) was stirred at room temperature for 1 h. The reaction mixture was concentrated under reduced pressure to a volume of 40 mL, hexane (100 mL) was added and the resulting suspension was filtered. The solid was washed with hexane, dried under reduced pressure to give compound 4.3 (5.14 g, 90% yield) as a white solid.

Example 5

Benzophenone Intermediate 5.4

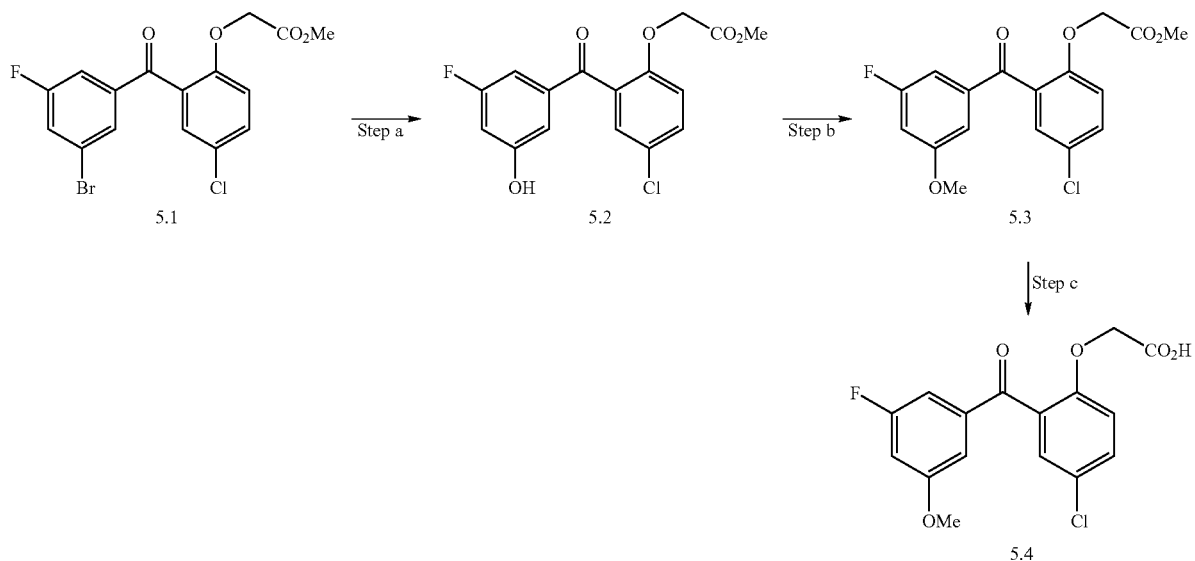

a) Compound 5.2

A solution of compound 5.1 (intermediate in the synthesis of compound 2.5; 300 mg, 0.747 mmol), dppf (41.6 mg, 75.0 μmol), bis(pinacolato)diboron (228 mg, 900 μmol) and AcOK (478 mg, 2.25 mmol) in toluene (10 mL) was degassed under reduced pressure for 20 min. PdCl$_2$(dppf) (1:1 complex with CH$_2$Cl$_2$; 54.9 mg, 75.0 μmol) was added and the reaction mixture was heated at 80° C. for 18 h. An additional portion of catalyst (54.9 mg, 75.0 μmol) was added and the mixture was heated for 20 min. The cooled reaction mixture was diluted with EtOAc and the resulting solution was washed with water, dried (MgSO$_4$), filtered through a pad of diatomaceous earth and concentrated under reduced pressure. To an ice-cold solution of the residue in acetone (9 mL) and aqueous saturated NaHCO$_3$ solution (1 mL) was added 2KHSO$_5$.KHSO$_4$.K$_2$SO$_4$ (700 mg, 1.14 mmol). After 5 min NaHSO$_3$ (500 mg, 4.78 mmol) was added and the reaction mixture was concentrated under reduced pressure. The residue was partitioned between water and EtOAc. The organic layer was washed with water and brine, dried (MgSO$_4$), filtered and concentrated under reduced pressure. The residue was purified by flash chromatography (hexane:EtOAc, 90/10 to 50/50) to give compound 5.2 (170 mg, 67% yield) as colorless gum.

b) Compound 5.3

NaH (60% in mineral oil; 12.8 mg, 320 μmol) was added to a solution of compound 5.2 (100 mg, 295 μmol) in DMF (3.0 mL). After 15 min, MeI (21.8 μL, 350 μmol) was added and the reaction mixture was stirred at room temperature for 2 h. The mixture was diluted with Et$_2$O and the resulting solution was washed with water (3×), dried (MgSO$_4$), filtered and concentrated under reduced pressure. The residue was purified by flash chromatography (hexane/EtOAc, 80/20 to 50/50) to afford compound 5.3 (67 mg, 64% yield) as a colorless gum.

Compound 5.2, or analogs thereof in which the —COOMe group has been replaced by another suitable ester, may be converted to other intermediates wherein the methoxy group on the phenyl ring is replaced by another alkoxy group or substituted alkoxy group by using the methodology of step b above but replacing MeI with an appropriate alkylating agent.

c) Compound 5.4

A solution of compound 5.3 (66 mg, 0.19 mmol) and aqueous 1 N LiOH solution (0.5 mL, 0.5 mmol) in THF (2.25 mL) and MeOH (0.75 mL) was stirred at room temperature for 1 h. The reaction mixture was concentrated under reduced pressure, the residue was diluted with water and acidified with aqueous 1.0 N HCl solution. The mixture was extracted with EtOAc. The organic phase was dried (MgSO$_4$), filtered and concentrated under reduced pressure to give compound 5.4 (64 mg, 100% yield).

Using the methods of Example 1, steps b to e, or Example 2, but starting with commercially available appropriately substituted benzoic acid and bromobenzene intermediates, other benzophenone intermediates used in the preparation of compounds of formula (I) may be prepared.

Example 6

Aniline Intermediates 6.5 and 6.7 b) Compound 6.4

A solution of acid 6.3 (8.00 g, 71.3 mmol), 2-(trimethylsilyl)ethanol (10.2 mL, 71.3 mmol), Et$_3$N (20.9 mL, 150 mmol) and TBTU (29.8 g, 92.8 mmol) in DMF (120 mL) was stirred at room temperature for 16 h. The reaction mixture was diluted with Et$_2$O and the resulting solution was washed with water and brine, dried (MgSO$_4$), filtered and concentrated under reduced pressure. The crude residue was purified by flash chromatography (hexane/EtOAc, 95/5) to afford the compound 6.4 (10.8 g, 71% yield) as a clear oil.

c) Compound 6.5

To a solution of aniline 6.2 (1.09 g, 4.00 mmol) in THF (10 mL) was added CuI (76 mg, 0.40 mmol), Et$_2$NH (1.04 mL, 10.0 mmol) and compound 6.4 (850 mg, 4.00 mmol). The mixture was degassed for 15 min by bubbling argon through the solution. Pd(PPh$_3$)$_4$ (462 mg, 400 μmol) was added and the reaction mixture was heated at reflux until total disappearance of the starting material was indicated by TLC. The black solution was cooled to room temperature, silica gel was added and all volatiles were removed under reduced pressure to give a dry powder which was applied at the top of a column. The crude compound was purified by flash chromatography (hexane/EtOAc, 80/20 to 50/50) to afford compound 6.5 (1.13 g, 79% yield) as a brown oil.

Using a procedure similar to that described in step c above, but using commercially available compound 6.6 in place of compound 6.2, aniline intermediate 6.7 was prepared.

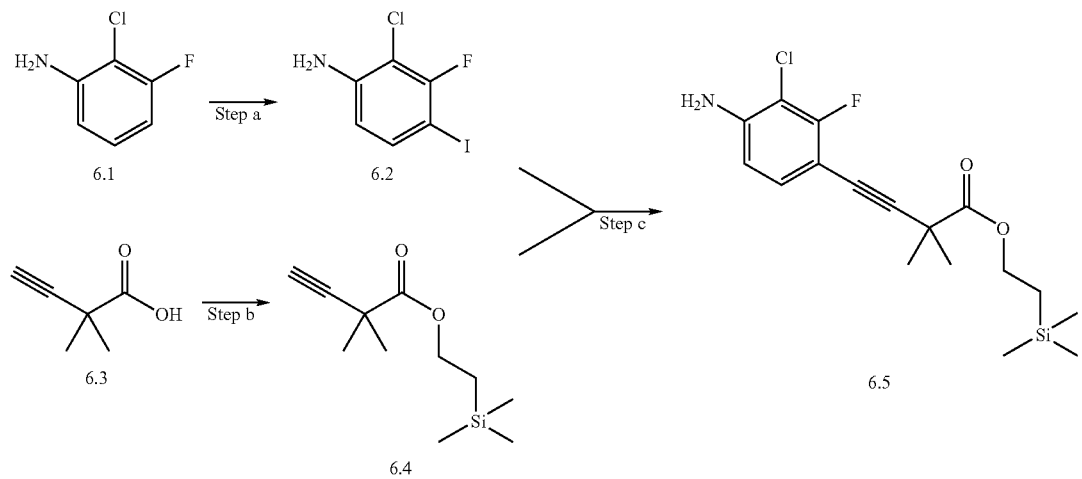

a) Compound 6.2

To a solution of aniline 6.1 (500 mg, 3.43 mmol) in acetic acid (4 mL) was added KI (820 mg, 4.94 mmol), NaBO$_3$·4H$_2$O (710 mg, 4.61 mmol) and (NH$_4$)$_2$MoO$_4$ (710 mg, 3.62 mmol). After 30 min the reaction was poured into a mixture of saturated aqueous NaHCO$_3$ solution (5 mL) and aqueous 10% Na$_2$S$_2$O$_3$ solution (1 mL). The aqueous layer was extracted with Et$_2$O and the combined organic phase were washed with brine, dried (MgSO$_4$), filtered and concentrated under reduced pressure to give compound 6.2 (860 mg, 92% yield) as a beige solid.

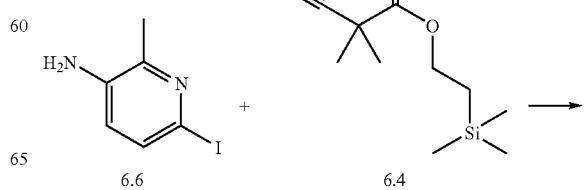

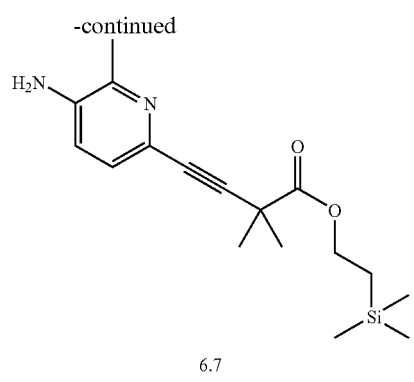

Example 7

Aniline Intermediate 7.5

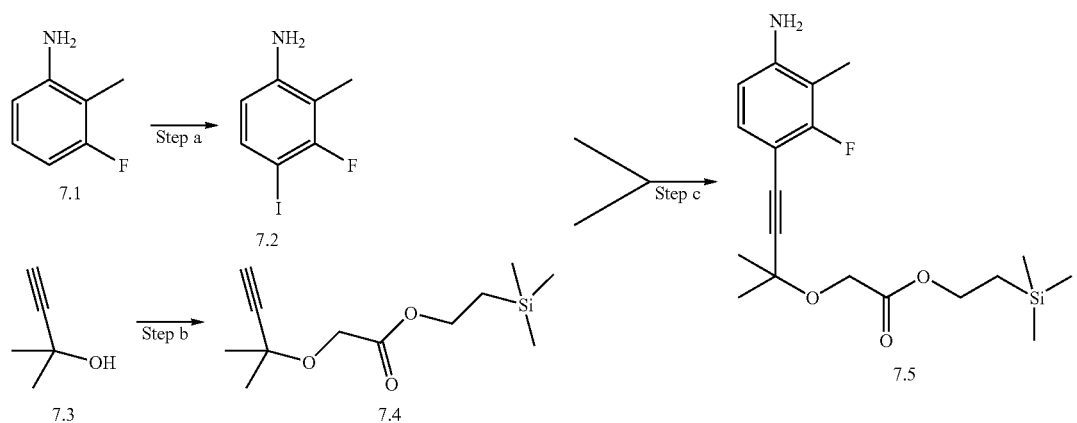

a) Compound 7.2

Using a method similar to the one described in Example 6, Step a, but starting with aniline 7.1 (5.20 g, 41.5 mmol), compound 7.2 (9.96 g, 95% yield) was obtained as a brown solid.

b) Compound 7.4

To compound 7.3 (225 mL, 2.32 mol) was added [Rh(OAc)$_3$]$_2$ (682 mg, 1.54 mmol) followed by slow addition of ethyl diazoacetate (30.0 mL, 285 mmol). After stirring for 1 h at room temperature the excess of compound 7.3 was removed by distillation. The residue was purified by flash chromatography (hexane to hexane/EtOAc 90/10) to give the corresponding ethyl ester (8.20 g, 17% yield). To a solution of the ethyl ester (3.00 g, 17.6 mmol) in THF (45 mL) was added an aqueous 1.0 N LiOH solution (21.1 mL, 21.1 mmol). The reaction mixture was heated at reflux for 1.5 h. The mixture was acidified with aqueous 1 N HCl solution and extracted with EtOAc. The organic layer was washed with water and brine, dried (MgSO$_4$), filtered and concentrated under reduced pressure. The resulting acid was dissolved in CH$_2$Cl$_2$ (100 mL) and the solution cooled to 0° C. 2-(Trimethylsilyl)ethanol (3.02 mL, 21.1 mmol), 1.0 M DCC solution in CH$_2$Cl$_2$ (21.1 mL, 21.1 mmol) and DMAP (516 mg, 4.22 mmol) were added and the reaction mixture was stirred at room temperature for 3 h. The reaction slurry was filtered through a pad of diatomaceous earth and the resulting solution was washed with aqueous 1.0 N HCl solution, saturated aqueous NaHCO$_3$ and brine, dried (MgSO$_4$), filtered and concentrated under reduced pressure. The residue was purified by flash chromatography (hexane to hexane/EtOAc 80/20) to give compound 7.4 (3.40 g, 80% yield) as a light yellow oil.

c) Compound 7.5

Using a method similar to the one described in Example 6, Step c, but starting with aniline 7.2 (1.00 g, 3.98 mmol) and compound 7.4 (1.06 g, 4.38 mmol), compound 7.5 (946 mg, 65% yield) was obtained as a brown thick gum.

Example 8

Aniline Intermediate 8.1

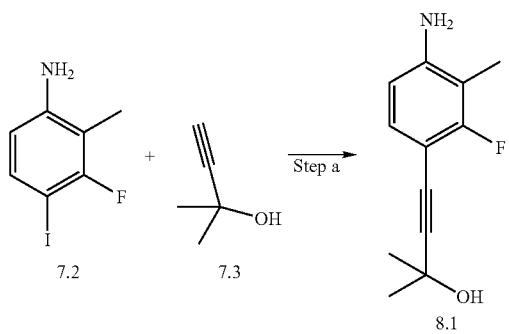

a) Compound 8.1

A mixture of aniline 7.2 (from Example 7) (2.08 g, 8.29 mmol), CuI (237 mg, 1.24 mmol), Et₂NH (8.61 mL, 82.9 mmol) and compound 7.3 (2.01 g, 20.7 mmol) in THF (150 mL was degassed by bubbling argon through the solution for 15 min. Pd(PPh₃)₄ (1.44 g, 1.24 mmol) was added and the reaction mixture was heated at reflux for 2 h. The black solution was cooled to room temperature, silica gel was added and all volatiles were removed under reduced pressure to give a dry powder which was applied at the top of a column. The crude compound was purified by flash chromatography (hexane/EtOAc, 90/10 to 20/80) to afford compound 8.1 (1.25 g, 73% yield) as a brown oil.

Example 9

Aniline Intermediate 9.3

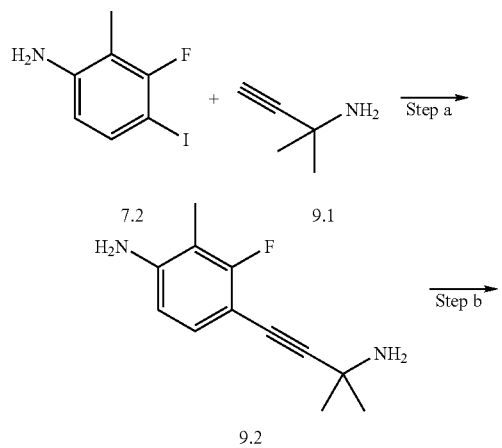

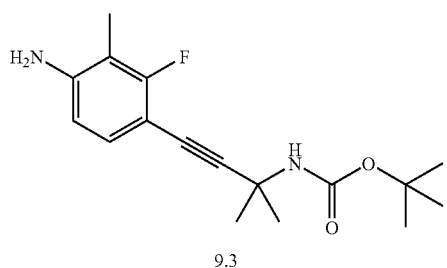

a) Compound 9.2

Using a method similar to the one described in Example 6, Step c, but starting with aniline 7.2 (from Example 7) (5.00 g, 19.9 mmol) and compound 9.1 (1.99 g, 23.9 mmol), compound 9.2 (1.10 g, 27% yield) was obtained as a brown gum.

b) Compound 9.3

To a solution of compound 9.2 (200 mg, 970 µmol) in THF (10 mL) was added Et₃N (194 µL, 1.10 mmol) and di-tert-butyl dicarbonate (194 mg, 1.10 mmol). After stirring overnight at room temperature the reaction mixture was concentrated under reduced pressure. The residue was purified by flash chromatography (hexane/EtOAc 70/30 to 50/50) to give compound 9.3 (280 mg, 94% yield) as a yellow gum.

Example 10

Aniline Intermediate 10.6

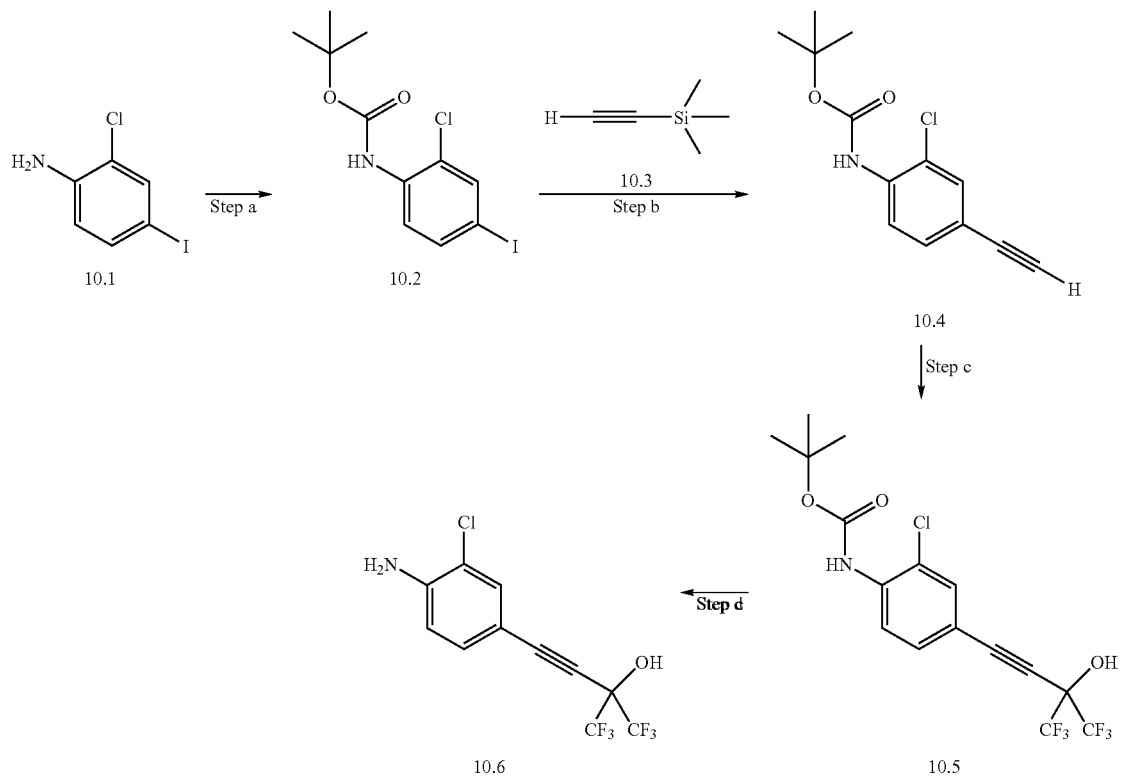

a) Compound 10.2

A solution of NaHMDS (22.8 g, 124 mmol) in THF (100 mL) was added to a solution of aniline 10.1 (15.0 g, 59.2 mmol) in THF (250 mL) at room temperature. After 15 min di-tert-butyl dicarbonate (12.3 g, 56.2 mmol) was added by portions and the mixture was stirred at room temperature for 16 h. Aqueous 10% HCl solution was slowly added and the mixture was extracted with Et$_2$O. The organic layer was washed with aqueous saturated NaHCO$_3$ solution, dried (MgSO$_4$), filtered and concentrated under reduced pressure. The residue was purified by flash chromatography (hexane/EtOAc, gradient 95/5 to 50/50) to give compound 10.2 (16.0 g, 77% yield) as a pale orange solid.

b) Compound 10.4

A mixture of aniline 10.2 (2.00 g, 5.66 mmol), CuI (467 mg, 2.46 mmol), Et$_3$N (3.15 mL, 22.6 mmol) and compound 10.3 (939 µL, 6.79 mmol) in THF (60 mL was degassed by bubbling argon through the solution for 15 min. Pd(PPh$_3$)$_4$ (647 mg, 0.56 mmol) was stirred at room temperature until disappearance of the starting material (TLC). The reaction mixture was diluted with Et$_2$O and the solution was washed with aqueous 1 N HCl solution and water, dried (MgSO$_4$), filtered and concentrated under reduced pressure The residue was purified by flash chromatography (hexane/EtOAc, 95/5) to afford the silylalkyne (1.80 g, 98% yield) as a brown oil. A mixture of the resulting silylalkyne (1.80 g, 5.56 mmol) and K$_2$CO$_3$ (3.84 g, 27.8 mmol) in MeOH (55 mL) was stirred at room temperature for 10 min. The reaction mixture diluted with Et$_2$O was washed with water. The aqueous layers were extracted with Et$_2$O. The combined organic layers were dried (MgSO$_4$), filtered and concentrated under reduced pressure to give compound 10.4 (1.17 g, 84% yield) as a brown oil.

c) Compound 10.5

A solution of 2.5 M n-BuLi in hexane (2.31 mL, 5.77 mmol) was added dropwise to a cold (−78° C.) solution of 10.4 (415 mg, 1.65 mmol) in THF (10 mL). After 30 min a solution of hexafluoroacetone (821 mg, 4.95 mmol) in THF (20 mL) was added and the reaction mixture was stirred for 30 min at −78° C. Saturated aqueous NH$_4$Cl solution was added and the resulting mixture was extracted with Et$_2$O. The organic layer was washed with aqueous NH$_4$Cl solution, dried (MgSO$_4$), filtered and concentrated under reduced pressure. The residue was purified by flash chromatography (hexane/EtOAc, 98/2 to 95/5) to give compound 10.5 (400 mg, 58% yield) as a white solid.

d) Compound 10.6

A solution of compound 10.5 (130 mg, 311 µmol) and t-BuONa (298 mg, 3.1 mmol) and water (14.7 µL, 0.82 mmol) in THF (2.0 mL) was heated at 100° C. for 3 days. Additional portions of t-BuONa (50 mg, 1.67 mmol) and water (7.7 µL, 0.42 mmol) were added and the mixture was heated at 100° C. for an additional 24 h. An aqueous 10% citric acid solution was added and the reaction mixture was diluted with EtOAc. The phases were separated and the aqueous layer was extracted with EtOAc. The combined organic layers were washed with brine, dried (MgSO$_4$), filtered and concentrated under reduced pressure. The residue was purified by flash chromatography (hexane/EtOAc, 8/2) to give compound 10.6 (26 mg, contaminated with the corresponding symmetrical urea) as a brown solid.

Example 11

Aniline Intermediate 11.4

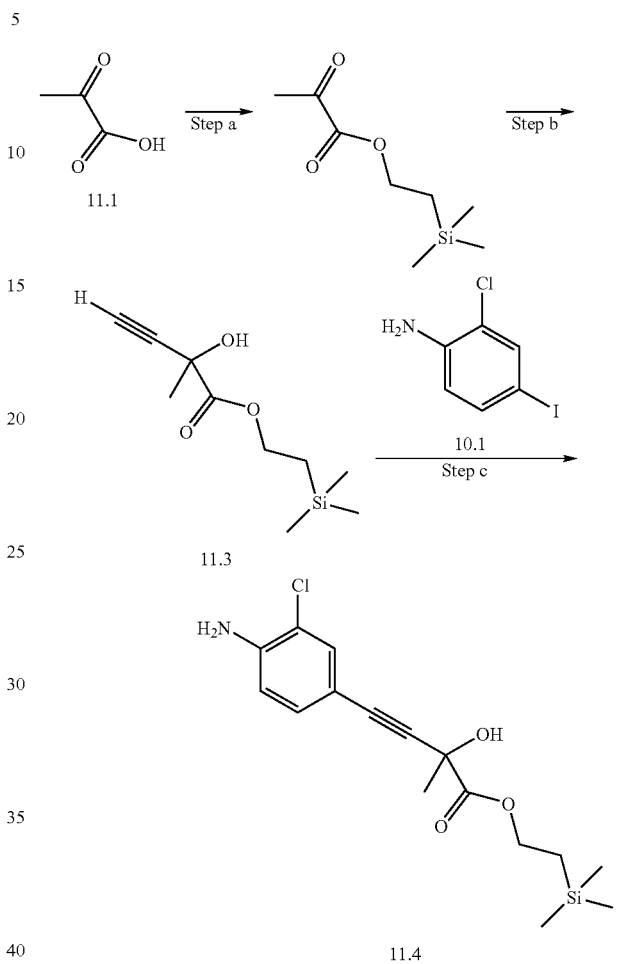

a) Compound 11.2

A 1.0 M solution of DCC in CH$_2$Cl$_2$ (59.0 mL, 59.0 mmol) was added to an ice-cold solution of compound 11.1 (5.20 g, 59.0 mmol), 2-trimethylsilylethanol (8.46 mL, 59.0 mmol) and DMAP 1.44 g, 11.8 mmol) in CH$_2$Cl$_2$ (200 mL). The reaction mixture was stirred at room temperature for 3 h. The solution was successively washed with aqueous 10% HCl solution, saturated aqueous NaHCO$_3$ solution and brine, dried (Na$_2$SO$_4$), filtered and concentrated under reduced pressure. The residue was purified by flash chromatography (hexane/EtOAc, 95/5 to 80/20) to yield compound 11.2 (3.60 g, 32% yield).

b) Compound 11.3

A 0.5 M solution of ethynylmagnesium bromide in THF (38.2 mL, 19.1 mmol) was added to a cold (−78° C.) solution of compound 11.2 (3.60 g, 19.1 mmol) in Et$_2$O (100 mL). The reaction mixture was stirred at −78° C. for 30 min then was allowed to warm to 0° C. Saturated aqueous NH$_4$Cl solution was added and the phases were separated. The aqueous layer was extracted with Et$_2$O (3×). The combined organic layer were washed with saturated aqueous NaHCO$_3$ and brine, dried (Na$_2$SO$_4$), filtered and concentrated under reduced pressure. The residue was purified by flash chromatography (hexane/EtOAc, 95/5 to 90/10) to give compound 11.3 (1.30 g, 32% yield) as a yellow oil.

c) Compound 11.4

A mixture of aniline 10.1 (1.00 g, 3.94 mmol), CuI (75.2 mg, 395 μmol), Et$_2$NH (4.10 mL, 39.4 mmol) and compound 11.3 (930 mg, 4.34 mmol) in THF (50 mL was degassed by bubbling argon through the solution for 15 min. Pd(PPh$_3$)$_4$ (456 mg, 0.39 mmol) was added and the reaction mixture was heated at reflux for 16 h. The black solution was cooled to room temperature, silica gel was added and all volatiles were removed under reduced pressure to give a dry powder which was applied at the top of a column. The crude compound was purified by flash chromatography (hexane/EtOAc, 80/20 to 60/40) to afford compound 11.4 (729 mg, 54% yield) as a yellow oil.

The methods of Examples 6 to 11 may be used to prepare other aniline intermediates used in the preparation of compounds of formula (I), from commercially available, appropriately substituted iodoaniline and alkyne precursors.

Example 12

Entry 1051

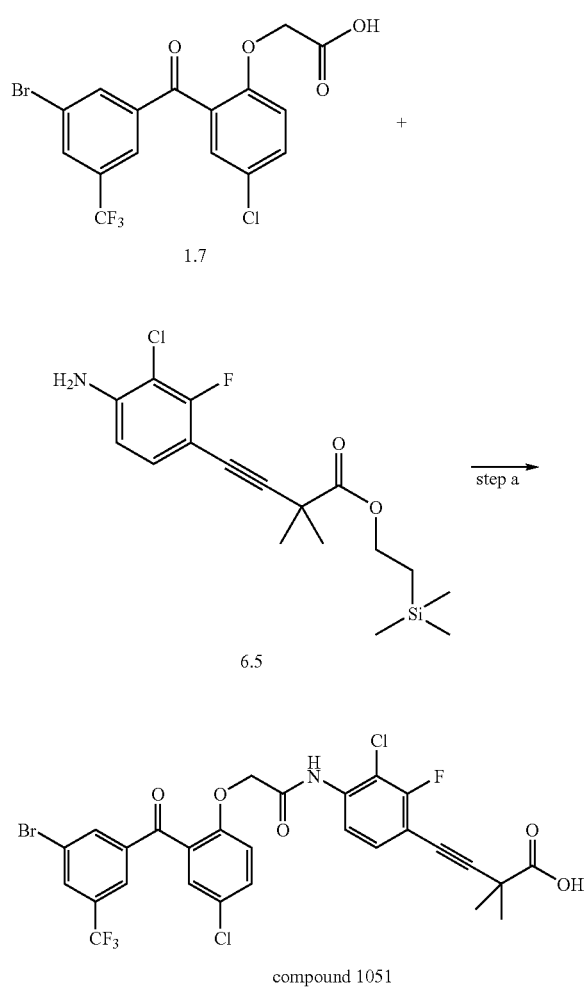

compound 1051 a) Compound 1051

To a solution of acid 1.7 (from Example 1) (110 mg, 0.251 mmol) in CH$_2$Cl$_2$ (3 mL) was added (COCl)$_2$ (41 μL, 0.47 mmol) and DMF (1 drop). After 2 h the reaction was concentrated under reduced pressure to give the corresponding acyl chloride. The crude acyl chloride (55 mg, 0.12 mmol) was dissolved in THF (3 mL), pyridine (30 μL, 0.37 mmol) and compound 6.5 (from Example 6) (41 mg, 0.12 mmol) were added, and the resulting solution was stirred at room temperature for 2 h. A solution of 1.0 M Bu$_4$NF in THF (1.0 mL, 1.0 mmol) was added and the reaction mixture was stirred at room temperature for 1 h, then was concentrated under reduced pressure. The crude acid was purified by RP-HPLC. The pure fractions were combined and concentrated to give compound 1051 (19 mg, 23% yield) as a white solid. $^1$H-NMR (DMSO-d$_6$): 612.78-13.15 (bs, 1H), 9.44 (s, 1H), 8.23 (s, 1H), 8.16 (s, 1H), 8.00 (s, 1H), 7.70 (d, J=10.0 Hz, 1H), 7.67 (dd, J=9.0, 2.6 Hz, 1H), 7.57 (d, J=2.6 Hz, 1H), 7.43 (t, J=7.8 Hz, 1H), 7.25 (d, 9.0 Hz, 1H), 4.85 (s, 2H), 1.47 (s, 6H).

Example 13

(Entry 1089)

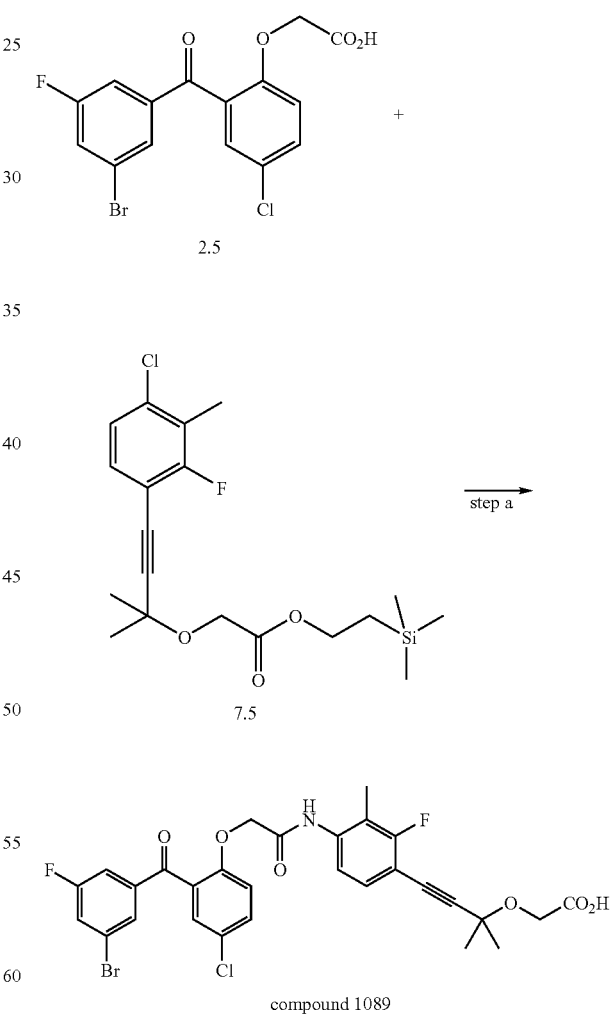

compound 1089 a) Compound 1089

Using a method similar to the one described in Example 12, Step a, but starting with compound 2.5 (From Example 2) (85.1 mg, 0.23 mmol) and aniline 7.5 (from Example 7)

(83.7 mg, 0.23 mmol), compound 1089 (80 mg, 55% yield) was obtained as a white solid. $^1$H-NMR (DMSO-$d_6$): δ 12.89 (s, 1H), 9.47 (s, 1H), 7.86 (d, J=7.9 Hz, 1H), 7.73 (s, 1H), 7.64 (dd, J=8.9, 2.6 Hz, 1H), 7.56 (d, J=7.2 Hz, 1H), 7.51 (d, J=2.7 Hz, 1H), 7.35-7.25 (m, 2H), 7.22 (d, J=9 Hz, 1H), 4.80 (s, 2H), 4.13 (s, 2H), 2.01 (s, 2H), 2.01 (s, 3H), 1.50 (s, 6H).

Example 14

(Entry 1168)

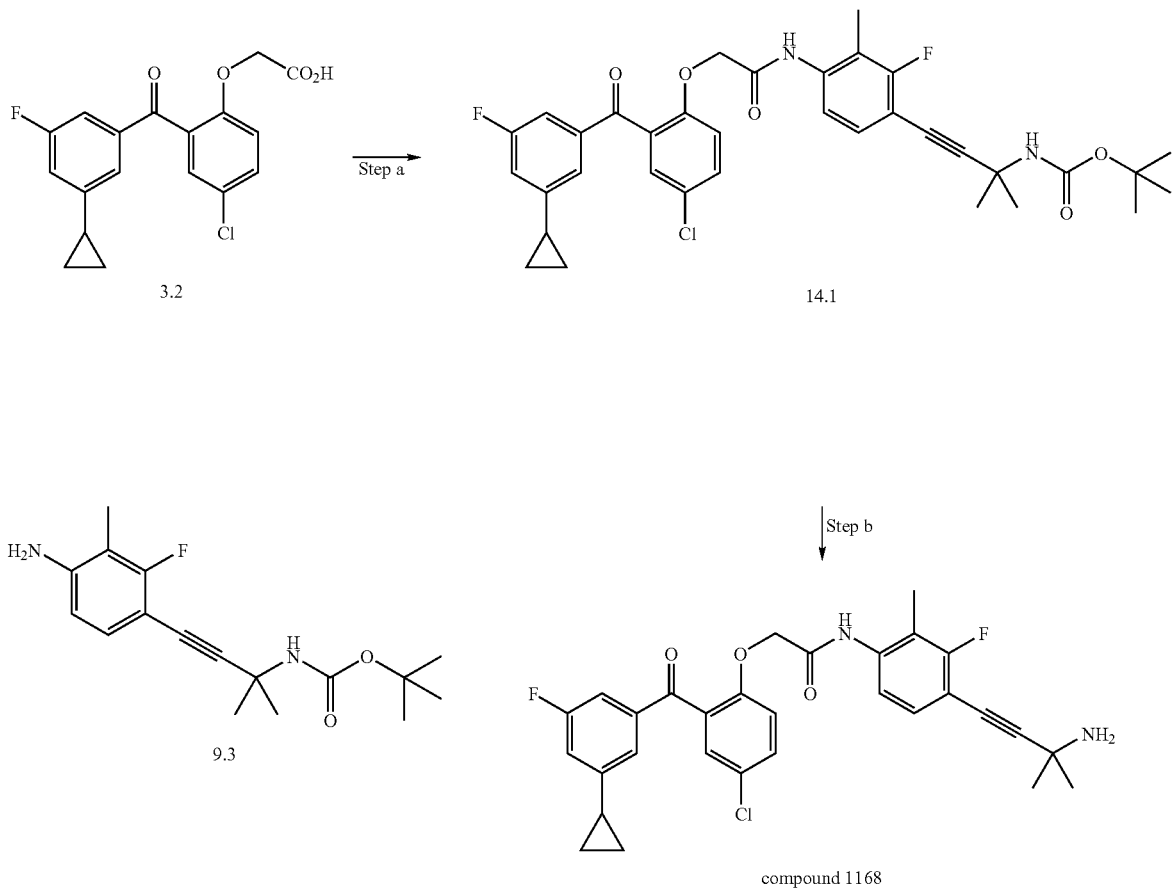

a) Compound 14.1

To a solution of acid 3.2 (from Example 3) (100 mg, 0.29 mmol) in CH$_2$Cl$_2$ (3 mL) was added (COCl)$_2$ (28 μL, 0.32 mmol) and DMF (1 drop). After 2 h the reaction was concentrated under reduced pressure to give the corresponding acyl chloride. The crude acyl chloride was dissolved in THF (3 mL), pyridine (70 μL, 0.86 mmol) and compound 9.3 (from Example 9) (97 mg, 0.32 mmol) were added and the resulting solution was stirred at room temperature for 16 h. The reaction mixture was partitioned between saturated aqueous NaHCO$_3$ solution and EtOAc. The organic phase was washed with saturated aqueous NaHCO$_3$ solution and brine, dried (Na$_2$SO$_4$), filtered and concentrated under reduced pressure. The residue was purified by flash chromatography (hexane/EtOAc, 95/5 to 50/50) to give compound 14.1 (120 mg, 66% yield) as a clear oil.

b) Compound 1168

To a solution of compound 14.1 (120 mg, 0.19 mmol) in 1,4-dioxane (2 mL) was added a solution of 4.0 N HCl in 1,4-dioxane (0.47 mL, 1.88 mmol). After 1 h at room temperature, the reaction was concentrated and the crude amine was purified by RP-HPLC. The pure fractions were combined and concentrated to give compound the TFA salt of 1168 (39 mg, 32% yield) as a white solid. $^1$H-NMR (DMSO-$d_6$): δ 9.41 (s, 1H), 8.55 (bs, 2H), 7.63 (dd, J=9.0, 2.5 Hz, 1H), 7.48 (d, J=2.5 Hz, 1H), 7.43-7.16 (m, 5H), 4.82 (s, 2H), 2.55 (m, 1H), 2.04 (s, 3H), 1.63 (s, 6H), 0.97 (m, 2H), 0.71 (m, 2H).

Example 15

(Entries 1169 and 1177)

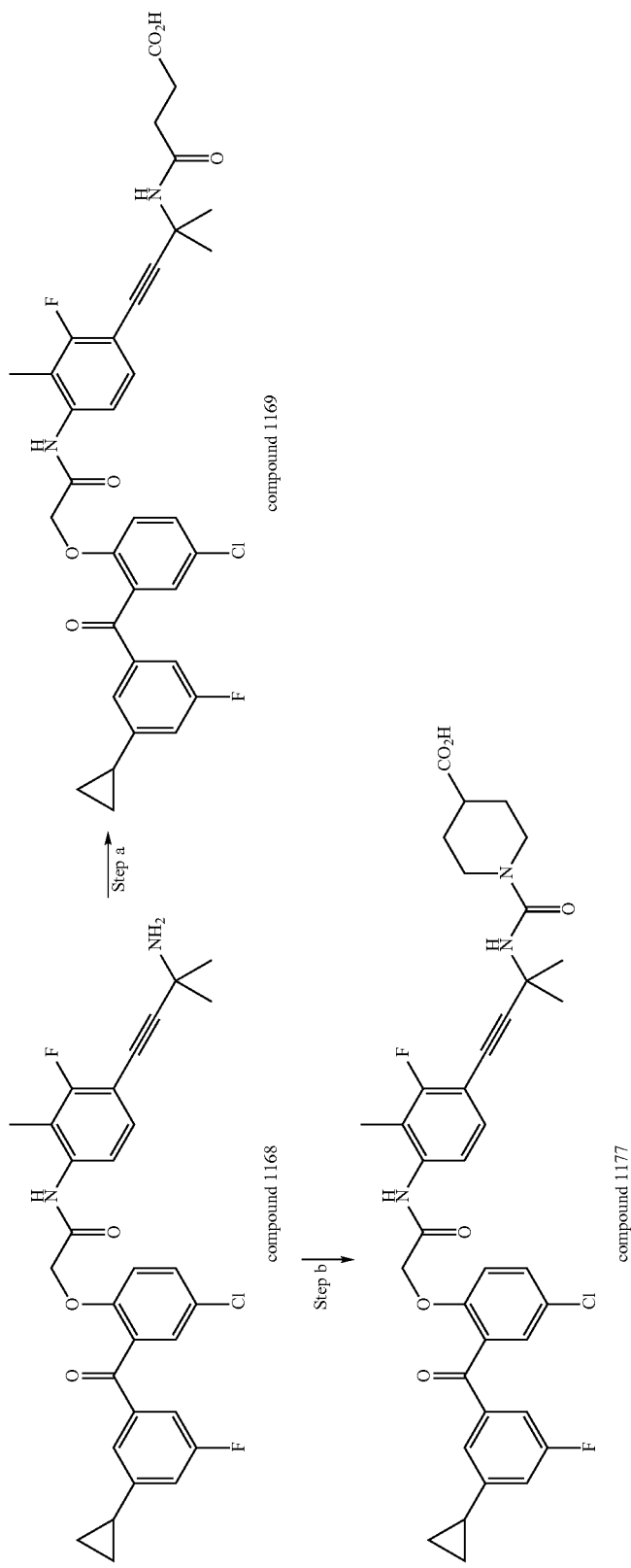

a) Compound 1169

To a solution of the TFA salt of compound 1168 (50.5 mg, 77.5 μmol) in $CH_2Cl_2$ (2 mL) was added succinic anhydride (12.2 mg, 0.12 mmol) and $Et_3N$ (65 μL, 0.47 mmol). The reaction mixture was heated at reflux for 2 h. The mixture was concentrated under reduced pressure and the residue was purified by RP-HPLC. The pure fractions were combined and concentrated to give compound 1169 (30 mg, 61% yield) as a white solid. $^1$H-NMR (DMSO-$d_6$): δ12.20-11.90 (broad s, 1H), 9.34 (s, 1H), 8.04 (s, 1H), 7.63 (dd, J=8.8, 2.5 Hz, 1H), 7.47 (d, J=2.5 Hz, 1H) 7.38 (s, 1H), 7.32-7.12 (m, 5H), 4.80 (s, 2H), 2.40 (m, 1H), 2.33 (m, 4H), 2.00 (s, 3H), 1.57 (s, 6H), 0.97 (m, 2H), 0.71 (m, 2H).

b) Compound 1177

To a solution of the TFA salt of compound 1168 (30 mg, 46 μmol) in $CH_2Cl_2$ (2 mL) was added phenyl chloroformate (8.8 mg, 56 μmol) and pyridine (9.0 μL, 0.11 mmol). The reaction mixture was stirred at room temperature for 1 h, and the volatiles were removed under reduced pressure. Isonipecotic acid (36 mg, 0.28 mmol) and $Et_3N$ (55 μL, 0.39 mmol) were added to a solution of the residue in DMSO (2 mL). The reaction mixture was heated at 65° C. for 3 h and upon cooling the mixture was purified by RP-HPLC. The pure fractions were combined and concentrated to give compound 1177 (13 mg, 41% yield) as a white solid. $^1$H-NMR (DMSO-$d_6$): δ 12.50-11.80 (bs, 1H), 9.26 (s, 1H), 7.56 (dd, J=8.9, 2.8 Hz, 1H), 7.40 (d, J=2.8 Hz, 1H), 7.31 (s, 1H), 7.25-7.18 (m, 2H), 7.18-7.06 (m, 3H), 6.32 (s, 1H), 4.72 (s, 2H), 3.80 (d, J=13.1 Hz, 1H), 2.66 (t, J=11.0 Hz, 2H), 2.37-2.22 (m, 1H), 2.03-1.85 (m, 1H), 1.92 (s, 3H), 1.77-1.62 (d, J=12.7 Hz, 2H) 1.50 (s, 6H), 1.42-1.23 (m, 2H), 0.97-0.76 (m, 2H), 0.69-0.58 (m, 2H).

Example 16

(Entry 1028)

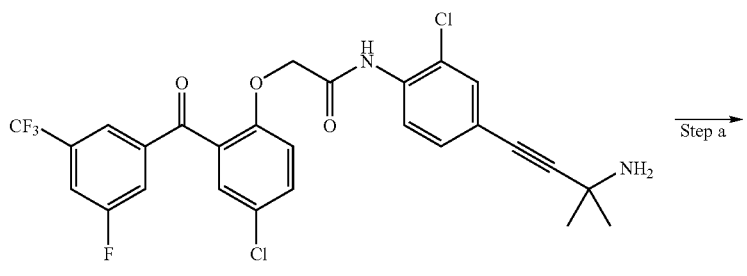

compound 1011

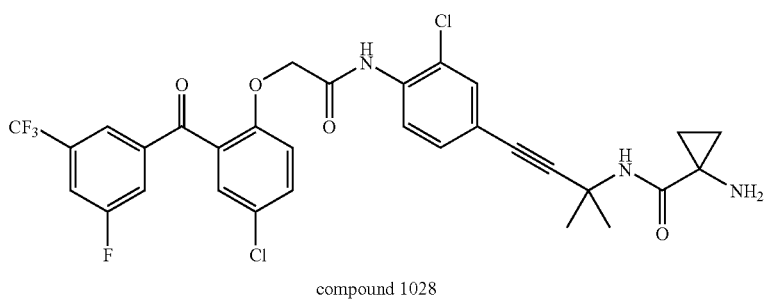

compound 1028 a) Compound 1028

A solution of the hydrochloride salt of compound 1011 (28.0 mg, 46.3 μmol; prepared using a method similar to the one described for compound 1168), Boc-1-aminocyclopropylcarboxylic acid (11.0 mg, 54.6 μmol), TBTU (18.0 mg, 56.1 μmol) and $Et_3N$ (30.0 μL, 215 μmol) in MeCN (0.5 mL) was stirred at room temperature for 1.5 h. A 4.0 N HCl solution in 1,4-dioxane (1.0 mL) was then added and the reaction mixture was stirred at room temperature for 0.5 h. The reaction mixture was concentrated under reduced pressure and the residue was purified by RP-HPLC. The pure fractions were combined and lyophilized to give the TFA salt of compound 1028 (2.2 mg, 7.4% yield) as a white solid. $^1$H-NMR (DMSO-$d_6$): δ 9.31 (s, 1H), 8.42 (broad s, 3H), 8.00 (broad d, J=8.4 Hz, 1H), 7.81-7.89 (m, 3H), 7.67 (dd, J=9.0, 2.8 Hz, 1H), 7.56 (d, J=2.6 Hz, 1H), 7.47 (broad s, 1H), 7.44 (d, J=1.8 Hz, 1H), 7.29 (dd, J=8.4, 1.8 Hz, 1H), 7.25 (d, J=9.0 Hz, 1H), 4.83 (s, 2H), 1.59 (s, 6H), 1.48-1.52 (m, 2H), 1.18-1.21 (m, 2H).

Example 17

(Entry 1082)

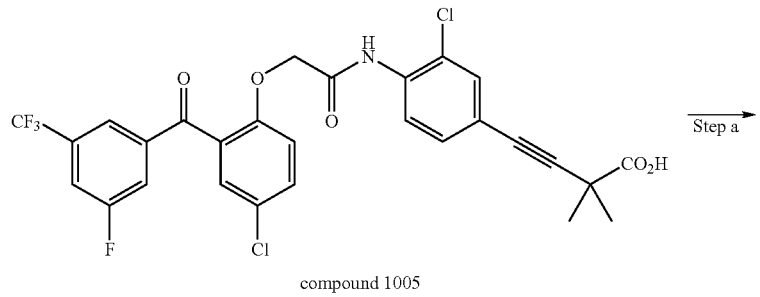
compound 1005

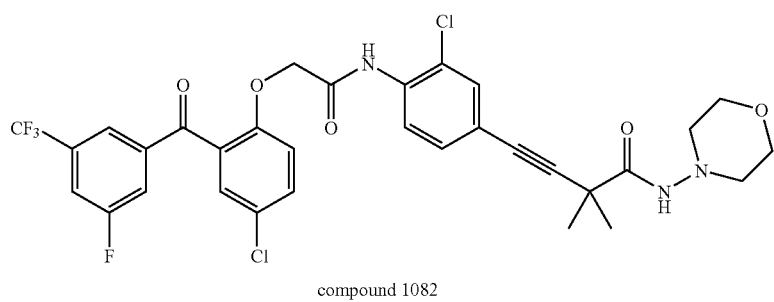
compound 1082 a) Compound 1082

To an ice-cold solution of compound 1005 (50.0 mg, 83.8 μmol) and DMF (5 μL) in $CH_2Cl_2$ (0.5 mL) was added $(COCl)_2$ (36.5 μL, 419 μmol). The reaction mixture was stirred at room temperature for 1 h then was concentrated under reduced pressure. 4-Aminomorpholine (9.7 μL, 101 μmol) and 2,6-lutidine (50.0 μL, 429 μL) were added to a solution of the residue in MeCN (0.5 mL). The reaction mixture was stirred at room temperature for 30 min then was purified by RP-HPLC. The pure fractions were combined and lyophilized to give compound 1082 (31 mg, 57% yield) as a white solid. $^1$H-NMR (DMSO-$d_6$): δ 9.33 (s, 1H), 8.88 (s, 3H), 8.00 (broad d, J=8.4 Hz, 1H), 7.86-7.89 (m, 2H), 7.82 (d, J=8.6 Hz, 1H), 7.67 (dd, J=9.0, 2.8 Hz, 1H), 7.59 (s, 1H), 7.56 (d, J=1.8 Hz, 1H), 7.38 (broad d, J=8.6 Hz, 1H), 7.25 (d, J=9.0 Hz, 1H), 4.83 (s, 2H), 3.61 (m, 4H), 2.83 (m, 4H), 1.40 (s, 6H).

Example 18

(Entry 2013)

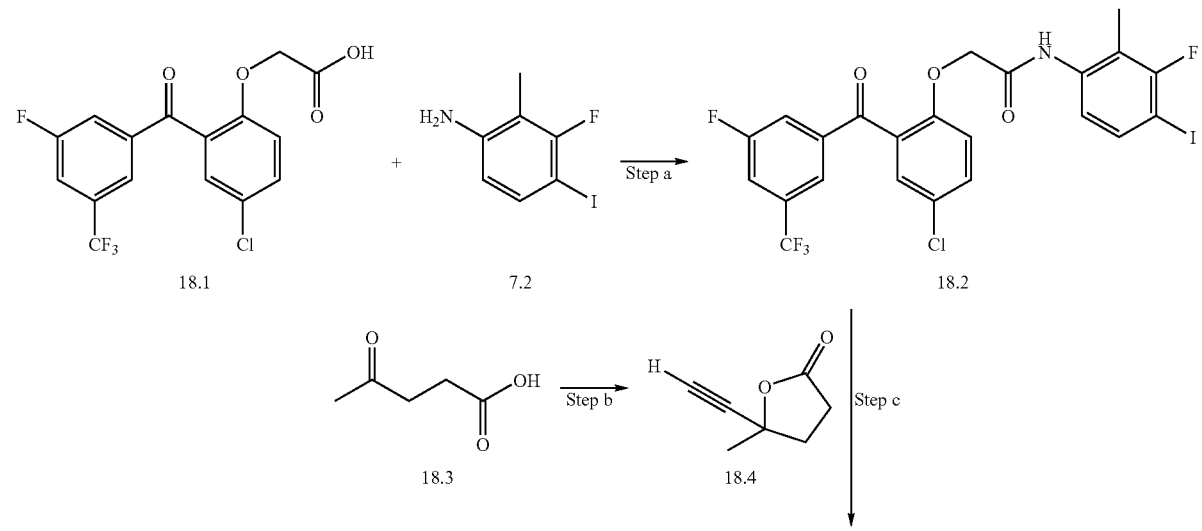

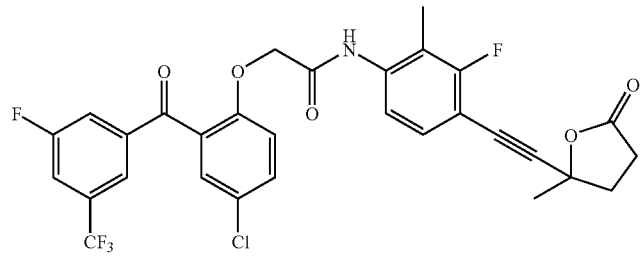

compound 2013 a) Compound 18.2

PCl$_3$ (46.8 µL, 527 µmol) was added to a solution of compound 18.1 (120 mg, 318 µmol; prepared using a procedure similar to the one described in steps b to e of Example 1, but using 3-fluoro-5-trifluoromethylbenzoyl chloride in place of the acid chloride of compound 1.2), compound 7.2 (from Example 7) (88.1 mg, 351 µmol) and pyridine (100 µL, 1.24 mmol) in CH$_2$Cl$_2$ (2.0 mL) at room temperature. The reaction mixture was stirred at room temperature for 1 h then was concentrated under reduced pressure. The residue was purified by flash chromatography (hexane/EtOAc, 80/20 to 50/50) to give compound 18.2 (150 mg, 77% yield) as a white solid.

b) Compound 18.4

A 0.5 M ethynylmagnesium bromide solution in THF (43.1 mL, 21.5 mmol) was added over 10 min to a cold (−20° C.) solution of compound 18.3 (1.00 g, 8.61 mmol) in THF (40 mL). The reaction mixture was stirred at −20° C. for 1 h then was allowed to warm to room temperature. Aqueous 1.0 N HCl solution was added and the mixture was extracted with Et$_2$O (3×). The combined organic layers were dried (MgSO$_4$), filtered and concentrated under reduced pressure. An ethereal CH$_2$N$_2$ solution (ca. 0.6 M; 25 mL) was added to a solution of the residue in CH$_2$Cl$_2$ (65 mL). The reaction mixture was stirred at room temperature for 5 min. Silica gel was added and the mixture was filtered through a pad of diatomaceous earth and concentrated under reduced pressure. The residue was purified by flash chromatography (hexane/EtOAc, 90/10 to 60/40) to give compound 18.4 (400 mg, 37% yield) as a white solid.

c) Compound 2013

A mixture of compound 18.2 (75.0 mg, 123 µmol), CuI (10.0 mg, 52.6 µmol), Et$_3$N (55.9 µL, 400 µmol) and compound 18.4 (20.0 mg, 161 µmol) in THF (3.0 mL) was degassed by bubbling argon through the solution for 15 min. Pd(PPh$_3$)$_4$ (23.5 mg, 20.0 µmol) was added and the reaction mixture was heated at reflux for 18 h. The black solution was concentrated under reduced pressure. The crude compound was purified by flash chromatography (hexane/EtOAc, 80/20 to 50/50) to afford compound 2013 (35 mg, 47% yield) as a beige solid. $^1$H-NMR (DMSO-d$_6$): δ 9.48 (s, 1H), 8.00 (d, J=8.6 Hz, 1H), 7.88 (s, 1H), 7.87 (d, J=8.6 Hz, 1H), 7.66 (dd, J=9.0, 2.6 Hz, 1H), 7.54 (d, J=2.6 Hz, 1H), 7.34-7.33 (m, 2H), 7.23 (d, J=9.0 Hz, 1H), 4.79 (s, 2H), 2.80-2.59 (m, 3H), 2.40-2.29 (m, 1H), 2.00 (s, 3H), 1.72 (s, 3H).

Example 19

Reverse Transcriptase (RT) Assays Enzymatic Assay (IC$_{50}$)

The enzymatic assay employed is described as follows: The reverse transcriptase (RT) enzyme assay has been adapted to a 96-well microtiter plate format and uses PicoGreen™ as a fluorescent intercalator. More explicitly, the HIV-1 RT enzyme was thawed and appropriately diluted into Tris/HCl 50 mM pH 7.8 containing NaCl 60 mM, MgCl$_2$.6H$_2$O 2 mM, DTT 6 mM, GSH 2 mM and 0.02% w/v CHAPS to give ≈10 nM enzyme. To 10 µL of this enzyme solution was added 10 µL of inhibitor solution (40 µM to 2.032 nM inhibitor in the same assay buffer as above containing 4% v/v DMSO). The plate was pre-incubated for 15 minutes at room temperature before proceeding to the next step. In this pre-incubation step, the highest and lowest inhibitor concentrations were 20 µM and 1.016 nM respectively and the concentration of DMSO was 2% v/v. Then the enzymatic reaction was initiated by addition of 20 µL of substrate solution. The final reaction mixture contained Tris/HCl 50 mM pH 7.8, NaCl 60 mM, MgCl$_2$.6H$_2$O 2 mM, DTT 6 mM, GSH 2 mM, CHAPS 0.02% w/v, DMSO 1% v/v, poly rC 45 nM, dG$_{15}$ 4.5 nM, dGTP 3.6 µM, and =≈2.5 nM enzyme. In this incubation step, the highest and lowest inhibitor concentrations were 10 µM and 0.508 nM respectively. After addition of the substrate cocktail, the plate was covered with a plastic seal and incubated for 50 minutes at 37° C. in a dry incubator. The reaction was then quenched by addition of 5 µL of EDTA 0.5 M. The plate was shaken for 30 seconds at medium speed and incubated for 5 minutes at room temperature. Then 160 µL of PicoGreen™ 1:400 dilution from commercial stock (diluted in Tris 20 mM pH 7.5 with EDTA 1 mM) was added and the plate was shaken for 30 seconds and incubated for 10 minutes at room temperature. The plate was then analyzed using a POLARstar Galaxy fluorometer (BMG Labtechnologies) with $\lambda_{ex}$ and $\lambda_{em}$ of 485 nm and 520 nm respectively. Each well was read for 1.25 second. Each row contained at its extremities a blank and a control well.

P24 Cellular Assay (EC$_{50}$)

The p24 assay is as described in WO 01/96338, pages 59-60.

C8166 HIV-1 Luciferase Assay (EC$_{50}$)

The luciferase assay is as described in WO 2004/050643, pages 73-75.

TABLES

Tables 1 to 2 illustrate further compounds of the present invention, which can be synthesized by methods analogous to those described hereinbefore, optionally modified by procedures known to the one skilled in the art. All compounds shown in the table are active in at least one of the assays described in Example 19.

Retention times ($t_R$) for each compound were measured using the standard analytical HPLC conditions described in the Examples. As is well known to one skilled in the art, retention time values are sensitive to the specific measurement conditions. Therefore, even if identical conditions of solvent, flow rate, linear gradient, and the like are used, the retention time values may vary when measured, for example, on different HPLC instruments. Even when measured on the same instrument, the values may vary when measured, for example, using different individual HPLC columns, or, when measured on the same instrument and the same individual column, the values may vary, for example, between individual measurements taken on different occasions.

TABLE 1

| Cpd | $R^1$ | $R^2$ | $R^4$ | $R^5$ | $R^{8a}$ | $t_R$ (min) | MS (MH$^+$) |
|---|---|---|---|---|---|---|---|
| 1001 | F | $CF_3$ | Me | H | —OH | 8.2 | 548.2 550.2 |
| 1002 | F | $CF_3$ | Cl | H | —OH | 8.6 | 568.1 570.1 572.1 |
| 1003 | F | $CF_3$ | Me | H | —O—$CH_2CO_2H$ | 8.0 | 604.0 606.0 (M − H)$^-$ |
| 1004 | Cl | CN | Cl | H | —OH | 8.0 | 539.0 541.0 543.0 (M − H)$^-$ |
| 1005 | F | $CF_3$ | Cl | H | —$CO_2H$ | 8.8 | 595.9 598.0 560.0 (M − H)$^-$ |
| 1006 | F | $CF_3$ | Me | H | —$CO_2H$ | 8.3 | 576.0 578.0 |
| 1007 | Cl | CN | Me | H | —$CO_2H$ | 7.6 | 547.0 549.0 551.0 |
| 1008 | Cl | CN | Cl | H | —$CO_2H$ | 8.2 | 569.0 571.0 573.0 |
| 1009 | F | $CF_3$ | Cl | H | —NH—CO—$CH_2$—N(Me)$_2$ | 6.8 | 652.0 654.0 |
| 1010 | F | $CF_3$ | Cl | H | (pyridine N-oxide carboxamide) | 7.8 | 688.0 690.0 |
| 1011 | F | $CF_3$ | Cl | H | —$NH_2$ | 6.5 | 564.9 566.9 568.9 (M − H)$^-$ |
| 1012 | Cl | CN | Cl | H | —$NH_2$ | 6.1 | 537.9 539.9 541.9 (M − H)$^-$ |
| 1013 | Cl | CN | Cl | H | —NH—CO—$CH_2$—N(Me)$_2$ | 6.4 | 625.0 627.0 629.0 |

TABLE 1-continued

| Cpd | R¹ | R² | R⁴ | R⁵ | R⁸ᵃ | $t_R$ (min) | MS (MH⁺) |
|---|---|---|---|---|---|---|---|
| 1014 | Cl | CN | Cl | H | ![pyridine N-oxide carboxamide] | 7.1 | 661.0 663.0 665.0 |
| 1015 | Cl | CN | Me | H | —OH | 7.3 | 521.0 523.0 |
| 1016 | F | CF₃ | Cl | H | —O—CH₂CO₂H | 8.4 | 623.9 625.9 (M − H)⁻ |
| 1017 | Cl | CN | Me | H | —O—CH₂CO₂H | 7.3 | 577.0 579.0 (M − H)⁻ |
| 1018 | F | CF₃ | Me | H | —NH—CO—CH₂—N(Me)₂ | 6.6 | 632.1 634.1 |
| 1019 | F | CF₃ | Me | H | ![pyridine N-oxide carboxamide] | 7.3 | 668.0 670.0 |
| 1020 | Cl | CN | Me | H | —NH—CO—CH₂—N(Me)₂ | 6.2 | 605.0 607.0 |
| 1021 | Cl | CN | Me | H | ![pyridine N-oxide carboxamide] | 6.7 | 641.0 643.0 645.0 |
| 1022 | F | CF₃ | Cl | H | —NH—CO—CH₂—NH₂ | 6.6 | 624.0 626.0 |
| 1023 | F | CF₃ | Cl | H | —NH—CO—CH₂—NHMe | 6.7 | 638.1 640.1 642.1 |
| 1024 | F | CF₃ | Me | F | —NH₂ | 6.4 | 563.1 565.1 (M − H)⁻ |
| 1025 | F | CF₃ | Me | F | —NH—CO—CH₂—N(Me)₂ | 6.7 | 650.2 656.2 |
| 1026 | F | CF₃ | Me | F | ![pyridine N-oxide carboxamide] | 7.4 | 686.2 688.2 |
| 1027 | F | CF₃ | Cl | H | —NH—COC(Me)₂—NH₂ | 6.8 | 652.2 654.2 656.2 |

TABLE 1-continued

| Cpd | R¹ | R² | R⁴ | R⁵ | R⁸ᵃ | $t_R$ (min) | MS (MH⁺) |
|---|---|---|---|---|---|---|---|
| 1028 | F | CF₃ | Cl | H | (1-amino-cyclopropyl-carboxamide group) | 6.7 | 50.2 652.2 654.2 |
| 1029 | F | CF₃ | Cl | H | (piperazinyl-acetamide group) | 7.1 | 736.3 738.3 740.3 |
| 1030 | F | CF₃ | Cl | H | (pyridinyl-N-oxide amino-acetamide group) | 7.4 | 717.2 719.2 721.2 |
| 1031 | F | CF₃ | Cl | H | (piperidine-4-carboxylic acid acetamide group) | 7.1 | 736.3 738.3 740.3 |
| 1032 | F | CF₃ | Cl | H | —NH—CO—CH₂CO₂H | 8.3 | 653.2 655.2 657.0 |
| 1033 | F | CF₃ | Cl | H | —NH—CO—CHMeCO₂H | 8.5 | 667.2 669.0 671.0 |
| 1034 | F | CF₃ | Cl | H | (piperidine-4-carboxylic acid amide group) | 8.5 | 707.2 709.2 711.2 |
| 1035 | F | CF₃ | Cl | H | —NH—CH₂CO₂H | 6.5 | 623.1 626.1 627.1 |
| 1036 | Br | OCF₃ | Cl | H | —CO₂H | 8.8 | 672.0 674.0 676.0 |
| 1037 | Br | OCF₃ | Cl | F | —CO₂H | 8.9 | 690.0 692.0 694.0 |
| 1038 | F | CF₃ | Cl | H | —CO—NH—CH₂CO₂H | 8.0 | 653.1 655.1 657.1 |
| 1039 | F | CF₃ | Cl | H | (alanine amide group) | 8.4 | 667.1 669.1 671.1 |

TABLE 1-continued

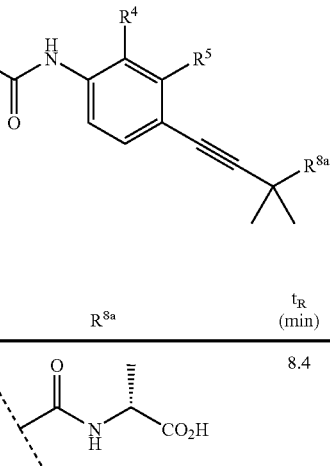

| Cpd | R$^1$ | R$^2$ | R$^4$ | R$^5$ | R$^{8a}$ | $t_R$ (min) | MS (MH$^+$) |
|---|---|---|---|---|---|---|---|
| 1040 | F | CF$_3$ | Cl | H | 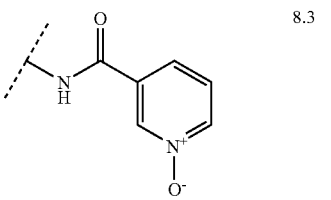 | 8.4 | 667.1<br>669.1<br>671.1 |
| 1041 | F | CF$_3$ | Cl | H | —CO—N(Me)—CH$_2$CO$_2$H | 8.2 | 667.2<br>669.2<br>671.2 |
| 1042 | F | CF$_3$ | Cl | H | —CO—NH—C(Me)$_2$CO$_2$H | 8.6 | 681.2<br>683.2<br>685.2 |
| 1043 | F | CF$_3$ | Cl | F | —CO$_2$H | 9.3 | 612.0<br>614.0<br>616.0<br>(M − H)$^-$ |
| 1044 | F | CF$_3$ | Me | F | —CO$_2$H | 8.9 | 594.2<br>596.2 |
| 1045 | F | CF$_3$ | Cl | F | —NH$_2$ | 6.7 | 583.1<br>585.1<br>586.1<br>(M − H)$^-$ |
| 1046 | F | CF$_3$ | Cl | F | —OH | 8.8 | 584.1<br>586.158<br>8.1<br>(M − H)$^-$ |
| 1047 | F | CF$_3$ | Me | F | —OH | 8.9 | 564.1<br>566.1<br>(M − H)$^-$ |
| 1048 | F | CF$_3$ | Cl | F | —O—CH$_2$CH$_2$OH | 8.3 | 628.1<br>630.1<br>632.1<br>(M − H)$^-$ |
| 1049 | F | CF$_3$ | Cl | F |  | 8.3 | 706.1<br>708.1<br>710.1 |
| 1050 | Br | CF$_3$ | Cl | H | —CO$_2$H | 8.7 | 654.0<br>656.0<br>658.0<br>(M − H)$^-$ |
| 1051 | Br | CF$_3$ | Cl | F | —CO$_2$H | 8.7 | 672.0<br>674.0<br>676.0<br>(M − H)$^-$ |
| 1052 | F | CF$_3$ | Cl | H | —NH—CO—C(Me)$_2$CO$_2$H | 8.8 | 681.2<br>683.2<br>685.0 |
| 1053 | F | CF$_3$ | Cl | H | —NH—COCH(Et)CO$_2$H | 8.7 | 681.2<br>683.2<br>685.0 |

TABLE 1-continued
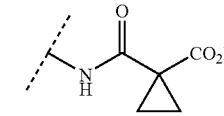
| Cpd | R$^1$ | R$^2$ | R$^4$ | R$^5$ | R$^{8a}$ | $t_R$ (min) | MS (MH$^+$) |
|---|---|---|---|---|---|---|---|
| 1054 | F | CF$_3$ | Cl | H | 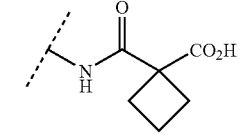 | 8.9 | 679.2 681.2 683.0 |
| 1055 | F | CF$_3$ | Cl | H | 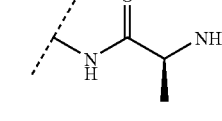 | 8.8 | 693.2 695.2 697.0 |
| 1056 | F | CF$_3$ | Cl | H | —NH—CO—(CH$_2$)$_2$CO$_2$H | 8.2 | 667.2 669.2 671.0 |
| 1057 | F | CF$_3$ | Cl | H | —NH—CO—CH$_2$C(Me)$_2$CO$_2$H | 8.7 | 695.2 697.3 699.0 |
| 1058 | F | CF$_3$ | Cl | F | —O—CH$_2$CO$_2$H | 9.1 | 642.1 644.1 646.1 (M − H)$^-$ |
| 1059 | F | CF$_3$ | Me | F | —O—CH$_2$CO$_2$H | 8.8 | 622.1 624.1 (M − H)$^-$ |
| 1060 | F | CF$_3$ | Cl | F | —CO—NHOH | 8.5 | 627.1 629.1 631.0 (M − H)$^-$ |
| 1061 | F | Br | Cl | H | —CO$_2$H | 8.4 | 604.0 606.0 608.0 (M − H)$^-$ |
| 1062 | F | Br | Cl | F | —CO$_2$H | 8.5 | 622.0 624.0 626.0 (M − H)$^-$ |
| 1063 | F | CF$_3$ | Cl | H | 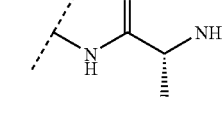 | 6.6 | 638.2 640.2 642.2 |
| 1064 | F | CF$_3$ | Cl | H | 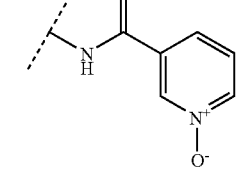 | 6.6 | 638.2 640.2 642.2 |
| 1065 | F | CF$_3$ | Cl | H |  | 7.6 | 688.2 690.2 692.2 |

TABLE 1-continued
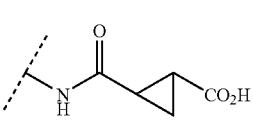
| Cpd | R$^1$ | R$^2$ | R$^4$ | R$^5$ | R$^{8a}$ | t$_R$ (min) | MS (MH$^+$) |
|---|---|---|---|---|---|---|---|
| 1066 | F | CF$_3$ | Cl | H | —NH—CO—C(Me)$_2$CH$_2$CO$_2$H | 8.7 | 695.2 697.2 699.0 |
| 1067 | F | CF$_3$ | Cl | H | 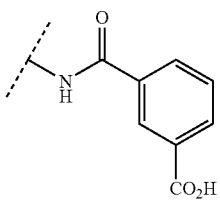 | 8.4 | 679.2 681.2 683.0 |
| 1068 | F | Br | Me | F | —CO$_2$H | 8.2 | 604.0 606.0 |
| 1069 | F | CF$_3$ | Cl | F | —NH—CO—(CH$_2$)$_3$—SO$_2$NH$_2$ | 8.5 | 634.1 736.1 738.1 |
| 1070 | F | CF$_3$ | Cl | F | 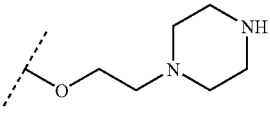 | 9.2 | 733.1 735.1 737.1 |
| 1071 | F | CF$_3$ | Cl | F | 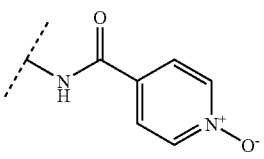 | 6.4 | 698.3 700.0 702.2 |
| 1072 | F | CF$_3$ | NO$_2$ | H | —NH$_2$ | 6.5 | 576.1 578.1 (M − H)$^-$ |
| 1073 | H | CN | Cl | H | —CO$_2$H | 7.5 | 533.0 535.0 537.0 (M − H)$^-$ |
| 1074 | H | CN | Me | F | —CO$_2$H | 7.3 | 531.1 533.1 (M − H)$^-$ |
| 1075 | Cl | CN | Me | F | —CO$_2$H | 7.2 | 565.0 567.0 569.0 (M − H)$^-$ |
| 1076 | F | CF$_3$ | NO$_2$ | H | —NH—CO—(CH$_2$)$_2$CO$_2$H | 7.9 | 678.2 680.0 |
| 1077 | F | CF$_3$ | NO$_2$ | H | (pyridine N-oxide carboxamide) | 7.8 | 699.2 701.1 |
| 1078 | F | CF$_3$ | NO$_2$ | H | —NH—CO—CH(Me)CO$_2$H | 8.1 | 678.2 680.2 |

TABLE 1-continued

| Cpd | $R^1$ | $R^2$ | $R^4$ | $R^5$ | $R^{8a}$ | $t_R$ (min) | MS (MH$^+$) |
|---|---|---|---|---|---|---|---|
| 1079 | Cl | CN | Cl | F | —O—CH$_2$—CO$_2$H | 7.3 | 615.0 617.0 619.0 (M − H)$^-$ |
| 1080 | Cl | CN | Me | F | —O—CH$_2$—CO$_2$H | 7.1 | 595.0 597.0 599.0 (M − H)$^-$ |
| 1081 | Cl | CN | Cl | F | —CO$_2$H | 7.5 | 585.0 587.0 589.0 591.0 (M − H)$^-$ |
| 1082 | F | CF$_3$ | Cl | H | morpholine amide | 7.5 | 680.1 682.1 684.1 |
| 1083 | F | CF$_3$ | Cl | H | (S)-2,3-dihydroxypropyl amide | 7.2 | 669.1 671.1 673.1 |
| 1084 | F | CF$_3$ | Cl | H | —CO—NH—(CH$_2$)$_2$—SO$_3$H | 6.7 | 701.0 703.0 705.0 (M − H)$^-$ |
| 1085 | F | CF$_3$ | Cl | H | —CH$_2$OH | 6.7 | 580.1 582.1 584.1 (M − H)$^-$ |
| 1086 | F | CF$_3$ | Cl | H | —CH$_2$O—CONH$_2$ | 9.3 | 623.0 625.0 627.0 (M − H)$^-$ |
| 1087 | Cl | CN | Cl | H | —NH—CO—CH$_2$NHMe | 6.2 | 611.0 613.0 615.0 617.0 |
| 1088 | Cl | CN | Cl | H | —NH—CO—C(Me)$_2$NH$_2$ | 6.3 | 625.2 627.2 629.2 630.2 |
| 1089 | F | Br | Me | F | —O—CH$_2$CO$_2$H | 8.8 | 631.9 633.9 635.9 (M − H)$^-$ |
| 1090 | F | Br | Me | F | —NH$_2$ | 6.5 | 573.0 575.0 577.0 (M − H)$^-$ |
| 1091 | F | CF$_3$ | NO$_2$ | H | —CO$_2$H | 8.7 | 607.0 609.0 |
| 1092 | Cl | CN | NO$_2$ | H | —CO$_2$H | 8.2 | 580.2 582.0 584.0 |

TABLE 1-continued

| Cpd | R¹ | R² | R⁴ | R⁵ | R⁸ᵃ | $t_R$ (min) | MS (MH⁺) |
|---|---|---|---|---|---|---|---|
| 1093 | F | Br | Me | F | (nicotinamide N-oxide group) | 8.0 | 696.0 698.0 700.0 |
| 1094 | Cl | CN | NO₂ | H | —NH₂ | 6.2 | 549.1 551.1 553.0 (M − H)⁻ |
| 1095 | F | CF₃ | Cl | F | —NH—CO—(CH₂)₂CO₂H | 8.2 | 685.1 687.1 689.0 |
| 1096 | F | CF₃ | Me | F | —NH—CO—(CH₂)₂CO₂H | 7.8 | 665.2 667.2 |
| 1097 | Cl | CN | NO₂ | H | —NH—CO—(CH₂)₂CO₂H | 7.2 | 651.2 653.2 655.0 |
| 1098 | F | Br | Me | F | —NH—CO—(CH₂)₂CO₂H | 8.1 | 675.1 677.1 679.1 |
| 1099 | F | CF₃ | Cl | H | —NH—CO—CH₂OH | 8.4 | 625.1 627.1 |
| 1100 | H | CN | Me | F | —O—CH₂—CO₂H | 7.3 | 561.2 563.2 (M − H)⁻ |
| 1101 | F | CF₃ | Cl | H | —NH—CO—Me | 8.7 | 609.1 611.1 |
| 1102 | F | CF₃ | Me | F | —NH—CO—CH₂NHMe | 6.5 | 636.2 638.2 |
| 1103 | F | CF₃ | Me | F | —NH—CO—C(Me)₂NH₂ | 6.5 | 650.2 652.2 |
| 1104 | Cl | CN | Cl | F | —NH—CO—CH₂CH₂CO₂H | 7.5 | 658.0 660.1 662.1 664.0 |
| 1105 | Cl | CN | Me | F | —NH—CO—CH₂CH₂CO₂H | 7.1 | 638.2 640.2 642.0 |
| 1106 | Cl | Br | Cl | F | —NH—CO—CH₂CH₂CO₂H | 8.7 | 711.0 713.0 715.0 717.0 |
| 1107 | Cl | Br | Me | F | —NH—CO—CH₂CH₂CO₂H | 8.3 | 691.1 693.1 695.1 697.0 |
| 1108 | Cl | CN | Cl | H | —NH—CH₂CO₂H | 6.0 | 596.0 598.0 600.0 (M − H)⁻ |
| 1109 | Cl | CN | Cl | H | —NH—CO—CH₂NH₂ | 6.1 | 597.1 599.1 601.1 603.1 |

TABLE 1-continued

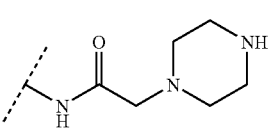

| Cpd | R$^1$ | R$^2$ | R$^4$ | R$^5$ | R$^{8a}$ | t$_R$ (min) | MS (MH$^+$) |
|---|---|---|---|---|---|---|---|
| 1110 | Cl | CN | Cl | F | —NH$_2$ | 6.1 | 556.0 558.0 560.0 562.0 (M − H)$^-$ |
| 1111 | Cl | CN | Me | F | —NH$_2$ | 5.9 | 536.1 538. 540.1 (M − H)$^-$ |
| 1112 | Cl | Br | Cl | F | —NH$_2$ | 6.7 | 608.9 610.9 612.9 614.9 (M − H)$^-$ |
| 1113 | Cl | Br | Me | F | —NH$_2$ | 6.6 | 589.0 591.0 593.0 (M − H)$^-$ |
| 1114 | CN | CF$_3$ | Cl | H | —CO$_2$H | 7.9 | 603.0 605.0 |
| 1115 | cPr | Br | Cl | H | —CO$_2$H | 9.6 | 630.0 632.0 634.0 |
| 1116 | cPr | Br | Me | F | —CO$_2$H | 9.2 | 628.1 630.1 |
| 1117 | cPr | Br | Me | F | —O—CH$_2$CO$_2$H | 8.9 | 656.0 658.0 (M − H)$^-$ |
| 1118 | cPr | Br | Cl | F | —O—CH$_2$CO$_2$H | 9.5 | 676.0 678.0 680.0 (M − H)$^-$ |
| 1119 | cPr | CN | Me | F | —O—CH$_2$CO$_2$H | 8.3 | 601.1 603.1 (M − H)$^-$ |
| 1120 | cPr | CN | Me | F | —CO$_2$H | 8.6 | 571.1 573.1 (M − H)$^-$ |
| 1121 | F | CN | Me | F | —CO$_2$H | 7.4 | 549.1 551.1 (M − H)$^-$ |
| 1122 | Cl | CN | Cl | H | 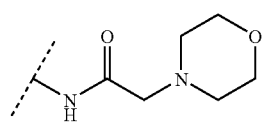 | 5.9 | 666.1 668.1 670.1 672.1 |
| 1123 | Cl | CN | Cl | H |  | 6.3 | 667.1 669.1 671.1 673.1 |
| 1124 | Cl | CN | Cl | H | —NH—COCH$_2$NH(CH$_2$)$_2$OMe | 6.4 | 655.1 657.1 659.1 661.1 |

TABLE 1-continued

| Cpd | R¹ | R² | R⁴ | R⁵ | R⁸ᵃ | $t_R$ (min) | MS (MH⁺) |
|---|---|---|---|---|---|---|---|
| 1125 | Cl | CN | Cl | F | —NH—CO—CH₂NHMe | 6.3 | 629.2 631.2 633.2 635.2 |
| 1126 | Cl | CN | Me | F | —NH—CO—CH₂NHMe | 6.1 | 609.2 611.2 613.2 |
| 1127 | Cl | Br | Cl | F | —NH—CO—CH₂NHMe | 7.0 | 682.1 684.1 686.0 688.0 |
| 1128 | Cl | Br | Me | F | —NH—CO—CH₂NHMe | 6.7 | 662.1 664.1 666.1 |
| 1129 | F | CF₃ | Cl | H | ⸺NH—CO—CH=CH—CO₂H | 8.3 | 665.1 667.1 669.0 |
| 1130 | Cl | CN | Cl | H | ⸺NH—CO—CH=CH—CO₂H | 7.7 | 638.0 640.1 642.1 644.0 |
| 1131 | F | Br | Cl | H | ⸺NH—CO—CH=CH—CO₂H | 8.4 | 675.1 677.1 679.1 681.0 |
| 1132 | Cl | CN | Cl | H | —NH—CO—(CH₂)₂CO₂H | 7.3 | 640.0 642.2 644.1 646.0 |
| 1133 | F | Br | Cl | H | —NH—CO—(CH₂)₂CO₂H | 8.1 | 677.1 679.1 681.1 683.0 |
| 1134 | Cl | Br | Cl | H | —NH₂ | 6.7 | 591.0 593.0 595.0 597.0 (M − H)⁻ |
| 1135 | F | Cl | Me | F | —CO₂H | 8.0 | 560.1 562.0 |
| 1136 | F | cPr | Me | F | —CO₂H | 9.0 | 566.2 568.2 |
| 1137 | F | cPr | Cl | F | —CO₂H | 8.8 | 568.1 588.1 590.1 |
| 1138 | F | cPr | Me | F | —O—CH₂CO₂H | 8.8 | 594.2 596.2 (M − H)⁻ |
| 1139 | Br | Br | Me | F | —CO₂H | 8.9 | 666.0 668.0 |
| 1140 | F | cPr | Cl | F | —O—CH₂CO₂H | 9.1 | 614.1 616.1 618.1 (M − H)⁻ |

TABLE 1-continued

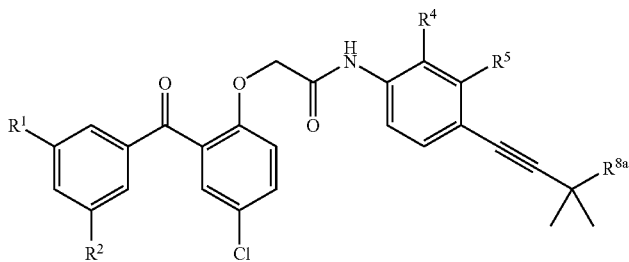

| Cpd | R$^1$ | R$^2$ | R$^4$ | R$^5$ | R$^{8a}$ | t$_R$ (min) | MS (MH$^+$) |
|---|---|---|---|---|---|---|---|
| 1141 | Cl | Br | Me | H | —CO$_2$H | 7.8 | 602.0<br>604.0<br>606.0<br>608.0 |
| 1142 | Cl | Br | Cl | F | —CO$_2$H | 8.1 | 637.9<br>639.9<br>641.9<br>643.9<br>(M − H)$^-$ |
| 1143 | Cl | Br | Me | F | —CO$_2$H | 7.8 | 620.0<br>622.0<br>624.0<br>626.0 |
| 1144 | Cl | Br | Cl | H | —CO$_2$H | 8.1 | 621.9<br>623.9<br>625.9<br>627.9 |
| 1145 | F | CN | Me | F | —O—CH$_2$CO$_2$H | 7.2 | 579.0<br>581.0<br>(M − H)$^-$ |
| 1146 | CN | CF$_3$ | Me | F | —CO$_2$H | 7.7 | 599.0<br>601.0<br>(M − H)$^-$ |
| 1147 | Br | CN | Me | F | —CO$_2$H | 8.4 | 611.0<br>613.0<br>615.0 |
| 1148 | Cl | Br | Cl | H | —NH—CH$_2$CO$_2$H | 6.7 | 648.9<br>651.0<br>653.0<br>655.0<br>(M − H)$^-$ |
| 1149 | Cl | CN | Me | F | —NH—CH$_2$CO$_2$H | 5.9 | 594.1<br>596.1<br>598.1<br>(M − H)$^-$ |
| 1150 | Cl | Br | Cl | F | —NH—CH$_2$CO$_2$H | 6.7 | 666.9<br>668.9<br>670.9<br>672.9<br>(M − H)$^-$ |
| 1151 | Cl | Br | Me | F | —NH—CH$_2$CO$_2$H | 6.6 | 647.0<br>649.0<br>651.0<br>653.0<br>(M − H)$^-$ |
| 1152 | Cl | Br | Cl | H | —NH—CO—C(Me)$_2$NH$_2$ | 6.9 | 678.1<br>680.1<br>682.1<br>684.1 |
| 1153 | Cl | CN | Cl | H | ⸺N(H)—C(=O)—CH$_2$—N(H)—CH$_2$—CO$_2$H | 6.2 | 657.0<br>658.9 |
| 1154 | F | OMe | Me | F | —CO$_2$H | 7.7 | 556.2<br>558.2 |

TABLE 1-continued

| Cpd | R¹ | R² | R⁴ | R⁵ | R⁸ᵃ | $t_R$ (min) | MS (MH⁺) |
|---|---|---|---|---|---|---|---|
| 1155 | F | (OCH₂CO₂Me, dashed bond) | Me | F | —CO₂H | 7.4 | 614.2 / 616.2 |
| 1156 | H | Br | Me | F | —CO₂H | 7.9 | 584.1 / 586.1 (M − H)⁻ |
| 1157 | F | CF₃ | Me | F | (3-CO₂H-pyridin-2-yl)C(O)NH— | 8.5 | 714.2 / 716.2 |
| 1158 | F | CF₃ | Me | F | (3-CO₂H-pyridin-2-yl)C(O)NH— | 7.5 | 712.2 / 714.2 (M − H)⁻ |
| 1159 | F | Cl | Me | F | —NH—CO—(CH₂)₂CO₂H | 7.4 | 631.1 / 633.1 |
| 1160 | F | CN | Me | F | —NH—CO—(CH₂)₂CO₂H | 6.8 | 622.3 / 624.3 |
| 1161 | H | cPr | Me | F | —CO₂H | 9.0 | 548.2 / 550.2 |
| 1162 | H | cPr | Me | F | —O—CH₂CO₂H | 8.5 | 576.2 / 578.2 (M − H)⁻ |
| 1163 | F | OMe | Me | F | —NH—CO—(CH₂)₂CO₂H | 7.1 | 627.2 / 629.2 |
| 1164 | F | CONH₂ | Me | F | —CO₂H | 6.4 | 569.2 / 571.2 |
| 1165 | Br | CF₃ | Me | F | —CO₂H | 8.2 | 654.1 / 656.1 |
| 1166 | Br | I | Me | F | —CO₂H | 9.3 | 714.0 / 716.0 |
| 1167 | Br | I | Me | F | —O—CH₂CO₂H | 9.1 | 742.0 / 744.0 (M − H)⁻ |
| 1168 | F | cPr | Me | F | —NH₂ | 6.5 | 535.2 / 537.2 (M − H)⁻ |
| 1169 | F | cPr | Me | F | —NH—CO—(CH₂)₂CO₂H | 8.0 | 637.2 / 639.2 |
| 1170 | cPr | CF₃ | Me | F | —O—CH₂CO₂H | 8.9 | 644.2 / 646.2 (M − H)⁻ |
| 1171 | cPr | CF₃ | Me | F | —CO₂H | 9.1 | 616.2 / 618.2 |
| 1172 | F | CF₃ | Me | F | —NH—CO—CH₂C(Me)₂CO₂H | 8.0 | 693.3 / 695.3 |

TABLE 1-continued

| Cpd | R¹ | R² | R⁴ | R⁵ | R⁸ᵃ | $t_R$ (min) | MS (MH⁺) |
|---|---|---|---|---|---|---|---|
| 1173 | F | CF₃ | Me | F | pyrrolidine-urea-CO₂H | 7.5 | 706.3 708.3 |
| 1174 | F | CF₃ | Me | F | azetidine-urea-CO₂H | 7.3 | 690.2 692.2 (M − H)⁻ |
| 1175 | F | CF₃ | Me | F | amide-(S)-Me-CO₂H | 7.6 | 679.3 681.3 |
| 1176 | F | CF₃ | Me | F | piperidine-urea-CO₂H | 7.6 | 720.0 722.0 |
| 1177 | F | cPr | Me | F | piperidine-urea-CO₂H | 7.6 | 692.3 694.3 |
| 1178 | F | CN | Me | F | piperidine-urea-CO₂H | 7.0 | 677.3 679.3 |
| 1179 | F | CN | Me | F | azetidine-urea-CO₂H | 6.7 | 649.3 651.3 |
| 1180 | F | CN | Me | F | amide-diMe-CO₂H | 6.9 | 650.2 652.0 |
| 1181 | F | CF₃ | Me | F | amide-(R)-Me-CO₂H | 7.5 | 679.3 681.3 |

TABLE 1-continued
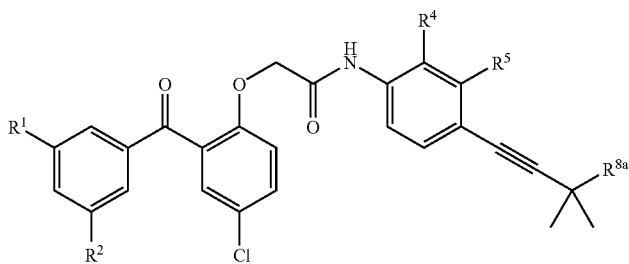
| Cpd | R[1] | R[2] | R[4] | R[5] | R[8a] | $t_R$ (min) | MS (MH+) |
|---|---|---|---|---|---|---|---|
| 1182 | F | CF$_3$ | Me | F | | 7.5 | 679.3 681.3 |
| 1183 | F | CN | Me | F | | 6.6 | 636.3 638.3 |
| 1184 | F | CN | Me | F | | 6.6 | 636.3 638.3 |
| 1185 | F | CN | Me | F | | 6.8 | 671.0 673.0 |
TABLE 2
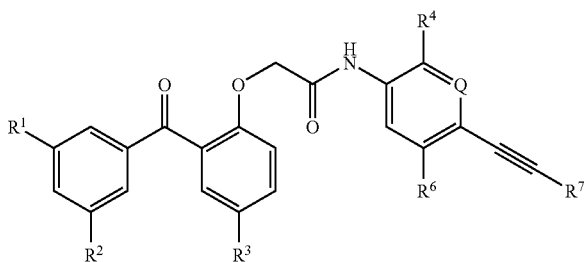
| Cpd | R[1] | R[2] | R[3] | R[4] | Q | R[6] | R[7] | $t_R$ (min) | MS (MH+) |
|---|---|---|---|---|---|---|---|---|---|
| 2001 | F | CF$_3$ | Cl | Cl | CH | H | —CH$_2$CH$_2$OH | 8.7 | 554.1 556.0 558.0 |
| 2002 | F | CF$_3$ | Cl | Cl | CH | H | —C(CF$_3$)$_2$OH | 9.0 | 674.0 676.0 (M − H)− |
| 2003 | F | CF$_3$ | Cl | Cl | CH | F | —C(Me)$_2$NH$_2$ | 6.7 | 583.1 585.1 587.0 (M − H)− |

TABLE 2-continued
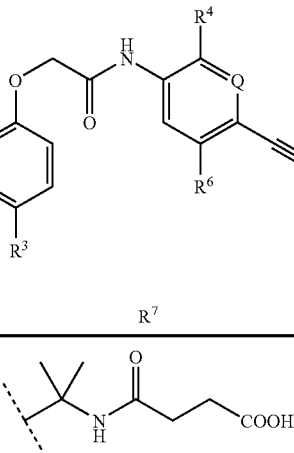
| Cpd | R¹ | R² | R³ | R⁴ | Q | R⁶ | R⁷ | $t_R$ (min) | MS (MH⁺) |
|---|---|---|---|---|---|---|---|---|---|
| 2004 | F | CF₃ | Cl | Cl | CH | F | 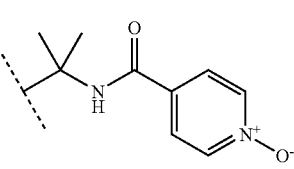 | 8.3 | 685.1 687.1 689.0 |
| 2005 | F | CF₃ | Cl | Cl | CH | F | 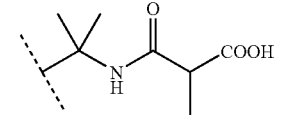 | 8.3 | 706.1 708.1 710.0 |
| 2006 | F | CF₃ | Cl | Cl | CH | F | 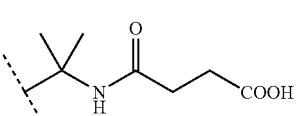 | 8.6 | 685.1 687.1 689.0 |
| 2007 | F | CF₃ | Cl | Cl | CH | H | —C(Me)OH—CO₂H | 7.9 | 598.0 600.0 |
| 2008 | F | CF₃ | Cl | Cl | CH | F | —C(Me)₂CO₂H | 9.1 | 614.1 616.0 618.0 |
| 2009 | Cl | CN | Cl | Cl | CH | F | —C(Me)₂CO₂H | 8.6 | 587.0 589.1 591.0 593.0 |
| 2010 | Cl | CN | Cl | Cl | CH | F | —C(Me)₂NH₂ | 6.3 | 556.0 558.1 560.1 (M − H)⁻ |
| 2011 | Cl | CN | Cl | Cl | CH | F | 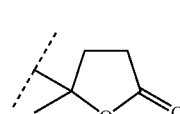 | 7.6 | 658.1 660.0 662.0 |
| 2012 | F | CF₃ | Cl | Cl | CH | H | 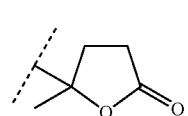 | 8.4 | 608.0 610.0 |
| 2013 | F | CF₃ | Cl | Me | CF | H | | 8.2 | 606.1 608.1 |
| 2014 | F | Br | F | Me | CF | H | —C(Me)₂CO₂H | 7.7 | 588.1 590.1 |
| 2015 | F | CF₃ | Cl | Me | N | H | —C(Me)₂CO₂H | 7.1 | 577.1 579.1 |
| 2016 | F | CN | F | Me | CF | H | —C(Me)₂CO₂H | 6.9 | 533.2 534.1 535.1 (M − H)⁻ |

What is claimed is:

1. A compound of formula (I):

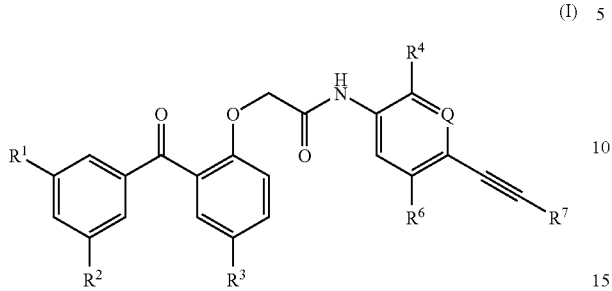

wherein
$R^1$ and $R^2$ are each independently selected from H, halo, cyano, $(C_{1-4})$alkyl, $(C_{2-4})$alkenyl, $(C_{2-4})$alkynyl, $(C_{3-6})$cycloalkyl, —O—$(C_{1-4})$alkyl, —COO$(C_{1-4})$alkyl, —CONH$_2$, —CONH$(C_{1-4})$alkyl and —CON$((C_{1-4})$alkyl)$_2$; wherein said $(C_{1-4})$alkyl is optionally substituted with one, two or three halo substituents; and wherein said —O—$(C_{1-4})$alkyl is optionally substituted with —COO$(C_{1-4})$alkyl or one, two or three halo substituents;

with the proviso that when $R^1$ is H, $R^2$ cannot be H;

$R^3$ is selected from H and halo;

$R^4$ is selected from $(C_{1-4})$alkyl, halo and nitro;

Q is selected from N and $CR^5$; wherein $R^5$ is selected from H and halo;

$R^6$ is selected from H and halo;

$R^7$ is selected from —$(C_{1-6})$alkyl-$R^8$ and a 5-membered saturated heterocycle containing one heteroatom selected from N, O and S;

wherein said heterocycle is optionally substituted with one, two or three substituents each independently selected from $(C_{1-6})$alkyl and oxo; and wherein the $(C_{1-6})$alkyl portion of said —$(C^{1-6})$alkyl-$R^8$ is optionally monosubstituted with —OH and optionally substituted with from one to six halo substituents; and wherein $R^8$ is selected from:

a) —OH, —COOH, —CONHSO$_2R^9$, —C(=O)NHOH, —OC(=O)NH$_2$ or —NH$_2$, wherein $R^9$ is $(C_{1-6})$alkyl or $(C_{3-7})$cycloalkyl;

b) —O—$(C_{2-6})$alkyl-OH, —NH—$(C_{2-6})$alkyl-OH, —O—$(C^{1-6})$alkyl-$R^{81}$ or —NH—$(C_{1-6})$alkyl-$R^{81}$, wherein $R^{81}$ is selected from Het, —CONHSO$_2R^9$, and —COOH; wherein $R^9$ is as defined above;

c) —NHC(=O)—$R^{82}$, wherein $R^{82}$ is selected from $(C_{1-6})$alkyl, $(C_{2-6})$alkenyl, $(C_{3-7})$cycloalkyl, phenyl, —NH$_2$, —NH$(C_{1-6})$alkyl, —N$((C_{1-6})$alkyl)$_2$ and Het; each of said $(C_{1-6})$alkyl, $(C_{2-6})$alkenyl, $(C_{3-7})$cycloalkyl, phenyl and Het being optionally substituted with one or more substituents each independently selected from —OH, —COOH, —CONHSO$_2R^9$, —SO$_2$NH$_2$, —NH$_2$, —NH$(C_{1-6})$alkyl, —N$((C_{1-6})$alkyl)$_2$, Het and —NH-Het; wherein $R^9$ is as defined above;

wherein the $(C_{1-6})$alkyl portions of said —NH$(C_{1-6})$alkyl and —N$((C_{1-6})$alkyl)$_2$ are each independently optionally substituted with —O$(C_{1-6})$alkyl, —CONHSO$_2R^9$, or —COOH; wherein $R^9$ is as defined above; and wherein said Het and the Het portion of said —NH-Het are each optionally substituted with —COOH or —CONHSO$_2R^9$; wherein $R^9$ is as defined above; and d) —C(=O)N$(R^{83})R^{84}$, wherein $R^{83}$ is selected from H and $(C_{1-6})$alkyl; and $R^{84}$ is selected from $(C_{1-6})$alkyl and Het, each of said $(C_{1-6})$alkyl and Het being optionally substituted with one or more substituents each independently selected from —OH, —COOH, —CONHSO$_2R^9$ and —SO$_3$H; wherein $R^9$ is as defined above;

or $R^{83}$ and $R^{84}$ are linked, together with the nitrogen atom to which they are bonded, to form a 5- or 6-membered monocyclic heterocycle which may be saturated, unsaturated or aromatic and which may optionally contain from one to three additional heteroatoms each independently selected from N, O and S; said heterocycle being optionally substituted with —COOH or —CONHSO$_2R^9$; wherein $R^9$ is as defined above;

wherein Het is a 4-, 5- or 6-membered heterocycle or a 9- or 10-membered heterobicycle, each of which may be saturated, unsaturated or aromatic and each of which may optionally contain from one to four heteroatoms each independently selected from N, O and S, wherein each said N heteroatom may, independently and where possible, exist in an oxidized state such that it is further bonded to an oxygen atom to form an N-oxide group and wherein each said S heteroatom may, independently and where possible, exist in an oxidized state such that it is further bonded to one or two oxygen atoms to form the groups SO or SO$_2$;

or a salt or ester thereof.

2. A compound according to claim 1 wherein $R^1$ and $R^2$ are each independently selected from H, halo, cyano, $(C_{1-4})$alkyl, $(C_{3-6})$cycloalkyl, —O—$(C_{1-4})$alkyl, —COO$(C_{1-4})$alkyl and —CONH$_2$; wherein said $(C_{1-4})$alkyl is optionally substituted with one, two or three halo substituents; and wherein said —O—$(C_{1-4})$alkyl is optionally substituted with —COO$(C_{1-4})$alkyl or one, two or three halo substituents.

3. A compound according to claim 1 wherein $R^3$ is chloro or fluoro.

4. A compound according to claim 1 wherein $R^4$ is selected from chloro, nitro and methyl.

5. A compound according to claim 1 wherein Q is N.

6. A compound according to claim 1 wherein Q is $CR^5$, wherein $R^5$ is H or halo.

7. A compound according to claim 1 wherein $R^6$ is H or fluoro.

8. A compound according to claim 1 wherein $R^7$ is a group of the formula

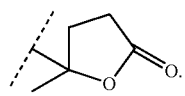

9. A compound according to claim 1 wherein $R^7$ is —$(C_{1-6})$alkyl-$R^8$;

wherein the $(C_{1-6})$alkyl portion of said —$(C_{1-6})$alkyl-$R^8$ is optionally monosubstituted with —OH and optionally substituted with from one to six halo substituents; and wherein $R^8$ is defined as in claim 1.

10. A compound according to claim 9 wherein $R^7$ is —$C(CH_3)_2$—$R^8$.

11. A compound according to claim 9 wherein $R^8$ is selected from:
  a) —OH, —COOH, —C(=O)NHOH, —OC(=O)NH$_2$ or —NH$_2$;
  b) —O—(C$_{2-3}$)alkyl-OH, —NH—(C$_{2-3}$)alkyl —OH, —O—(C$_{1-3}$)alkyl-R$^{81}$ or —NH—(C$_{1-3}$)alkyl -R$^{81}$, wherein R$^{81}$ is —COOH or a 6-membered saturated heterocycle containing one N heteroatom and optionally one additional heteroatom selected from N, O and S;
  c) —NHC(=O)—R$^{82}$, wherein R$^{82}$ is selected from (C$_{1-4}$)alkyl, (C$_{2-4}$)alkenyl, (C$_{3-6}$)cycloalkyl, phenyl and a 4-, 5- or 6-membered heterocycle which is saturated, unsaturated or aromatic and which contains one N heteroatom and optionally one additional heteroatom selected from N, O and S, wherein each said N heteroatom may, independently and where possible, exist in an oxidized state such that it is further bonded to an oxygen atom to form an N-oxide group;
    each of said (C$_{1-4}$)alkyl, (C$_{2-4}$)alkenyl, (C$_{3-6}$)cycloalkyl, phenyl and 4-, 5- or 6-membered heterocycle being optionally substituted with one or more substituents each independently selected from —OH, —COOH, —SO$_2$NH$_2$, —NH$_2$, —NH(C$_{1-3}$)alkyl, —N((C$_{1-3}$)alkyl)$_2$, —NH(C$_{1-3}$)alkyl-O(C$_{1-3}$)alkyl, —NH—(C$_{1-3}$)alkyl-COOH, —NHHet and Het;
      wherein said Het is a 6-membered saturated heterocycle containing one N heteroatom and optionally one additional heteroatom selected from N, O and S, which is optionally substituted with —COOH; and wherein the Het portion of said —NHHet is a 6-membered aromatic heterocycle containing one N heteroatom wherein said N heteroatom optionally exists in an oxidized state such that it is further bonded to an oxygen atom to form an N-oxide group; and
  d) —C(=O)N(R$^{83}$)R$^{84}$, wherein R$^{83}$ is selected from H and CH$_3$; and R$^{84}$ is selected from (C$_{1-4}$)alkyl and a 6-membered saturated heterocycle containing one N heteroatom and optionally one additional heteroatom selected from N, O and S;
    wherein said (C$_{1-4}$)alkyl is optionally substituted with one or more substituents each independently selected from —OH, —COOH and —SO$_3$H;
    or R$^{83}$ and R$^{84}$ are linked, together with the nitrogen atom to which they are bonded, to form a 6-membered monocyclic saturated heterocycle which optionally contains one or two additional heteroatoms each independently selected from N, O and S; said heterocycle being optionally substituted with —COOH.

12. A compound of the formula:

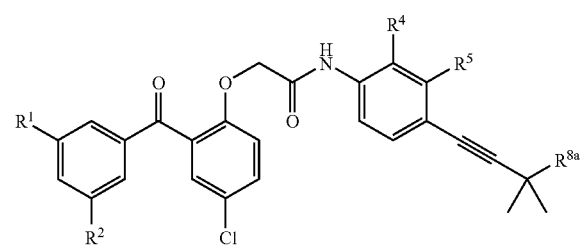

wherein $R^1$, $R^2$, $R^4$, $R^5$ and $R^{8a}$ are as defined in the table immediately below:

| $R^1$ | $R^2$ | $R^4$ | $R^5$ | $R^{8a}$ |
|---|---|---|---|---|
| F | CF$_3$ | Me | H | —OH |
| F | CF$_3$ | Cl | H | —OH |
| F | CF$_3$ | Me | H | —O—CH$_2$CO$_2$H |
| Cl | CN | Cl | H | —OH |
| F | CF$_3$ | Cl | H | —CO$_2$H |
| F | CF$_3$ | Me | H | —CO$_2$H |
| Cl | CN | Me | H | —CO$_2$H |
| Cl | CN | Cl | H | —CO$_2$H |
| F | CF$_3$ | Cl | H | —NH—CO—CH$_2$—N(Me)$_2$ |
| F | CF$_3$ | Cl | H | 4-pyridyl-N-oxide-C(=O)NH— |
| F | CF$_3$ | Cl | H | —NH$_2$ |
| Cl | CN | Cl | H | —NH$_2$ |
| Cl | CN | Cl | H | —NH—CO—CH$_2$—N(Me)$_2$ |
| Cl | CN | Cl | H | 4-pyridyl-N-oxide-C(=O)NH— |
| Cl | CN | Me | H | —OH |
| F | CF$_3$ | Cl | H | —O—CH$_2$CO$_2$H |
| Cl | CN | Me | H | —O—CH$_2$CO$_2$H |
| F | CF$_3$ | Me | H | —NH—CO—CH$_2$—N(Me)$_2$ |
| F | CF$_3$ | Me | H | 4-pyridyl-N-oxide-C(=O)NH— |
| Cl | CN | Me | H | —NH—CO—CH$_2$—N(Me)$_2$ |
| Cl | CN | Me | H | 4-pyridyl-N-oxide-C(=O)NH— |
| F | CF$_3$ | Cl | H | —NH—CO—CH$_2$—NH$_2$ |
| F | CF$_3$ | Cl | H | —NH—CO—CH$_2$—NHMe |
| F | CF$_3$ | Me | F | —NH$_2$ |
| F | CF$_3$ | Me | F | —NH—CO—CH$_2$—N(Me)$_2$ |
| F | CF$_3$ | Me | F | 4-pyridyl-N-oxide-C(=O)NH— |
| F | CF$_3$ | Cl | H | —NH—COC(Me)$_2$—NH$_2$ |
| F | CF$_3$ | Cl | H | 1-amino-cyclopropyl-C(=O)NH— |

-continued

| R¹ | R² | R⁴ | R⁵ | R⁸ᵃ |
|---|---|---|---|---|
| F | CF₃ | Cl | H |  |
| F | CF₃ | Cl | H |  |
| F | CF₃ | Cl | H |  |
| F | CF₃ | Cl | H | —NH—CO—CH₂CO₂H |
| F | CF₃ | Cl | H | —NH—CO—CHMeCO₂H |
| F | CF₃ | Cl | H |  |
| F | CF₃ | Cl | H | —NH—CH₂CO₂H |
| Br | OCF₃ | Cl | H | —CO₂H |
| Br | OCF₃ | Cl | F | —CO₂H |
| F | CF₃ | Cl | H | —CO—NH—CH₂CO₂H |
| F | CF₃ | Cl | H |  |
| F | CF₃ | Cl | H |  |
| F | CF₃ | Cl | H | —CO—N(Me)—CH₂CO₂H |
| F | CF₃ | Cl | H | —CO—NH—C(Me)₂CO₂H |
| F | CF₃ | Cl | F | —CO₂H |
| F | CF₃ | Me | F | —CO₂H |
| F | CF₃ | Cl | F | —NH₂ |
| F | CF₃ | Cl | F | —OH |
| F | CF₃ | Me | F | —OH |
| F | CF₃ | Cl | F | —O—CH₂CH₂OH |
| F | CF₃ | Cl | F |  |
| Br | CF₃ | Cl | H | —CO₂H |
| Br | CF₃ | Cl | F | —CO₂H |
| F | CF₃ | Cl | H | —NH—CO—C(Me)₂CO₂H |
| F | CF₃ | Cl | H | —NH—COCH(Et)CO₂H |

-continued

| R¹ | R² | R⁴ | R⁵ | R⁸ᵃ |
|---|---|---|---|---|
| F | CF₃ | Cl | H |  |
| F | CF₃ | Cl | H |  |
| F | CF₃ | Cl | H | —NH—CO—(CH₂)₂CO₂H |
| F | CF₃ | Cl | H | —NH—CO—CH₂C(Me)₂CO₂H |
| F | CF₃ | Cl | F | —O—CH₂CO₂H |
| F | CF₃ | Me | F | —O—CH₂CO₂H |
| F | CF₃ | Cl | F | —CO—NHOH |
| F | Br | Cl | H | —CO₂H |
| F | Br | Cl | F | —CO₂H |
| F | CF₃ | Cl | H |  |
| F | CF₃ | Cl | H |  |
| F | CF₃ | Cl | H |  |
| F | CF₃ | Cl | H | —NH—CO—C(Me)₂CH₂CO₂H |
| F | CF₃ | Cl | H |  |
| F | Br | Me | F | —CO₂H |
| F | CF₃ | Cl | F | —NH—CO—(CH₂)₃—SO₂NH₂ |
| F | CF₃ | Cl | F |  |
| F | CF₃ | Cl | F |  |
| F | CF₃ | NO₂ | H | —NH₂ |
| H | CN | Cl | H | —CO₂H |
| H | CN | Me | F | —CO₂H |
| Cl | CN | Me | F | —CO₂H |

-continued

| R¹ | R² | R⁴ | R⁵ | R⁸ᵃ |
|---|---|---|---|---|
| F | CF₃ | NO₂ | H | —NH—CO—(CH₂)₂CO₂H |
| F | CF₃ | NO₂ | H | ![isonicotinamide N-oxide] |
| F | CF₃ | NO₂ | H | —NH—CO—CH(Me)CO₂H |
| Cl | CN | Cl | F | —O—CH₂—CO₂H |
| Cl | CN | Me | F | —O—CH₂—CO₂H |
| Cl | CN | Cl | F | —CO₂H |
| F | CF₃ | Cl | H | ![morpholino amide] |
| F | CF₃ | Cl | H | ![dihydroxypropyl amide] |
| F | CF₃ | Cl | H | —CO—NH—(CH₂)₂—SO₃H |
| F | CF₃ | Cl | H | —CH₂OH |
| F | CF₃ | Cl | H | —CH₂O—CONH₂ |
| Cl | CN | Cl | H | —NH—CO—CH₂NHMe |
| Cl | CN | Cl | H | —NH—CO—C(Me)₂NH₂ |
| F | Br | Me | F | —O—CH₂CO₂H |
| F | Br | Me | F | —NH₂ |
| F | CF₃ | NO₂ | H | —CO₂H |
| Cl | CN | NO₂ | H | —CO₂H |
| F | Br | Me | F | ![nicotinamide N-oxide] |
| Cl | CN | NO₂ | H | —NH₂ |
| F | CF₃ | Cl | F | —NH—CO—(CH₂)₂CO₂H |
| F | CF₃ | Me | F | —NH—CO—(CH₂)₂CO₂H |
| Cl | CN | NO₂ | H | —NH—CO—(CH₂)₂CO₂H |
| F | Br | Me | F | —NH—CO—(CH₂)₂CO₂H |
| F | CF₃ | Cl | H | —NH—CO—CH₂OH |
| H | CN | Me | F | —O—CH₂—CO₂H |
| F | CF₃ | Cl | H | —NH—CO—Me |
| F | CF₃ | Me | F | —NH—CO—CH₂NHMe |
| F | CF₃ | Me | F | —NH—CO—C(Me)₂NH₂ |
| Cl | CN | Cl | F | —NH—CO—CH₂CH₂CO₂H |
| Cl | CN | Me | F | —NH—CO—CH₂CH₂CO₂H |
| Cl | Br | Cl | F | —NH—CO—CH₂CH₂CO₂H |
| Cl | Br | Me | F | —NH—CO—CH₂CH₂CO₂H |
| Cl | CN | Cl | H | —NH—CH₂CO₂H |
| Cl | CN | Cl | H | —NH—CO—CH₂NH₂ |
| Cl | CN | Cl | F | —NH₂ |
| Cl | CN | Me | F | —NH₂ |
| Cl | Br | Cl | F | —NH₂ |
| Cl | Br | Me | F | —NH₂ |
| CN | CF₃ | Cl | H | —CO₂H |
| cPr | Br | Cl | H | —CO₂H |
| cPr | Br | Me | F | —CO₂H |
| cPr | Br | Me | F | —O—CH₂CO₂H |
| cPr | Br | Cl | F | —O—CH₂CO₂H |
| cPr | CN | Me | F | —O—CH₂CO₂H |
| cPr | CN | Me | F | —CO₂H |

-continued

| R¹ | R² | R⁴ | R⁵ | R⁸ᵃ |
|---|---|---|---|---|
| F | CN | Me | F | —CO₂H |
| Cl | CN | Cl | H | ![piperazinyl acetamide] |
| Cl | CN | Cl | H | ![morpholinyl acetamide] |
| Cl | CN | Cl | H | —NH—COCH₂NH(CH₂)₂OMe |
| Cl | CN | Cl | F | —NH—CO—CH₂NHMe |
| Cl | CN | Me | F | —NH—CO—CH₂NHMe |
| Cl | Br | Cl | F | —NH—CO—CH₂NHMe |
| Cl | Br | Me | F | —NH—CO—CH₂NHMe |
| F | CF₃ | Cl | H | ![maleamic acid] |
| Cl | CN | Cl | H | ![maleamic acid] |
| F | Br | Cl | H | ![maleamic acid] |
| Cl | CN | Cl | H | —NH—CO—(CH₂)₂CO₂H |
| F | Br | Cl | H | —NH—CO—(CH₂)₂CO₂H |
| Cl | Br | Cl | H | —NH₂ |
| F | Cl | Me | F | —CO₂H |
| F | cPr | Me | F | —CO₂H |
| F | cPr | Cl | F | —CO₂H |
| F | cPr | Me | F | —O—CH₂CO₂H |
| Br | Br | Me | F | —CO₂H |
| F | cPr | Cl | F | —O—CH₂CO₂H |
| Cl | Br | Me | H | —CO₂H |
| Cl | Br | Cl | F | —CO₂H |
| Cl | Br | Me | F | —CO₂H |
| Cl | Br | Cl | H | —CO₂H |
| F | CN | Me | F | —O—CH₂CO₂H |
| CN | CF₃ | Me | F | —CO₂H |
| Br | CN | Me | F | —CO₂H |
| Cl | Br | Cl | H | —NH—CH₂CO₂H |
| Cl | CN | Me | F | —NH—CH₂CO₂H |
| Cl | Br | Cl | F | —NH—CH₂CO₂H |
| Cl | Br | Me | F | —NH—CH₂CO₂H |
| Cl | Br | Cl | H | —NH—CO—C(Me)₂NH₂ |
| Cl | CN | Cl | H | ![glycylamide] |
| F | OMe | Me | F | —CO₂H |
| F | ![methoxycarbonylmethoxy group] | Me | F | —CO₂H |

-continued

| R¹ | R² | R⁴ | R⁵ | R⁸ᵃ |
|---|---|---|---|---|
| H | Br | Me | F | —CO₂H |
| F | CF₃ | Me | F | ![pyridine with NHC(O) and CO₂H] |
| F | CF₃ | Me | F | ![pyridine with NHC(O) and CO₂H] |
| F | Cl | Me | F | —NH—CO—(CH₂)₂CO₂H |
| F | CN | Me | F | —NH—CO—(CH₂)₂CO₂H |
| H | cPr | Me | F | —CO₂H |
| H | cPr | Me | F | —O—CH₂CO₂H |
| F | OMe | Me | F | —NH—CO—(CH₂)₂CO₂H |
| F | CONH₂ | Me | F | —CO₂H |
| Br | CF₃ | Me | F | —CO₂H |
| Br | I | Me | F | —CO₂H |
| Br | I | Me | F | —O—CH₂CO₂H |
| F | cPr | Me | F | —NH₂ |
| F | cPr | Me | F | —NH—CO—(CH₂)₂CO₂H |
| cPr | CF₃ | Me | F | —O—CH₂CO₂H |
| cPr | CF₃ | Me | F | —CO₂H |
| F | CF₃ | Me | F | —NH—CO—CH₂C(Me)₂CO₂H |
| F | CF₃ | Me | F | ![pyrrolidine urea CO₂H] |
| F | CF₃ | Me | F | ![azetidine urea CO₂H] |
| F | CF₃ | Me | F | ![NHC(O)CH₂CH(Me)CO₂H] |
| F | CF₃ | Me | F | ![piperidine urea CO₂H] |
| F | cPr | Me | F | ![piperidine urea CO₂H] |
| F | CN | Me | F | ![piperidine urea CO₂H] |

-continued

| R¹ | R² | R⁴ | R⁵ | R⁸ᵃ |
|---|---|---|---|---|
| F | CN | Me | F | ![azetidine urea CO₂H] |
| F | CN | Me | F | ![NHC(O)C(Me)₂CH₂CO₂H] |
| F | CF₃ | Me | F | ![NHC(O)CH(Me)CH₂CO₂H] |
| F | CF₃ | Me | F | ![NHC(O)CH(Me)CH₂CO₂H] |
| F | CN | Me | F | ![NHC(O)CH(Me)CH₂CO₂H] |
| F | CN | Me | F | ![NHC(O)CH(Me)CH₂CO₂H] |
| F | CN | Me | F | ![pyridine with NHC(O) and CO₂H] |

13. A compound of the formula:

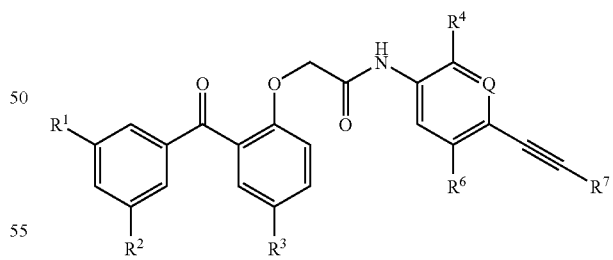

wherein wherein R¹, R², R R⁴, Q, R⁶ and R⁷ are as defined in the table immediately below:

| R¹ | R² | R³ | R⁴ | Q | R⁶ | R⁷ |
|---|---|---|---|---|---|---|
| F | CF₃ | Cl | Cl | CH | H | —CH₂CH₂OH |
| F | CF₃ | Cl | Cl | CH | H | —C(CF₃)₂OH |
| F | CF₃ | Cl | Cl | CH | F | —C(Me)₂NH₂ |

-continued

| R¹ | R² | R³ | R⁴ | Q | R⁶ | R⁷ |
|---|---|---|---|---|---|---|
| F | CF₃ | Cl | Cl | CH | F | 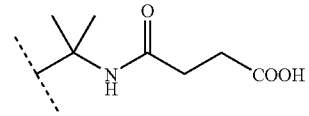 |
| F | CF₃ | Cl | Cl | CH | F | 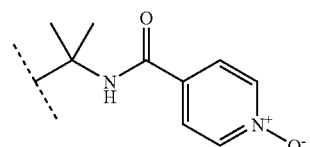 |
| F | CF₃ | Cl | Cl | CH | F | 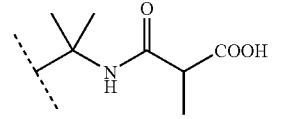 |
| F | CF₃ | Cl | Cl | CH | H | —C(Me)OH—CO₂H |
| F | CF₃ | Cl | Cl | CH | F | —C(Me)₂CO₂H |
| Cl | CN | Cl | Cl | CH | F | —C(Me)₂CO₂H |
| Cl | CN | Cl | Cl | CH | F | —C(Me)₂NH₂ |
| Cl | CN | Cl | Cl | CH | F | 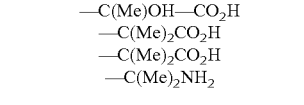 |

-continued

| R¹ | R² | R³ | R⁴ | Q | R⁶ | R⁷ |
|---|---|---|---|---|---|---|
| F | CF₃ | Cl | Cl | CH | H | 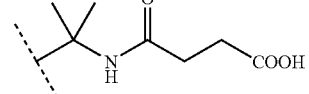 |
| F | CF₃ | Cl | Me | CF | H | 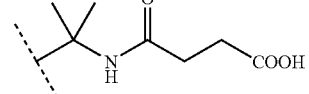 |
| F | Br | F | Me | CF | H | —C(Me)₂CO₂H |
| F | CF₃ | Cl | Me | N | H | —C(Me)₂CO₂H |
| F | CN | F | Me | CF | H | —C(Me)₂CO₂H. |

14. A pharmaceutical composition comprising a compound according to claim 1, or a pharmaceutically acceptable salt or ester thereof, and one or more pharmaceutically acceptable carriers.

15. A method of treating an HIV infection in a human which comprises administering a therapeutically effective amount of a compound according to claim 1 or a pharmaceutically acceptable salt or ester thereof.

* * * * *